(12) United States Patent
Rudolph et al.

(10) Patent No.: US 11,136,585 B2
(45) Date of Patent: Oct. 5, 2021

(54) UTRS INCREASING THE TRANSLATION EFFICIENCY OF RNA MOLECULES

(71) Applicant: Ethris GmbH, Planegg (DE)

(72) Inventors: Carsten Rudolph, Krailing (DE);
Manish Kumar Aneja, Munich (DE);
Mehrije Ferizi, Munich (DE);
Johannes Geiger, Munich (DE)

(73) Assignee: ethris GmbH, Planegg (DE)

( * ) Notice: Subject to any disclaimer, the term of this patent is extended or adjusted under 35 U.S.C. 154(b) by 518 days.

(21) Appl. No.: 15/739,147

(22) PCT Filed: Jun. 30, 2016

(86) PCT No.: PCT/EP2016/065297
§ 371 (c)(1),
(2) Date: Dec. 21, 2017

(87) PCT Pub. No.: WO2017/001554
PCT Pub. Date: Jan. 5, 2017

(65) Prior Publication Data
US 2019/0194669 A1 Jun. 27, 2019

(30) Foreign Application Priority Data

Jun. 30, 2015 (EP) .................................... 15174683

(51) Int. Cl.
| C07H 21/04 | (2006.01) |
| C12N 15/67 | (2006.01) |
| C07K 14/47 | (2006.01) |
| A61K 38/00 | (2006.01) |

(52) U.S. Cl.
CPC .............. *C12N 15/67* (2013.01); *C07K 14/47* (2013.01); *A61K 38/00* (2013.01)

(58) Field of Classification Search
CPC .................................................... C12N 15/67
See application file for complete search history.

(56) References Cited

U.S. PATENT DOCUMENTS

| 2005/0158822 A1 | 7/2005 | Pecker |
| 2012/0195936 A1 | 8/2012 | Rudolph et al. |

FOREIGN PATENT DOCUMENTS

| CN | 101768591 A | 7/2010 |
| CN | 104220599 A | 12/2014 |
| RU | 2008141401 A | 10/2010 |
| WO | WO 2000/053785 | 9/2000 |
| WO | WO 2007/024708 | 3/2007 |
| WO | WO 2011/012316 | 2/2011 |
| WO | WO2013143700 A2 | 10/2013 |
| WO | WO 2017/001554 | 1/2017 |

OTHER PUBLICATIONS

Guo, Zongru, "IV. Carbocyclic Nucleoside," Medical Chemistry, China Medical Science and Technology Press, ISBN: 7-5067-1163-X, p. 256.
Barrett, Lucy W., Sue Fletcher, and Steve D. Wilton. "Regulation of eukaryotic gene expression by the untranslated gene regions and other non-coding elements." Cellular and molecular life sciences 69.21 (2012): 3613-3634.
Dvir, Shlomi, et al. "Deciphering the rules by which 5'-UTR sequences affect protein expression in yeast." Proceedings of the National Academy of Sciences 110.30 (2013): E2792-E2801.
'T Hoen, Peter AC, et al. "mRNA degradation controls differentiation state-dependent differences in transcript and splice variant abundance." Nucleic acids research 39.2 (2011): 556-566.
Written Opinion and International Search Report in International Application No. PCT/EP2016/065297, dated Sep. 19, 2016.
Mie, Masayasu, et al. "Selection of mRNA 5'-untranslated region sequence with high translation efficiency through ribosome display." Biochemical and biophysical research communications 373.1 (2008): 48-52.
Iwakawa, Hiro-oki, et al. "Poly (A)-binding protein facilitates translation of an uncapped/nonpolyadenylated viral RNA by binding to the 3' untransiated region." Journal of virology 86.15 (2012): 7836-7849.

*Primary Examiner* — Kimberly Chong
(74) *Attorney, Agent, or Firm* — Morse, Barnes-Brown & Pendleton, P.C.; Lisa M. Warren, Esq.; Erin E. Bryan, Esq.

(57) ABSTRACT

Described is an RNA molecule comprising (a) a coding region coding for a polypeptide; and (b) upstream of said coding region one or more UTR(s) comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1; and/or (c) downstream of said coding region one or more UTR(s) comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2; wherein said polypeptide encoded by said coding region is not a cytochrome b-245 alpha polypeptide (CYBA). Moreover, described is a nucleic acid molecule encoding the RNA molecule according to the present invention. Further, described is a vector comprising the nucleic acid molecule according to the present invention and to a host cell comprising the vector according to the present invention. Further, described is a pharmaceutical composition comprising the RNA molecule according to the present invention and optionally a pharmaceutically acceptable carrier. Moreover, described is a kit comprising the RNA molecule according to the present invention. Finally, described is the use of one or more UTR(s) as defined in (b) and/or one or more UTR(s) as defined in (c) for increasing the efficiency of translating a coding region of an RNA molecule into a polypeptide or a protein encoded by said coding region.

Figure 1:
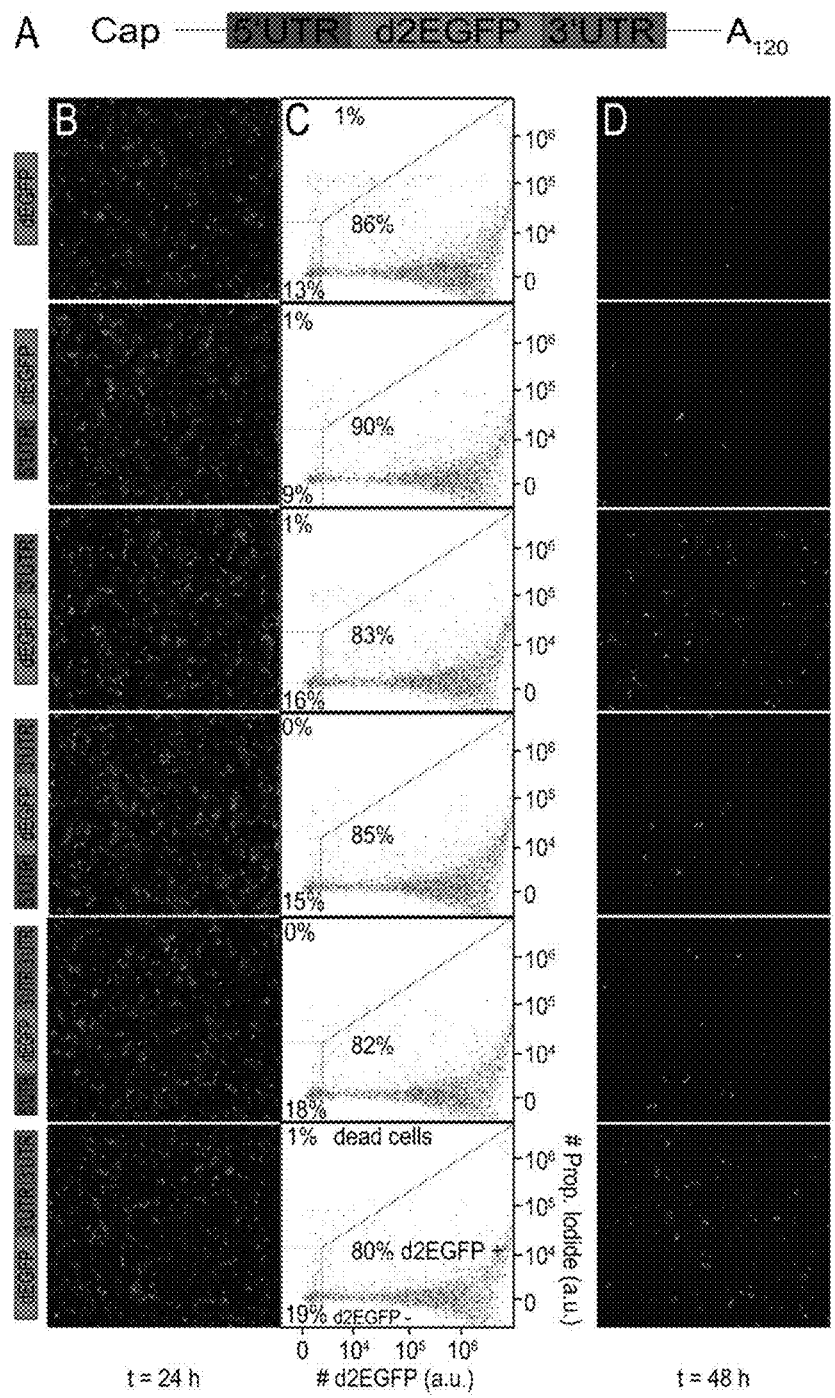

16 Claims, 12 Drawing Sheets
Specification includes a Sequence Listing.

Figure 2: MFI

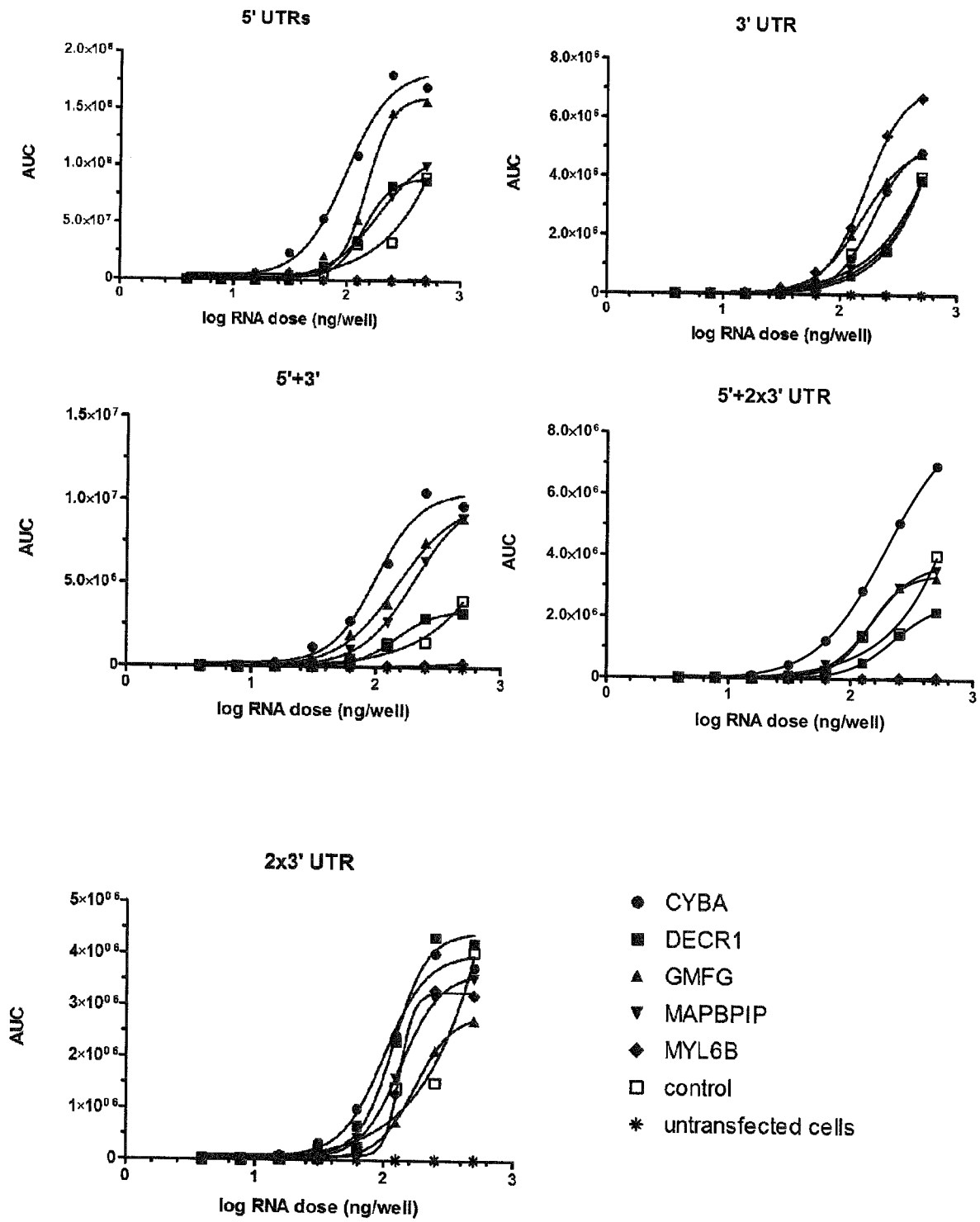
Figure 12: MetLuc expression in AUC – Comparison of cellular UTRs in NIH3T3

SEQUENCE LISTING

<160> NUMBER OF SEQ ID NOS: 11

<210> SEQ ID NO 1
<211> LENGTH: 36
<212> TYPE: RNA
<213> ORGANISM: Artificial
<220> FEATURE:
<223> OTHER INFORMATION: 5' UTR of the human cytochrome b-245 alpha
      polypeptide (CYBA) gene

<400> SEQUENCE: 1
cgcgccuagc aguguccag ccggguucgu gucgcc                                    36

<210> SEQ ID NO 2
<211> LENGTH: 64
<212> TYPE: RNA
<213> ORGANISM: Artificial
<220> FEATURE:
<223> OTHER INFORMATION: 3' UTR of the human cytochrome b-245 alpha
      polypeptide (CYBA) gene

<400> SEQUENCE: 2
ccucgccccg gaccugcccu cccgccaggu gcacccaccu gcaauaaaug cagcgaagcc         60
ggga                                                                      64

<210> SEQ ID NO 3
<211> LENGTH: 20
<212> TYPE: DNA
<213> ORGANISM: Artificial
<220> FEATURE:
<223> OTHER INFORMATION: d2EGFP-forward primer

<400> SEQUENCE: 3
caaccactac ctgagcaccc                                                     20

<210> SEQ ID NO 4
<211> LENGTH: 20
<212> TYPE: DNA
<213> ORGANISM: Artificial
<220> FEATURE:
<223> OTHER INFORMATION: d2EGFP-reverse primer

<400> SEQUENCE: 4
gtccatgccg agagtgatcc                                                    20

<210> SEQ ID NO 5
<211> LENGTH: 71
<212> TYPE: DNA
<213> ORGANISM: Artificial
<220> FEATURE:
<223> OTHER INFORMATION: DNA sequence encoding the 5' UTR of the human
      cytochrome b-245 alpha polypeptide (CYBA) gene

<400> SEQUENCE: 5
ggcggggttc ggccgggagc gcaggggcgg cagtgcgcgc ctagcagtgt cccagccggg        60
ttcgtgtcgc c                                                             71

<210> SEQ ID NO 6
<211> LENGTH: 70
<212> TYPE: DNA
<213> ORGANISM: Artificial
<220> FEATURE:
<223> OTHER INFORMATION: DNA sequence encoding the 3' UTR of the human
      cytochrome b-245 alpha polypeptide (CYBA) gene

<400> SEQUENCE: 6
cctcgccccg gacctgccct cccgccaggt gcacccacct gcaataaatg cagcgaagcc        60
gggagcgcgt                                                               70

<210> SEQ ID NO 7
<211> LENGTH: 778
<212> TYPE: RNA
<213> ORGANISM: Homo sapiens

<400> SEQUENCE: 7
ggcgggguuc ggccgggagc gcaggggcgg cagugcgcgc cuagcagugu cccagccggg        60
uucgugucgc caugggggcag aucgaguggg ccaugugggc caacgagcag gcgcuggcgu       120
ccggccugau ccucaucacc gggggcaucg uggccacagc ugggcgcuuc acccaguggu       180
acuuuggugc cuacuccauu guggcgggcg uguuugugug ccugcuggag uaccccggg         240 ggaagaggaa gaagggcucc accauggagc gcugggggaca gaaguacaug accgccgugg      300
ugaagcuguu cggccccuuu accaggaauu acuauguucg ggccguccug caucuccugc       360
ucucggugcc cgccggcuuc cugcuggcca ccauccuugg gaccgccugc cuggccauug       420
cgagcggcau cuaccuacug gcggcugugc guggcgagca guggacgccc aucgagccca      480
agccccggga gcggccgcag aucggaggca ccaucaagca gccgcccagc aaccccccgc       540
cgcggccccc ggccgaggcc cgcaagaagc cagcgaggga ggaggcugcg guggcggcgg      600
ggggaccccc gggaggucccc caggucaacc ccaucccggu gaccgacgag gucgugugac      660
cucgccccgg accugcccuc ccgccaggug cacccaccug caauaaaugc agcgaagccg       720
ggaaaaaaaa aaaaaaaaaa aaaaaaaaaa aaaaaaaaaa aaaaaaaaaa aaaaaaa           778

<210> SEQ ID NO 8
<211> LENGTH: 588
<212> TYPE: DNA
<213> ORGANISM: Homo sapiens

<400> SEQUENCE: 8
atggggcaga tcgagtgggc catgtgggcc aacgagcagg cgctggcgtc cggcctgatc        60
ctcatcaccg ggggcatcgt ggccacagct gggcgcttca cccagtggta ctttggtgcc      120

```
tactccattg tggcgggcgt gtttgtgtgc ctgctggagt accccegggg gaagaggaag    180 aagggctcca ccatggagcg ctggggacag aagtacatga ccgccgtggt gaagctgttc    240 gggccctttta ccaggaatta ctatgttcgg gccgtcctgc atctcctgct ctcggtgccc    300
gccggcttcc tgctggccac catccttggg accgcctgcc tggccattgc gagcggcatc    360
tacctactgg cggctgtgcg tggcgagcag tggacgccca tcgagcccaa gccccgggag    420
cggccgcaga tcggaggcac catcaagcag ccgcccagca accccccgcc gcggcccccg    480
gccgaggccc gcaagaagcc cagcgaggag gaggctgcgg tggcggcggg gggaccccccg    540 ggaggtcccc aggtcaaccc catcccggtg accgacgagg tcgtgtga                 588
```

<210> SEQ ID NO 9
<211> LENGTH: 195
<212> TYPE: PRT
<213> ORGANISM: Homo sapiens

<400> SEQUENCE: 9

```
Met Gly Gln Ile Glu Trp Ala Met Trp Ala Asn Glu Gln Ala Leu Ala
1               5                   10                  15

Ser Gly Leu Ile Leu Ile Thr Gly Gly Ile Val Ala Thr Ala Gly Arg
            20                  25                  30

Phe Thr Gln Trp Tyr Phe Gly Ala Tyr Ser Ile Val Ala Gly Val Phe
        35                  40                  45

Val Cys Leu Leu Glu Tyr Pro Arg Gly Lys Arg Lys Gly Ser Thr
    50                  55                  60

Met Glu Arg Trp Gly Gln Lys Tyr Met Thr Ala Val Val Lys Leu Phe
65                  70                  75                  80

Gly Pro Phe Thr Arg Asn Tyr Tyr Val Arg Ala Val Leu His Leu Leu
                85                  90                  95

Leu Ser Val Pro Ala Gly Phe Leu Leu Ala Thr Ile Leu Gly Thr Ala
            100                 105                 110

Cys Leu Ala Ile Ala Ser Gly Ile Tyr Leu Leu Ala Ala Val Arg Gly
        115                 120                 125

Glu Gln Trp Thr Pro Ile Glu Pro Lys Pro Arg Glu Arg Pro Gln Ile
    130                 135                 140

Gly Gly Thr Ile Lys Gln Pro Pro Ser Asn Pro Pro Arg Pro Pro
145                 150                 155                 160

Ala Glu Ala Arg Lys Lys Pro Ser Glu Glu Glu Ala Ala Val Ala Ala
                165                 170                 175

Gly Gly Pro Pro Gly Gly Pro Gln Val Asn Pro Ile Pro Val Thr Asp
            180                 185                 190

Glu Val Val
        195
```

<210> SEQ ID NO 10
<211> LENGTH: 56
<212> TYPE: DNA
<213> ORGANISM: Artificial
<220> FEATURE:
<223> OTHER INFORMATION: extended 5' UTR of the human cytochrome b-245
      alpha polypeptide (CYBA) gene

<400> SEQUENCE: 10

```
ggagcgcagg ggcggcagtg cgcgcctagc agtgtcccag ccggggttcgt gtcgcc         56
```

<210> SEQ ID NO 11

```
<211> LENGTH: 55
<212> TYPE: RNA
<213> ORGANISM: Artificial
<220> FEATURE:
<223> OTHER INFORMATION: extended 5' UTR of the human cytochrome b-245
      alpha polypeptide (CYBA) gene

<400> SEQUENCE: 11
ggagcgcagg ggcggcagug cgcgccuagc aguguccaag ccggguucgu gucgc         55
```

UTRS INCREASING THE TRANSLATION EFFICIENCY OF RNA MOLECULES

RELATED APPLICATIONS

This application is a national stage filing under 35 U.S.C. 371 of International Application No. PCT/EP2016/065297, filed Jun. 30, 2016, which claims the benefit of European Application No. 15174683.1, filed Jun. 30, 2015, the entire teachings of which are incorporated herein by reference. International Application No.: PCT/EP2016/065297 was published under PCT Article 21(2) in English.

The present invention relates to an RNA molecule comprising (a) a coding region coding for a polypeptide; and (b) upstream of said coding region one or more UTR(s) comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1; and/or (c) downstream of said coding region one or more UTR(s) comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2; wherein said polypeptide encoded by said coding region is not a cytochrome b-245 alpha polypeptide (CYBA). Moreover, the present invention relates to a nucleic acid molecule encoding the RNA molecule according to the present invention. Further, the present invention relates to a vector comprising the nucleic acid molecule according to the present invention and to a host cell comprising the vector according to the present invention. Further, the present invention relates to a pharmaceutical composition comprising the RNA molecule according to the present invention and optionally a pharmaceutically acceptable carrier. Moreover, the present invention relates to a kit comprising the RNA molecule according to the present invention. Finally, the present invention relates to the use of one or more UTR(s) as defined in (b) and/or one or more UTR(s) as defined in (c) for increasing the efficiency of translating a coding region of an RNA molecule into a polypeptide or a protein encoded by said coding region.

In recent years, messenger RNA (mRNA) has become increasingly relevant as a new drug entity. As opposed to DNA-based gene therapeutics, mRNA does not need to be transported into the nucleus but is directly translated into protein in the cytoplasm (1,2). This makes mRNA safer in avoiding potential insertional mutagenesis, an unlikely but existent risk of DNA gene medicines. As a consequence, mRNA therapeutics are emerging as promising alternatives for gene and protein replacement therapies in a broad variety of medical indications (1-4). However, the strong immunogenicity as well as the limited stability of conventional mRNA has to be overcome to further establish its clinical applicability. With respect to this, mRNA stability and in particular the translation rate of the mRNA is an essential parameter for envisaged medical applications because it determines, for example, dosing and the dosing intervals of mRNA drugs.

Several strategies have proven successful both at increasing the stability and reducing the immunogenic response triggered by mRNA administered to cells or organisms. Amongst these is the inclusion of chemically modified nucleotides (5). Kormann et al. have shown that the replacement of only 25% of uridine and cytidine residues by 2-thiouridine and 5-methyl-cytidine suffices to increase mRNA stability as well as to reduce the activation of innate immunity triggered by externally administered mRNA in vitro (WO2012/0195936 A1; WO2007024708 A2). Also, untranslated regions (UTRs) in mRNAs have been reported to play a pivotal role in regulating both mRNA stability and mRNA translation. UTRs are known to influence translational initiation, elongation, and termination, as well as mRNA stabilization and intracellular localization through their interaction with RNA binding proteins (6,7). Depending on the specific motives within the UTR, it can either enhance or decrease mRNA turnover (8-11). Recently, data on mRNA half-lives and the corresponding UTR sequences have been published (12, 43).

Accordingly, although in the prior art there are already described means and methods for increasing the stability of mRNA, reducing the immunogenic response triggered by mRNA administered to cells or organisms and increasing the translation efficiency there is still a need for improvements, in particular as regards further or alternate means to increase the translation efficiency since the translation efficiency is an essential parameter for envisaged medical applications because it determines, for example, dosing and the dosing intervals of mRNA drugs and, ultimately, determines the bioavailability of the final product, i.e., the encoded peptide or protein.

The present application addresses this need by providing the embodiments as defined in the claims.

In particular, the present application surprisingly found that a particular UTR confers an increased translational efficiency when fused to a given (foreign) mRNA. The UTR is derived from an mRNA of the human cytochrome b-245 alpha polypeptide (CYBA) gene. The CYBA gene comprises specific 5' and 3' UTRs. In general, 5' UTR motives such as upstream open reading frames (uORFs) or internal ribosomal entry sites (IRES) are known to be involved in gene regulation, particularly in translational initiation (13). The 3' UTRs can comprise even more regulatory functions than the 5'UTRs, some of them even hindering mRNA translation (14).

The finding of the present invention is all the more surprising since in the prior art no regulatory motives have been described for the CYBA 5' UTR unit. Although the CYBA's 3' UTR is known to contain two regulatory motives the finding of the present invention that the CYBA UTRs confer an increased translational efficiency when fused to a given mRNA is nevertheless surprising since these two motives are described in the context of the mRNA's stability but not in the increase of the translational efficiency. More specifically, the 3' UTR of CYBA is known to harbour a polyadenylation signal (PAS) which is known to interact with the cytoplasmic polyadenylation element binding protein (CPEB), as well as with the cleavage and polyadenylation signaling factor (CPSF) (11). CPEB is known to be responsible for the prolongation of the poly-A tail in the cytoplasm, whereas CPSF primes the pre-mRNA through cleavage at a specific site for the upcoming addition of poly-A (11, 14). A second regulatory motif contained in the CYBA 3' UTR is the insulin 3' UTR stability element (INS_SCE) (15). The INS_SCE sequence has been shown to bind to the polypyrimidine tract binding protein (PTB) under reducing conditions, increasing the mRNA half-life of insulin (15). Thus, both regulatory motives of the CYBA's 3' UTR are predominantly linked with the mRNA stability.

The DNA sequences displaying the nucleotide sequence of the human CYBA gene's 5'- and 3' UTRs present on the coding strand of the human CYBA gene are shown in the following Table 1

TABLE 1

Genetic code of the human CYBA gene UTRs

| Un-translated region | DNA sequence (from 5' to 3') |
|---|---|
| 5' | GGCGGGGTTCGGCCGGGAGCGCAGGGGCGGCAGTGC GCGCCTAGCAGTGTCCCAGCCGGGTTCGTGTCGCC (SEQ ID NO: 5) |
| 3' | CCTC<u>GCCCCGGACCTGCCCTCCCGCCAGGTGCACCC ACCTGC</u>AATAAATGCAGCGAAGCCGGGAGCGCGT (SEQ ID NO: 6) |

Table 1 shows the exact genetic code of the human CYBA gene UTRs. DNA sequences are shown from the 5' to the 3' end. The polyadenylation signal (PAS) of the 3' UTR is shown in bold letters and the insulin 3'UTR stability element (INS_SCE) is underlined. The 5' UTR consists of 71 base pairs, whereas the 3' UTR contains 70 base pairs. Both UTRs are shorter than average human UTRs, which consist of around 200 nucleotides in the case of 5'UTRs and approximately 1000 nucleotides in the case of 3'UTRs.

In the above Table 1, the DNA sequences displaying the human CYBA gene 5'- and 3' UTRs are shown as SEQ ID NO:5 and SEQ ID NO:6, respectively.

In view of the fact that the present invention predominantly relates to an RNA molecule reference is made in the following to the corresponding RNA sequences. Derived from the above DNA sequence SEQ ID NO:5 corresponds to the following UTR sequence on the RNA level:

(SEQ ID NO: 1)
5'-CGCGCCUAGCAGUGUCCCAGCCGGGUUCGUGUCGCC-3'.

This 5'UTR sequence immediately precedes the start codon of the human CYBA gene.

Derived from the above DNA sequence SEQ ID NO:6 corresponds to the following UTR sequence on the RNA level:

(SEQ ID NO: 2))
5'-CCUCGCCCCGGACCUGCCCUCCCGCCAGGUGCACCC ACCUGCAAUAAAUGCAGCGAAGCCGGGA-3'.

Another important feature influencing mRNA translation efficiency is the poly-A tail, which is located on the 3' end. It has been shown that a prolongation of the poly-A tail to 120 nucleotides has beneficial effects on protein expression, presumably because of the protective effect of longer poly-A tails against mRNA degradation (16). In contrast to long poly-A tails, mRNAs with poly-A tails shorter than 50 nucleotides are claimed not to be translated at all (11, 17). Hence, in mRNA therapy, recombinant mRNA constructs are advantageously to be furnished with a poly-A tail of 120 nucleotides or more. Degradation of most mRNA transcripts in eukaryotic cells begins with 3' to 5' exonucleolytic deadenylation, resulting in removal of most of the poly A-tail. Subsequently, two major pathways that are responsible for the degradation of the rest of the mRNA body are known to come into play. On the one hand, the 5' end is decapped by the Dcp1/Dcp2 complex, followed by 5'-3' exonucleolytic degradation that is catalyzed by Xrn1p. On the other hand, the exosome enables 3'-5' exoribonucleolytic degradation with the 5' cap being retained (18). Moreover, it is known that the 5' cap interaction with the 3' poly-A tail results in circular forms of the mRNA. It is assumed that the circular shape of the mRNA increases the initiation rate of ribosomes after translating the first stop codon and also protects mRNA against degradation (19).

The present application, inter alia, surprisingly found that an increase of the translational efficiency of a natural CYBA mRNA can be conferred to a foreign mRNA by virtue of flanking its coding sequence with combinations of shortened CYBA 5'- and 3'-UTRs. It is of note in this respect that both, the 5' UTR and the 3'UTR of the present invention as shown in SEQ ID NO:1 and SEQ ID NO:2, respectively, are shorter than the above DNA sequences displaying the human CYBA gene 5'- and 3' UTRs are shown as SEQ ID NO:5 and SEQ ID NO:6, respectively.

This has been done by a single-cell analysis of mRNA transfection time-lapse movies which has recently been shown to be capable of assessing individual expression time courses (26) while it has been reported that it is possible to use regular micropatterns to position cells on a regular grid of adhesion sites (27).

Hence, the present application has demonstrated that this technology offers the resolution to rapidly screen and compare different UTR combinations on a foreign mRNA. To address this, the coding sequence of destabilized enhanced green fluorescence protein (d2EGFP) has been chosen to artificially shorten the life cycle of the reporter protein inside the cell (28). The combinations included insertion of the respective CYBA UTRs at 5' or 3' ends, respectively, at both 5'- and 3' ends, at the 5' end combined with two repeats of the 3' UTR at the 3' end, or two repeats of 3' UTR without 5' UTR. All of these were compared to a control construct without UTRs. Protein and functional mRNA life times and the expression rate from each of the compared transcripts were assessed. Single-cell analysis of the dynamics of gene expression after mRNA transfection was compared to population based methods (flow cytometry, fluorescence microscopy imaging, and the bioluminescence measurement of luciferase activity). It has surprisingly been shown that the total protein expression over a period of three days for all UTR combinations compared to the control is improved.

This finding leads to the provision of the embodiments as characterized in the claims. Thus, the present invention relates to an RNA molecule comprising
(a) a coding region coding for a polypeptide; and
(b) upstream of said coding region one or more UTR(s) comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1; and/or
(c) downstream of said coding region one or more UTR(s) comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2;
wherein said polypeptide encoded by said coding region is not a cytochrome b-245 alpha polypeptide (CYBA).

A ribonucleic acid (RNA) molecule as used in accordance with the present invention relates to a polymeric molecule which is assembled as a chain of the nucleotides termed G, A, U, and C. Each nucleotide in RNA contains a ribose sugar, with carbons numbered 1' through 5'. A nitrogenous base is attached to the 1' position, in general, adenine (A), cytosine (C), guanine (G), or uracil (U). In a polymeric RNA molecule a phosphate group is attached to the 3' position of one ribose and the 5' position of the next. Thus, the nucleotides in a polymeric RNA molecule are covalently linked to each other wherein the phosphate group from one nucleotide binds to the 3' carbon on the subsequent nucleotide, thereby forming a phosphodiester bond. Accordingly, an RNA strand has a 5' end and a 3' end, so named for the carbons on the ribose ring. By convention, upstream and downstream relate to the 5' to 3' direction in which RNA transcription takes place. Preferably, the RNA molecule is a messenger RNA (mRNA) molecule. mRNA is a large family of RNA molecules that convey genetic information from DNA to the ribosome, where they specify the amino acid sequence of the protein products of gene expression. Following transcription of primary transcript mRNA (known as pre-mRNA) by RNA polymerase, processed, mature mRNA is translated into a polymer of amino acids: a protein, as summarized in the central dogma of molecular biology. As in DNA, mRNA genetic information is in the sequence of nucleotides, which are arranged into codons consisting of three bases each. Each codon encodes for a specific amino acid, except the stop codons, which terminate protein synthesis.

As will be outlined in more detail below, a ribonucleic acid (RNA) molecule of present invention comprises two or even three main modules, i.e., (a) a coding region coding for a polypeptide, (b) upstream of said coding region one or more UTRs, and/or (c) downstream of said coding region one or more UTRs which are different than the UTR(s) of module (b). Thus, the RNA molecule of the present invention resembles with respect to its structure a "normal" mRNA molecule which occurs in nature, harboring a coding region as well as (5' and 3') untranslated regions (UTRs) as well as, optionally, a poly-A tail.

The term "coding region" as used in accordance with the present invention relates to a polymeric RNA molecule which is composed of codons, which are decoded and translated into proteins by the ribosome in accordance with the information provided by the "genetic code". Coding regions commonly begin with a start codon and end with a stop codon. In general, the start codon is an AUG triplet and the stop codon is UAA, UAG, or UGA. In addition to being protein-coding, portions of coding regions may serve as regulatory sequences in the pre-mRNA as exonic splicing enhancers or exonic splicing silencers. The coding region of a gene coding for a polypeptide or a protein as used in accordance with the present invention is also known as the coding sequence or CDS (from coding DNA sequence) and is that portion of a gene's DNA or RNA, composed of exons, that codes for a polypeptide or protein. As mentioned, the region is bounded nearer the 5' end by a start codon and nearer the 3' end with a stop codon. The coding region in mRNA is flanked by the five prime untranslated region (5' UTR) and the three prime untranslated region (3' UTR) which are also parts of the exons. The coding region or CDS is that portion of the mRNA transcript, i.e., of the coding region coding for a polypeptide as used in accordance with the present invention, that is translated by a ribosome into a polypeptide or a protein.

The term "untranslated region" or "UTR" as used in accordance with the present invention relates sections of the mRNA upstream the start codon and downstream the stop codon that are not translated, and are, therefore, termed the five prime untranslated region (5' UTR) and three prime untranslated region (3' UTR), respectively. These regions are transcribed with the coding region and thus are exonic as they are present in the mature mRNA.

As used in the present invention, the 3' untranslated region (3'-UTR) relates to the section of messenger RNA (mRNA) that immediately follows the translation termination codon. An mRNA molecule is transcribed from the DNA sequence and is later translated into protein. Several regions of the mRNA molecule are not translated into protein including the 5' cap, 5' UTR, 3' UTR, and the poly-A tail. As used in the present invention, the 5' untranslated region (5' UTR) (also known as a Leader Sequence or Leader RNA) is the region of an mRNA that is directly upstream from the start codon. The 5' UTR begins at the transcription start site and ends one nucleotide (nt) before the start codon (usually AUG) of the coding region. In prokaryotes, the length of the 5' UTR tends to be 3-10 nucleotides long while in eukaryotes it tends to be, longer, generally from 100 to several thousand nucleotides long but sometimes also shorter UTRs occur in eukaryotes.

As used in the present invention, the 3' UTR may comprise regulatory regions within the 3'-untranslated region which are known to influence polyadenylation and stability of the mRNA. Many 3'-UTRs also contain AU-rich elements (AREs). Furthermore, the 3'-UTR contains the sequence AAUAAA that directs addition of several hundred adenine residues called the poly(A) tail to the end of the mRNA transcript.

As will be outlined in more detail further below, an RNA molecule as used in accordance with the present invention may also contain a poly-A tail. A poly-A tail is a long sequence of adenine nucleotides (often several hundred) added to the 3' end of the pre-mRNA by a process called polyadenylation. This tail promotes export from the nucleus and translation, and protects the mRNA from degradation.

Polyadenylation is the addition of a poly(A) tail to a messenger RNA. The poly(A) tail consists of multiple adenosine monophosphates; in other words, it is a stretch of RNA that has only adenine bases. In eukaryotes, polyadenylation is part of the process that produces mature messenger RNA (mRNA) for translation.

As mentioned above, the RNA molecule of the present invention preferably comprises two or three main modules, i.e., (a) a coding region coding for a polypeptide; and (b) upstream of said coding region one or more UTR(s) comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1; and/or (c) downstream of said coding region one or more UTR(s) comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2.

Thus, it is mandatory that the RNA molecule of the present invention comprises two main modules, i.e., the above module (a) and module (b) and optionally also module (c).

In another preferred embodiment, the RNA molecule of the present invention comprises three main modules, i.e., the above module (a) and module (b) and module (c). Yet, while module (a) is mandatory, it is also envisaged that the RNA molecule may also lack one of the modules (b) or (c).

One module of the RNA molecule, i.e., "a coding region coding for a polypeptide" (module (a)) is not particularly limited and may be any desired coding region which is to be expressed in a given cell. Thus, this module may be a coding region coding for a desired polypeptide, i.e., the desired final product. The present invention is not limited with respect to the "coding region coding for a polypeptide" since the nature of the coding region depends on the desired product which is to be produced in the cell. Such coding region can also be a nucleotide sequence which differs from a known natural sequence and contains mutations (i.e. point mutations, insertion mutation, deletions and combinations thereof). Moreover, such a coding region may partly or to the full extent be a codon optimized sequence derived from the natural sequence to be used as module (a). Codon optimization is a technique to maximize the protein expression by increasing the translational efficiency of a gene of interest. It is known that natural genes do not use the available codons randomly, but show a certain preference for particular codons for the same amino acid. Thus, because of the degeneracy of the genetic code—one amino acid can be encoded by several codons—transforming the nucleotide sequence of a gene of interest into a set of preferred codons of the same or another species. Yet, the coding region (module (a)) of the cytochrome b-245 alpha polypeptide (CYBA) gene is excluded and, accordingly, the RNA molecule of the present invention is an RNA molecule comprising module (a), i.e., a coding region coding for a polypeptide wherein, however, said coding region coding for a polypeptide in (a) is not a coding region coding for a cytochrome b-245 alpha polypeptide (CYBA). Coding regions encoding a cytochrome b-245 alpha polypeptide (CYBA) as well as the corresponding amino acid sequences are known in the art. Cytochrome b-245 alpha polypeptides are known to be capable of producing superoxide and are known to be involved in phagocytosis. An example of a coding region coding for a cytochrome b-245 alpha polypeptide (CYBA) is shown in SEQ ID NO:9. Thus, in a preferred embodiment, the RNA molecule of the present invention is an RNA molecule comprising module (a), i.e., a coding region coding for a polypeptide wherein said coding region coding for a polypeptide in (a) is not a coding region coding for a cytochrome b-245 alpha polypeptide (CYBA) as shown in SEQ ID NO:9 or a coding region which shows an amino acid sequence which is at least x % identical to SEQ ID NO:9 with x being an integer between 90 and 100, preferably 95, 96, 97, 98 or 99. As an example, on the DNA-level, a sequence representing the coding region for a polypeptide coding for a cytochrome b-245 alpha polypeptide (CYBA) is shown in SEQ ID NO:8.

As mentioned, module (a) is not particularly limited and may be any desired coding region which is to be expressed in a given cell. Thus, in the context of the present invention, "coding region" should be understood to mean any polyribonucleotide molecule which, if introduced into a cell, is translatable to a polypeptide/protein or fragment thereof. The terms "polypeptide" and "protein" here encompass any kind of amino acid sequence, i.e., chains of two or more amino acids which are each linked via peptide bonds and also includes peptides and fusion proteins.

In a preferred embodiment, the "coding region coding for a polypeptide" contains a ribonucleotide sequence which encodes a polypeptide/protein or fragment thereof whose function in the cell or in the vicinity of the cell is needed or beneficial, e.g., a protein the lack or defective form of which is a trigger for a disease or an illness, the provision of which can moderate or prevent a disease or an illness, or a protein which can promote a process which is beneficial for the body, in a cell or its vicinity. The coding region may contain the sequence for the complete protein or a functional variant thereof. Further, the ribonucleotide sequence of the coding region can encode a protein which acts as a factor, inducer, regulator, stimulator or enzyme, or a functional fragment thereof, where this protein is one whose function is necessary in order to remedy a disorder, in particular a metabolic disorder or in order to initiate processes in vivo such as the formation of new blood vessels, tissues, etc. Here, functional variant is understood to mean a fragment which in the cell can undertake the function of the protein whose function in the cell is needed or the lack or defective form whereof is pathogenic.

In a preferred embodiment, the "coding region coding for a polypeptide" encodes a therapeutically or pharmaceutically active polypeptide or protein having a therapeutic or preventive effect. As such, the RNA molecule of the present invention comprising said "coding region coding for a polypeptide" may be used in nucleic acid therapy and related applications. In this context, in accordance with the invention, an increased efficiency of translating a coding region of an RNA molecule into a polypeptide or a protein encoded by said coding region of an introduced exogenous RNA molecule may be intended to compensate or complement endogenous gene expression, in particular in cases where an endogenous gene is defective or silent, leading to no, insufficient or a defective or a dysfunctional product of gene expression such as is the case with many metabolic and hereditary diseases like cystic fibrosis, hemophilia or muscular dystrophy to name a few. An increased efficiency of translating a coding region of an RNA molecule into a polypeptide of introduced exogenous RNA molecules of the present invention may also be intended to have the product of the expression interact or interfere with any endogenous cellular process such as the regulation of gene expression, signal transduction and other cellular processes. The increased efficiency of translating a coding region of an RNA molecule into a polypeptide of introduced exogenous RNA molecules may also be intended to give rise to an immune response in context of the organism in which a transfected or transduced cell resides or is made to reside. Examples are the genetic modification of antigen-presenting cells such as dendritic cells in order to have them present an antigen for vaccination purposes. Another example is the increased efficiency of translating a coding region of an RNA molecule into a polypeptide wherein said coding region encodes cytokines. This may, e.g., be desirable in tumors in order to elicit a tumor-specific immune response. Furthermore, the increased efficiency of translating a coding region of an RNA molecule into a polypeptide of an exogenous RNA molecule may also be intended to generate in vivo or ex vivo transiently genetically modified cells for cellular therapies such as modified T-cells or precursor or stem or other cells for regenerative medicine.

In other preferred embodiments, the "coding region coding for a polypeptide" may encode proteins which play a part in growth processes and angiogenesis, which are for example necessary in controlled regeneration and can then be formed specifically by introduction of the RNA molecule according to the invention. This can for example be useful in growth processes or for the treatment of bone defects, tissue defects and in the context of implantation and transplantation.

As mentioned, the RNA molecule of the present invention comprising a "coding region coding for a polypeptide" can appropriately be used in any case where a polypeptide or a protein, which would naturally be present in the body but is not present or is present in deficient form or in too small a quantity because of gene defects or diseases, is to be provided to the body. Proteins and the genes encoding them, the deficiency or defect whereof are linked with a disease, are known. The respective intact version of the coding region coding for the intact polypeptide or protein can be used in accordance with the present invention.

Numerous genetic disorders, caused by the mutation of a single gene are known and candidates for mRNA therapeutic approaches. Disorders caused by single-gene mutations, like cystic fibrosis, hemophilia and many others, can be dominant or recessive with respect to the likelihood that a certain trait will appear in the offspring. While a dominant allele manifests a phenotype in individuals who have only one copy of the allele, for a recessive allele the individual must have two copies, one from each parent to become manifest. In contrast, polygenic disorders are caused by two or more genes and the manifestation of the respective disease is often fluent and associated to environmental factors. Examples for polygenic disorders are hypertension, elevated cholesterol level, cancer, neurodegenerative disorders, mental illness and others. Also in these cases therapeutic mRNA representing one or more of these genes may be beneficial to those patients. Furthermore, a genetic disorder must not have been passed down from the parents' genes, but can also be caused by new mutations. Also in these cases therapeutic mRNA representing the correct gene sequence may be beneficial to the patients.

An online catalog with presently 22,993 entries of Human Genes and Genetic Disorders together with their respective genes and a description of their phenotypes are available at the ONIM (Online Mendelian Inheritance in Man) webpage (http://onim.org); sequences of each are available from the Uniprot database (http://www.uniprot.org). As non-limiting examples, the following Table 2 lists some congenital diseases, and the corresponding gene(s). Due to the high degree of interaction of cellular signaling pathways, the mutation of a certain gene causes a multiply of pathogenic symptoms, of which only a characteristic one is listed in Table 2.

In some embodiments of the present invention, the therapeutic protein is chosen from the cellular proteins listed in Table 2. Thus, compositions of the invention may comprise an mRNA encoding a therapeutic cellular protein, wherein the encoded therapeutic protein is one listed in Table 2 or a homolog thereof.

In another embodiment of the present invention, the therapeutic protein is chosen from the secreted proteins listed in Table 2. Thus, compositions of the invention may comprise an mRNA encoding a therapeutic fusion protein, wherein the encoded therapeutic protein or a homolog thereof is one listed in Table 2 and the second protein is a signal peptide that allows the secretion of the therapeutic protein. A signal peptide is a short, typically 5-30 amino acids long, amino acids sequence present at the N-terminus of said therapeutic protein and that leads the fusion protein towards the cell's secretory pathway via certain organelles (i.e. the endoplasmic reticulum, the golgi-apparatus or the endosomes). Thus, such fusion protein is secreted from the cell or from a cellular organelle or inserted into a cellular membrane (e.g. multi-spanning trans-membrane proteins) at a cellular compartment or at the cell's surface.

Thus, in preferred embodiments of the present invention the "coding region coding for a polypeptide" (module (a)) may encode, but is not limited to the following genes that cause, predispose or protect from diseases. Non-limiting examples of such disorders that may be treated (or prevented) include those wherein said polypeptide, protein or peptide is selected from the group consisting of the ones as outlined in the following Table 2.

In some embodiments, the "coding region coding for a polypeptide" may be translated into a partial or full length protein comprising cellular activity at a level equal to or greater than that of the native protein. In some embodiments, the "coding region coding for a polypeptide" encodes a therapeutically or pharmaceutically active polypeptide, protein or peptide having a therapeutic or preventive effect, wherein said polypeptide, protein or peptide is selected from the group consisting of the ones as outlined in the following Table 2. The "coding region coding for a polypeptide" may be used to express a partial or full length protein with cellular activity at a level equal to or less than that of the native protein. This may allow the treatment of diseases for which the administration of an RNA molecule can be indicated.

TABLE 2

| Non-limiting examples of human genes and genetic disorders | | |
|---|---|---|
| Disease | Pathology | Gene, heredity |
| Blood diseases | | |
| Fanconi Anemia | Anemia and neutropenia, evidence that a DNA repair mechanism is affected | FANCA, autosomal recessive |
| Hemophilia-A | Abnormal bleeding | Coagulation Factor VIII, X-chromosomal recessive |
| Hemophilia-B | Abnormal bleeding | Coagulation Factor IX, X-chromosomal recessive |
| Hereditary Spherocytosis (various types) | spherical-shaped erythrocytes (spherocytes) | Ankyrin (ANK1) |
| Paroxysmal nocturnal hemoglobinuria | Anemia and presence of blood in the urine | PIG-A, X-chromosomal |
| Porphyria cutanea tarda | Overproduction of heme, iron overload | Uroporphyrinogen decarboxylase (UROD), autosomal recessive |
| Severe combined immune deficiency (SCID) | Due to impaired DNA synthesis severe immune deficiency in humoral and cellular immunity | Adenosine deaminase, autosomal recessive, IL-2R-γ, JAK3, (IL-7R-α, RAG1/2, Artemis, CD3δ, CD3ε |

TABLE 2-continued

Non-limiting examples of human genes and genetic disorders

| Disease | Pathology | Gene, heredity |
|---|---|---|
| Sickle-cell anemia | Abnormal hemoglobin (HbS) | β-Hemoglobin (HB), autosomal recessive |
| Thalassemia (α- and β form) | Lack of α- or β hemoglobin resulting in anemia | Deletion of HBA1 and/or HBA2, |
| Von Willebrand disease (three types known, Type-III is most severe) | Abnormal bleeding, hemorrhage similar to hemophilia A and B | Autosomal dominant and recessive forms |
| Cancer | | |
| Malignant melanoma | P16 mutation leads to uncontrolled proliferation of fibroblasts | Cyclic dependant kinase inhibitor 2 (CDKN2) |
| Neurofibromatosis (2 types) | Benign tumors on auditory nerves leads to deafness | NF1, NF2, autosomal dominant |
| Deafness (Ear) | | |
| Deafness | Hearing loss | Deafness-1A (DFNB1), autosomal recessive |
| Pendred syndrome | Hearing loss | Pendrin (PDS), autosomal recessive |
| Heart | | |
| Ataxia telangiectasia | DNA damage repair disturbed, | ATM, |
| Atherosclerosis | Increase of blood cholesterol | apoE, |
| LQT Syndrome (Long QT) | Potassium channel defect | LQT1 and other genes |
| Von-Hippel Lindau Syndrome | Abnormal growth of blood vessels, can lead to cancer | VHL, autosomal dominant |
| William's Beuren Syndrome | Deletion of elastin results in vascular defects, supravalvular aortic stenosis | Deletion of elastin and LIM kinase genes |
| Metabolic disorders and glycogen storage diseases | | |
| Adrenoleukodystrophy | Disturbed fatty acid transport and metabolism | ABCD1, X-chromosomal |
| Alkaptonuria | Nitrogen metabolism defect, Urine turns dark when exposed to oxygen | Homogentisic Oxidase, autosomal recessive |
| Diabetes type I | Disturbed insulin production | IDDM1, IDDM2, GCK, . . . |
| Galactosemia | disorder of galactose metabolism | Galactose-1-phosphate uridyltransferase gene (GALT), autosomal recessive |
| Gauche disease | Disturbance of fat metabolism | Glucocerebrosidase |
| Glucose Galactosidase Malabsorption | Disturbed glucose and galactose transport out of the intestinal lumen resulting in diarrhea | SGLT1, autosomal recessive |
| Glycogen storage disease Type I, Von-Gierke's disease | Accumulation of glucose in liver and kidney | Glucose-6-Phosphatase, autosomal recessive |
| Glycogen storage disease Type II, Pompe's disease | Accumulation of glycogen in liver, heart, skeletal muscle, cardiomegaly | α-1-Glucosidase, autosomal recessive |
| Glycogen storage disease Type III, Cori's disease | Accumulation of glycogen in liver, heart, skeletal muscle, hepatoomegaly | Debranching enzyme, autosomal recessive |
| Glycogen storage disease Type V, McArdle's disease | Cannot untilize glycogen in muscle cells | Muscle phosphorylase, autosomal recessive |

TABLE 2-continued

Non-limiting examples of human genes and genetic disorders

| Disease | Pathology | Gene, heredity |
|---|---|---|
| Glucose-6-Phosphate Dehydrogenase | Inability to maintain glutathione leads to hemolytic anemia | G6PD, X-chromosomal recessive |
| Hereditary Hemochromatosis (4 types) | Excess of iron in the body (esp. liver) due to excessive iron absorption in the gut | Hemochromatosis (HFE) |
| Homocystinuria | Nitrogen metabolism defect | Cystathione synthetase defect, autosomal recessive |
| Lesh Nyhan Syndrome | Accumulation of uric acid leading to gout, ureate stones and muscle loss | HPRT1, X-chromosomal |
| Maple Syrup Urine Disease | Amino acid metabolism defect leads to the accumulation of α-Ketoacides and death in the first months if untreated | Branched-chain-alpha-dehydrogenase (BCKDH) |
| Menkes' Syndrome | Reduced ability to absorb copper, leads to death in infancy if untreated | X-chromosomal; ATP7A, X-chromosomal recessive |
| Obesity | Elevated body weight | Polygenic, elevated leptin levels may play a role |
| Phenylketonuria | Inability to break down Phenylalanine into tyrosine leads to mental retardation | Phenylalanine hydroxylase (PAH), autosomal recessive |
| Tangier disease | reduced levels of plasma high density lipoproteins | ATP-binding cassette-1 gene (ABCA1) |
| Zellweger Syndrome (leads to death in infants) | High levels of iron and copper in the blood | PXR1 (receptor on the surface of peroxisomes) |
| Wilsons Disease | Copper accumulation in brain and liver | ATP7B (P-type ATPase), autosomal recessive |
| Musculoskeletal system | | |
| Achondroplasis | Short stature with a large head due to slow proliferation of chondrocytes | Fibroblast growth factor receptor 3 (FGF3R), |
| Charcot-Marie-Tooth Syndrome and its more severe form Dejerine-Sottas Syndrome | Degeneration of the muscles in limbs | Different forms caused by different gene mutations, autosomal recessive and X-chromosomal |
| Cockayne syndrome (2 types) | Premature aging and short stature, loss of "on the fly" DNA repair | group 8 excision repair cross-complementing protein (ERCC8) |
| Chondroectodermal dysplasia | Malformation of bones and polydactyly | EVC, autosomal recessive |
| Diastrophic dysplasia (DTD) | Malformed hands, sulfate transporter defect | DTDST gene |
| Duchenne muscular dystrophy | Enlargement of muscle tissue with subsequent loss of function | DMD, X-chromosomal recessive |
| Fibrodysplasia Ossificans Progressiva | Heterotopic bone formation | NOG, BMP, Autosomal dominant |
| Friedreich's ataxia | Heart enlargement and progressive loss of muscular coordination | Frataxin, autosomal recessive |
| Hypophosphatasia | Production of an abnormal version of alkaline phosphatase affecting the mineralization process | ALPL, autosomal recessive |
| Marfan Syndrome | Connective tissue disorder due fibrillin deficiency | Fibrillin 1 (FBN), autosomal dominant |

TABLE 2-continued

Non-limiting examples of human genes and genetic disorders

| Disease | Pathology | Gene, heredity |
|---|---|---|
| Myotonic dystrophy (onset during young adulthood) | Protein kinase defect in skeletal muscle cells | Dystrophia myotonica protein kinase (DMPK), autosomal dominant |
| Osteogenesis imperfect (various types) | Defect in type-I collagen formation leads to multiple fractures after birth | COL1A1, COL1A2 |
| Prader-Willi Syndrome | Decreased muscle tone and mental retardation | SNRPN (small ribinucleoprotein N) deleted due to a deletion on chromosome 15 |
| Neurons and Brain | | |
| Alzheimer disease | Increased amyloid production, progressive inability to remember facts | Polygenic, PS1, PS2, . . . |
| Amyotrophic lateral sclerosis (ALS) (various forms) | Progressive degeneration of motor neuron cells (defect in elimination superoxide radicals) | Superoxide dismutase 1 (SOD1), various genes involved |
| Angelman syndrome | Mental retardation with inadequate laughing | Genomic imprinting on chromosome 15 |
| Pyruvat dehydrogenase | Neurological defects if untreated | Pyruvat dehydrogenase, autosomal recessive |
| Refsum disease | Accumulation of phytanic acid leads to peripheral neuropathy | Phytanoyl-CoA hydroxylase (PHYH), autosomal recessive |
| Rett's syndrome | Mental retardation with arrested development between 6 and 18 months of age | Methyl-CpG-binding protein-2 (MECP2), X-chromosomal dominant |
| Tay-Sachs disease (various forms of severity) | Disturbed break down of GM2 ganglioside leads to neurological damage | HEXA (β-hexosaminidas A), autosomal recessive |
| LaFora Disease | Aggressive form of epilepsy | EPM2A, autosomal recessive |
| Essential tremor (variable forms) | Uncontrollable shaking | ETM1, ETM2, autosomal dominant |
| Fragile X syndrome | Lack of FMR1 RNA binding protein, mental retardation | FMR1 gene is not expressed due to an CGG amplification in the 5'UTR region |
| Huntington's disease | Progressive dementia with onset in adulthood | HTT (huntingtin), autosomal dominant |
| Intestine | | |
| Bartter's syndrome (3 types) | Renal disease | Kidney chloride channel B gene (CLCNKB), autosomal recessive |
| Polycystic kidney disease (2 types) | renal disease | PDK1, PDK2, autosomal dominant, there is also a autosomal recessive form known (ARPKD) |
| Lung | | |
| Alpha-1-antitrypsin | Defect alveoli due to uncontrolled release of elastase | SERPINA1, autosomal codominant |
| Asthma | Chronic inflammatory disorder of the airways | Polygenic |
| Cystic fibrosis | Excessively viscous mucous due to defective Cl$^-$ ion transport | CFTR (cystic fibrosis conductance transmembrane regulator), autosomal recessive |
| Surfactant metabolism dysfunction (various types) | Newborns are of normal body weight, but all fail to inflate | ATP-binding cassette transporter (ABCA3) |

TABLE 2-continued

Non-limiting examples of human genes and genetic disorders

| Disease | Pathology | Gene, heredity |
|---|---|---|
| Primary ciliary dyskinesia | Excessively viscous mucous due to defective/missing cilia function | CCNO, CCDC40 among others |
| Lysosomal storage diseases | | |
| Fabry's disease | Beyond others, skin lesions due to the accumulation of ceramide trihexoside | α-Galactosidase A, X-chromosomal recessive |
| Gaucher's Disease Type-I: adult form (normal lifespan under treatment) Type-II: infantile form (death before age 1) Type-III: juvenile form (onset in early childhood, less severe than Type-II) | Accumulation of glucocerebrosides (gangliosides, sphingolipids) | Glucocerebrosidase, autosomal recessive, |
| Hunter's Syndrome | Accumulation of mucopolysaccharides | L-iduronosulfat sulfatase, X-chromosomal recessive |
| Hurler's Syndrome (death by age of 10) | Accumulation of mucopolysaccharides | α-L-iduronidase, autosomal recessive |
| Niemann-Pick Disease (three distinct forms A, B, C) | Defect in releasing Cholesterol from lysosomes, accumulation of Sphingomyelin | Sphingomyelinase, autosomal recessive |
| Tay-Sachs disease (death by age of 4) | Accumulation of Gm2 ganglioside in neuronal cells | Hexosaminidase A, autosomal recessive |
| Skin | | |
| Albinism | Nitrogen metabolism defect | Tyrosinase deficiency, autosomal recessive |
| Albinism, oculocutaneous, type II | Reduced biosynthesis of melanin pigment | OCA2, autosomal recessive |
| Ehlers-Danlos Syndrome (various types) | Diaphragmatic hernia, common, retinal detachment | Various defects in collagen synthesis |
| Epidermolysis bullosa (various types including EB simplex, Junctional EB, Dystrophic EB and Kindler syndrome) | Defects in maintenance of keratinocyte structural stability or adhesion of the keratinocyte to the underlying dermis | Epidermolysis bullosa macular type (EBM), Epidermolysis bullosa 3 progressiva (EBR3), Epidermolysis bullosa 4 pseudojunctual (EBR4), Desmoplakin (DSP), Plakophilin-1 (PKP1), kreatin (KRT5, KRT14), plectin (PLEC), ITGA6, integrin subunit (ITGB4), laminin subunits (LAMA3, LAMP3, LAMB3, LAMC2), collagen (COL17A1, COL7A1 (autosomal dominant), FERMT1, autosomal recessive |
| Hartnup's disease | Defect in tryptophan uptake in the gastrointestinal tract, light-sensitive skin | SLC6A19, autosomal recessive |
| Hereditary Hemorrhagic Telangiectasia, Osler-Weber-Rendu Syndrome | Telangiectasia of the skin and mucous membranes | Endoglin (ENG), autosomal dominant |
| Hypercholesterolemia, familial | elevation of serum cholesterol bound to low density lipoprotein, accumulation in skin and arteriosclerosis | Low-density lipoprotein receptor (LDLR), apolipoprotein B (APOB), autosomal dominant |
| Xeroderma pigmentosa | skin defect and melanoma due to UV exposure | DNA repair defect, autosomal recessive |

TABLE 2-continued

Non-limiting examples of human genes and genetic disorders

| Disease | Pathology | Gene, heredity |
|---|---|---|
| Male pattern baldness | Disturbed conversion of testosterone into dihydrotestosterone in the skin | 5-α-reductase |
| Genetic liver diseases | | |
| Amino acid metabolism disorders | Disruptions in the multistep process that breaks down the amino acid tyrosine and phenylalanine | FAH, TAT, HPD, autosomal recessive |
| Beta-thalassemia intermedia | Shortage of mature red blood cells | HBB, autosomal recessive |
| Crigler-Najjar syndrome | Deficiency in glucuronidation in which bilirubin gets dissolvable in water | UGT1A1, autosomal recessive |
| Fatty acid oxidation disorders | Deficiency in processing of long-chain fatty acids and very long-chain fatty acids resulting in lethargy and hypoglycemia | HADHA, ACADVL autosomal recessive |
| Fructose metabolism disorders | Impaired gluconeogenesis causing hypoglycemia | FBP1, ALDOB, autosomal recessive |
| Galactosemia | Deficiency in processing galactose | GALT, GALK1, GALE, autosomal recessive |
| Glycogen storage diseases | Disturbed breackdown of glucose 6-phosphate and glycogen leads to accumulation of glycogen as well as abnormal glycogen molecules causing cell damage | G6PC, SLC37A4, AGL, GBE1, autosomal recessive |
| Heme biosynthesis disorder | Decrease of uroporphyrinogen decarboxylase resulting in accumulation of compounds called porphyrins causing toxic levels in liver | UROD autosomal dominant, ALAS2 X-limked dominant, ALAD autosomal recessive |
| Lipid metabolism (transport) disorders | Shortage of functional protein, which prevents movement of cholesterol and other lipids, leading to their accumulation in cells | NPC1, NPC2 autosomal recessive, LDLR, autosomal dominant |
| Metal metabolism disorders | Disorders in the storage and transport of iron and copper resulting in accumulation in tissues and organs | ATP7B, HAMP, HFE, HFE2, autosomal recessive |
| Organic acid disorders (Acidurias/Acidemias) | Disrupted break down of several protein building blocks (amino acids), certain lipids, and cholesterol | BCKDHA, BCKDHB, and DBT, PCCA and PCCB, MUT, MMAA, MMAB, MMADHC, MCEE, IVD, MCCC1 or MCCC2, autosomal recessive |
| Primary hyperoxaluria type 1 | Disrupted breakdown of glyoxylate leading to renal damage | AGXT, GRHPR, autosomal recessive |
| Progressive familial intrahepatic cholestasis | Buildup of bile acids in liver cells causing liver damage | ATP8B1, autosomal recessive |

TABLE 2-continued

Non-limiting examples of human genes and genetic disorders

| Disease | Pathology | Gene, heredity |
|---|---|---|
| Thrombocyte activity disorder | Lack of enzyme activity disrupts the usual balance between bleeding and clotting | ADAMTS13, autosomal recessive |
| Urea cycle disorders | Disorder of the urea cycle which causes a form of hyperammonemia | OTC (X-linked disorder), CPS1, ASS1 and SLC25A13, ASL, autosomal recessive |

The above Table 2 shows examples of genes in which a defect leads to a disease which can be treated with the RNA molecule of the present invention wherein the RNA molecule comprises a "coding region coding for a polypeptide" which encodes an intact version of the protein or a functional fragment thereof of the above disclosed defective gene. In particularly preferred embodiments, hereditary diseases can be mentioned which for example affect the lungs, such as SPB (surfactant protein B) deficiency, ABCA3 deficiency, cystic fibrosis and α1-antitrypsin deficiency, or which affect plasma proteins (e.g. congenital hemochromatosis (hepcidin deficiency), thrompotic thrombocytopenic purpura (TPP, ADAMTS 13 deficiency) and cause clotting defects (e.g. haemophilia a and b) and complement defects (e.g. protein C deficiency), immune defects such as for example SCID (caused my mutations in different genes such as: RAG1, RAG2, JAK3, IL7R, CD45, CD3δ, CD3ε) or by deficiencies due to lack of adenosine desaminase for example (ADA-SCID), septic granulomatosis (e.g. caused by mutations of the gp-91-phox gene, the p47-phox gene, the p67-phox gene or the p33-phox gene) and storage diseases like Gaucher's disease, Fabry's disease, Krabbe's disease, MPS I, MPS II (Hunter syndrome), MPS VI, Glycogen storage disease type II or muccopolysacchaidoses. Other disorders for which the present invention comprising a "coding region coding for a peptide" can be useful include disorders such as SMN1-related spinal muscular atrophy (SMA); amyotrophic lateral sclerosis (ALS); GALT-related galactosemia; Cystic Fibrosis (CF); SLC3A1-related disorders including cystinuria; COL4A5-related disorders including Alport syndrome; galactocerebrosidase deficiencies; X-linked adrenoleukodystrophy and adrenomyeloneuropathy; Friedreich's ataxia; Pelizaeus-Merzbacher disease; TSC1 and TSC2-related tuberous sclerosis; Sanfilippo B syndrome (MPS IIIB); CTNS-related cystinosis; the FMR1-related disorders which include Fragile X syndrome, Fragile X-Associated Tremor/Ataxia Syndrome and Fragile X Premature Ovarian Failure Syndrome; Prader-Willi syndrome; hereditary hemorrhagic telangiectasia (AT); Niemann-Pick disease Type C1; the neuronal ceroid lipofuscinoses-related diseases including Juvenile Neuronal Ceroid Lipofuscinosis (JNCL), Juvenile Batten disease, Santavuori-Haltia disease, Jansky-Bielschowsky disease, and PTT-1 and TPP1 deficiencies; EIF2B1, EIF2B2, EIF2B3, EIF2B4 and EIF2B5-related childhood ataxia with central nervous system hypomyelination/vanishing white matter; CACNA1A and CACNB4-related Episodic Ataxia Type 2; the MECP2-related disorders including Classic Rett Syndrome, MECP2-related Severe Neonatal Encephalopathy and PPM-X Syndrome; CDKL5-related Atypical Rett Syndrome; Kennedy's disease (SBMA); Notch-3 related cerebral autosomal dominant arteriopathy with subcortical infarcts and leukoencephalopathy (CADASIL); SCN1A and SCN1B-related seizure disorders; the Polymerase G-related disorders which include Alpers-Huttenlocher syndrome, POLG-related sensory ataxic neuropathy, dysarthria, and ophthalmoparesis, and autosomal dominant and recessive progressive external ophthalmoplegia with mitochondrial DNA deletions; X-Linked adrenal hypoplasia; X-linked agammaglobulinemia; Fabry disease; and Wilson's disease.

In all these diseases, a protein, e.g. an enzyme, is defective, which can be treated by treatment with the RNA according to the invention, which makes the protein encoded by the defective gene or a functional fragment thereof available. Transcript replacement therapies/enzyme replacement therapies do not affect the underlying genetic defect, but increase the concentration of the enzyme in which the patient is deficient. As an example, in Pompe's disease, the transcript replacement therapy/enzyme replacement therapy replaces the deficient Lysosomal enzyme acid alpha-glucosidase (GAA).

Thus, non-limiting examples of proteins which can be encoded by the "coding region coding for a polypeptide" of module (a) according to the invention are erythropoietin (EPO), growth hormone (somatotropin, hGH), cystic fibrosis transmembrane conductance regulator (CFTR), growth factors such as GM-SCF, G-CSF, MPS, protein C, hepcidin, ABCA3 and surfactant protein B. Further examples of diseases which can be treated with the RNA according to the invention are hemophilia A/B, Fabry's disease, CGD, ADAMTS13, Hurler's disease, X chromosome-mediated A-y-globulinemia, adenosine deaminase-related immunodeficiency and respiratory distress syndrome in the newborn, which is linked with SP-B. Particularly preferably, the "coding region coding for a polypeptide" of the RNA molecule according to the invention contains the sequence for surfactant protein B (SP-B) or for erythropoietin. Further examples of proteins which can be encoded by the "coding region coding for a polypeptide" of the RNA molecule according to the invention are growth factors such as human growth hormone hGH, BMP-2 or angiogenesis factors.

Alternatively the nucleic acids may encode full length antibodies or smaller antibodies (e.g., both heavy and light chains) to confer immunity to a subject. In another embodiment, the "coding region coding for a polypeptide" may encode a functional monoclonal or polyclonal antibody, which may be useful for targeting and/or inactivating a biological target (e.g., a stimulatory cytokine such as tumor necrosis factor). Similarly, the "coding region coding for a polypeptide" may encode, for example, functional antinephrotic factor antibodies useful for the treatment of membranoproliferative glomerulonephritis type II or acute hemolytic uremic syndrome, or alternatively may encode antivascular endothelial growth factor (VEGF) antibodies useful for the treatment of VEGF-mediated diseases, such as cancer.

Module (a), i.e., the "coding region including a start codon at its 5' end coding for a polypeptide", may be a coding region encoding a polypeptide or a protein which can be used in genome editing technologies. Genome editing is a type of genetic engineering in which DNA is inserted, deleted or replaced in the genome of an organism using nucleases. These nucleases create site-specific breaks at desired locations in the genome. The induced breaks are repaired by non-homologous end-joining or homologous recombination, resulting in targeted mutations in the genome, thereby "editing" the genome. The breaks may either be single-strand breaks or double-strand breaks (DSBs) while double-strand breaks (DSBs) are preferred. Numerous genome editing systems utilizing different polypeptides or proteins are known in the art, i.e., e.g., the CRISPR-Cas system, meganucleases, zinc finger nucleases (ZFNs) and transcription activator-like effector-based nucleases (TALEN). Methods for genome engineering are reviewed in Trends in Biotechnology, 2013, 31 (7), 397-405.

Thus, in a preferred embodiment, the "coding region including a start codon at its 5' end coding for a polypeptide" contains a nucleotide sequence which encodes a polypeptide or protein of the Cas (CRISPR associated protein) protein family, preferably Cas9 (CRISPR associated protein 9). Proteins of the Cas protein family, preferably Cas9, may be used in CRISPR/Cas9 based methods and/or CRISPR/Cas9 genome editing technologies. CRISPR-Cas systems for genome editing, regulation and targeting are reviewed in Nat. Biotechnol., 2014, 32(4):347-355.

In another preferred embodiment, the "coding region including a start codon at its 5' end coding for a polypeptide" contains a nucleotide sequence which encodes a meganuclease. Meganucleases are endodeoxyribonucleases which, in contrast to "conventional" endodeoxyribonucleases, recognize a large recognition site (e.g., a double-stranded DNA sequence of 12 to 40 base pairs). As a result, the respective site occurs only few times, preferably only once, in any given genome. Meganucleases are therefore considered to be the most specific naturally occurring restriction enzymes and, accordingly, are suitable tools in genome editing technologies.

In another preferred embodiment, the "coding region including a start codon at its 5' end coding for a polypeptide" contains a nucleotide sequence which encodes a zinc finger nuclease (ZFN). ZFNs are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of the endogenous DNA repair machinery, ZFNs can be used to precisely alter the genome of higher organisms and are, therefore, suitable tools in genome editing technologies.

In another preferred embodiment, the "coding region including a start codon at its 5' end coding for a polypeptide" contains a nucleotide sequence which encodes a transcription activator-like effector nuclease (TALEN). TALENs are restriction enzymes that can be engineered to cut specific sequences of DNA. TALENs are fusion proteins wherein a TAL effector DNA-binding domain is fused to a DNA cleavage domain of a nuclease. Transcription activator-like effectors (TALEs) can be engineered to bind practically any desired DNA sequence. Thus, when combined with a nuclease, DNA can be cut at specific desired locations.

The second module (b) is the one or more UTR(s) comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1.

"One or more" in this context means that module (b) of the RNA molecule may harbor one UTR comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1 of the present invention. The RNA molecule may also harbor two, three or four of these UTRs of the present invention. Alternatively, the RNA molecule may also harbor five or even more of these UTRs of the present invention.

The third module (c) is the one or more UTR(s) comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2 (i.e., the above module (c)).

"One or more" in this context means that module (c) of the RNA molecule may harbor one UTR comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2 of the present invention. The RNA molecule may also harbor two, three or four of these UTRs of the present invention. Alternatively, the RNA molecule may also harbor five or even more of these UTRs of the present invention.

The full-length sequence of the native human cytochrome b-245 alpha polypeptide (CYBA) mRNA is known in the art and has the sequence as shown in SEQ ID NO:7. In the appended examples, the sequence from nucleotides 36 to 71 of the native human cytochrome b-245 alpha polypeptide (CYBA) mRNA has been used as the 5' UTR fragment of the CYBA mRNA (i.e., the nucleotide sequence 5'-CGCGCC-UAGCAGUGUCCCAGCCGGGUUCGUGUCGCC-3' (SEQ ID NO:1)) and the sequence from nucleotides 657 to 723 of the native human cytochrome b-245 alpha polypeptide (CYBA) mRNA has been used as the 3' UTR of the CYBA mRNA (i.e., the nucleotide sequence 5'-CCUCGCCCCGGACCUGCCCUCCCGCCAGGUGC-ACCC ACCUGCAAUAAAUGCAGCGAAGCCGGGA-3' (SEQ ID NO:2)).

However, the UTRs as used in the present invention are not particularly limited to the above specific sequence of SEQ ID NO:1 but may also be a UTR sequence which comprises a sequence which shows 1 to 4 substitutions in comparison to SEQ ID NO:1. Alternatively, the UTR sequence may also be a sequence which comprises a sequence which shows 1 to 3 substitutions in comparison to SEQ ID NO:1. The UTR sequence may also be a sequence which comprises a sequence which shows 1 to 2 substitutions in comparison to SEQ ID NO:1. Most preferably, the UTR sequence may also be a sequence which comprises a sequence which shows 1 substitution, in comparison to SEQ ID NO:1.

Preferably, the position of the above nucleotide substitution in comparison to SEQ ID NO:1 is performed at position 32 in the sequence of SEQ ID NO:1. Preferably, the nucleotide "U" at this position is substituted by a "C". This substitution is preferred since it brings the Kozak element of CYBA which is (partially) present in SEQ ID NO:1 closer to the Kozak consensus sequence of vertebrates. The Kozak consensus sequence of vertebrates has the sequence of GCCRCCAUGG (the start codon is underlined while "R" indicates any purine) while the Kozak element of CYBA has the sequence of GuCGCCAUGG (the start codon is underlined while the deviation from the vertebrate consensus sequence is indicated by the lower case letter "u").

The UTR sequence(s) which have one or more of the above substitutions in comparison to SEQ ID NO:1 may result in an RNA molecule in the same or similar capability in terms of the translation efficiency as an RNA molecule comprising an UTR comprising SEQ ID NO:1, preferably a higher capability in terms of the translation efficiency as an RNA molecule comprising an UTR comprising SEQ ID NO:1. The property/capability of a given modified UTR sequence in comparison to in terms of the translation efficiency as an RNA molecule comprising an UTR comprising SEQ ID NO:1 with respect to the translation efficiency can be determined by the skilled person by methods known in the art and as outlined in the appended examples.

The translation efficiency is the rate of mRNA translation into polypeptides or proteins within cells. The translation efficiency of a given mRNA is measured as the number of proteins or polypeptides which are translated per mRNA per time unit. Translation is the process in which cellular ribosomes create proteins and is well-known to the skilled person. Briefly, in translation, messenger RNA (mRNA) which is produced by transcription from DNA is decoded by a ribosome to produce a specific amino acid chain or a polypeptide or a protein.

Thus, the translation efficiency of a given RNA molecule harboring a modified UTR sequence is preferably higher in comparison to a translation efficiency of the same given RNA but harboring an UTR of SEQ ID NO:1. Accordingly, the number of proteins or polypeptides encoded by the coding region of the RNA molecule harboring a modified UTR sequence which are translated per RNA per time unit is higher than the number of proteins or polypeptides encoded by the coding region of the RNA molecule harboring an UTR of SEQ ID NO:1 which are translated per RNA per time unit.

In case the translation efficiency of a given RNA molecule harboring a modified UTR sequence is similar or the same in comparison to a translation efficiency of the same given RNA but harboring an UTR of SEQ ID NO:1, the number of proteins or polypeptides encoded by the coding region of the RNA molecule harboring a modified UTR sequence which are translated per RNA per time unit is similar to or the same as the number of proteins or polypeptides encoded by the coding region of the RNA molecule harboring an UTR of SEQ ID NO:1 which are translated per RNA per time unit.

The "translation efficiency" can, e.g., be determined by methods described in the appended examples and as outlined in the following.

Translation efficiency, in the context of the present invention, is the rate of mRNA translated into protein within a cell at a certain time point in relation to the amount of mRNA encoding the respective protein in said cell at the same time point. Thus, the translation efficiency is the quotient of the mRNA translated into protein within a cell at a certain time point and the amount of mRNA encoding the respective protein. Both parameters, i.e., the mRNA translated into a protein as well as the amount of mRNA encoding the respective protein, can be determined by methods known in the art. As it has been done in the appended examples, as non-limiting examples, the amount of mRNA translated into protein within a cell can, e.g., be determined by as determined by flow cytometry (FC) while the amount of mRNA encoding the respective protein can, e.g., be measured by qPCR.

The UTR(s) comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1 as used in the present invention is/are not particularly limited to the above specific sequences and the above described substitutions but may also relate to (an) UTR sequence(s) which comprise(s) a sequence which shows (a) nucleotide(s) addition(s) in comparison to SEQ ID NO:1. The addition of (a) nucleotide(s) can be flanking. Thus, the additional nucleotide(s) may be added at the 3'-end or 5'-end of the UTR(s) of the present invention. The additional nucleotide(s) comprise polynucleotide chains of up to 0 (no changes), 1, 2, 3, 4, 5, 6, 7, 8, 9 or 10 nucleotides, preferably of up to 20 nucleotides or even more preferably of up to 30 nucleotides. In light of the rationale that the addition of nucleotides is likely not to change the above functional properties of the UTR(s) of the invention the addition of the nucleotides may also have a length of up to 40, 50, 60, 70, 80, 90, or even 100 nucleotides or even more, up to 200, 300, 400 or 500 nucleotides as long as these sequences have a similar capability (in terms of the above-described translation efficiency) as SEQ ID NO:1, preferably higher translation efficiency as SEQ ID NO:1 as defined above.

Alternatively, or in addition to these flanking additions of (a) nucleotide(s) the addition of (a) nucleotide(s) can be interspersed. Thus, the additional nucleotide(s) may be added/inserted within the nucleotide sequence of the UTR(s) of the present invention. These nucleotide(s) insertions comprise 1, 2, or 3 nucleotides as long as these sequences have a similar capability (in terms of the above-described translation efficiency) as SEQ ID NO:1, preferably higher translation efficiency as SEQ ID NO:1 as defined above.

The UTRs as used in the present invention are not particularly limited to the above specific sequence of SEQ ID NO:1 and modifications thereof. Rather, the specific sequence of SEQ ID NO:1 and modifications thereof merely define the CYBA 5' core region. Thus, in a preferred embodiment, the UTR as shown in SEQ ID NO:1 is extended on the 5' end (i.e., upstream) by at least 1 nucleotide. In another preferred embodiment, the UTR as shown in SEQ ID NO:1 is extended on the 5' end (i.e., upstream) by 1 to 20 nucleotides. Hence, in a preferred embodiment, the sequence of SEQ ID NO:1 extends by 20 nucleotides on the 5' end (i.e., upstream) as shown in the nucleotide sequence of SEQ ID NO:10 (or the corresponding RNA sequence of SEQ ID NO:11) vis-à-vis SEQ ID NO:1. In other preferred embodiments, the sequence of SEQ ID NO:1 extends by 18, 15, 13, 10, 7 or 5 nucleotides on the 5' end (i.e., upstream) as shown in the nucleotide sequence of SEQ ID NO:10 (or the corresponding RNA sequence of SEQ ID NO:11) vis-à-vis SEQ ID NO:1. In other preferred embodiments, the sequence of SEQ ID NO:1 extends by 4, 5 or 2 nucleotides on the 5' end (i.e., upstream) as shown in the nucleotide sequence of SEQ ID NO:10 (or the corresponding RNA sequence of SEQ ID NO:11) vis-à-vis SEQ ID NO:1. In other preferred embodiment, the sequence of SEQ ID NO:1 extends by 1 nucleotide on the 5' end (i.e., upstream) as shown in the nucleotide sequence of SEQ ID NO:10 (or the corresponding RNA sequence of SEQ ID NO:11) vis-à-vis SEQ ID NO:1.

SEQ ID NO:10 is a part of the genetic code of the human CYBA gene 5'UTR shown above as SEQ ID NO:5 (as defined on the DNA-level) while SEQ ID NO:11 is the corresponding RNA sequence.

These UTR sequences which are extended on the 5' end (i.e., upstream) may also be modified as defined herein above for SEQ ID NO:1. Accordingly, the same applies, mutatis mutandis, to the UTRs which are extended on the 5' end as defined above as has been set forth above in the context of the UTR of SEQ ID NO:1.

Moreover, the UTRs as used in the present invention are also not particularly limited to the above specific sequence of SEQ ID NO:2 but may also be a UTR sequence which comprises a sequence which shows 1 to 7 substitutions in comparison to SEQ ID NO:2. Alternatively, the UTR sequence may also be a sequence which comprises a sequence which shows 1 to 6 substitutions in comparison to SEQ ID NO:2. The UTR sequence may also be a sequence which comprises a sequence which shows 1 to 5 substitutions in comparison to SEQ ID NO:2. The UTR sequence may also be a sequence which comprises a sequence which shows 1 to 4 substitutions in comparison to SEQ ID NO:2. The UTR sequence may also be a sequence which comprises a sequence which shows 1 to 3 substitutions in comparison to SEQ ID NO:2. The UTR sequence may also be a sequence which comprises a sequence which shows 1 to 2 substitutions in comparison to SEQ ID NO:2. The UTR sequence may also be a sequence which comprises a sequence which shows 1 to 3 substitutions in comparison to SEQ ID NO:2. Most preferably, the UTR sequence may also be a sequence which comprises a sequence which shows 1 substitution, in comparison to SEQ ID NO:2.

The UTR sequence(s) which have one or more of the above substitutions in comparison to SEQ ID NO:2 may result in an RNA molecule in the same or similar capability in terms of the translation efficiency as an RNA molecule comprising an UTR comprising SEQ ID NO:2, preferably a higher capability in terms of the translation efficiency as an RNA molecule comprising an UTR comprising SEQ ID NO:2. The property/capability of a given modified UTR sequence in comparison to in terms of the translation efficiency as an RNA molecule comprising an UTR comprising SEQ ID NO:2 with respect to the translation efficiency can be determined by the skilled person by methods known in the art and as outlined in the appended examples.

The translation efficiency is the rate of mRNA translation into polypeptides or proteins within cells. The translation efficiency of a given mRNA is measured as the number of proteins or polypeptides which are translated per mRNA per time unit. Translation is the process in which cellular ribosomes create proteins and is well-known to the skilled person. Briefly, in translation, messenger RNA (mRNA) which is produced by transcription from DNA is decoded by a ribosome to produce a specific amino acid chain or a polypeptide or a protein.

Thus, the translation efficiency of a given RNA molecule harboring a modified UTR sequence is preferably higher in comparison to a translation efficiency of the same given RNA but harboring an UTR of SEQ ID NO:2. Accordingly, the number of proteins or polypeptides encoded by the coding region of the RNA molecule harboring a modified UTR sequence which are translated per RNA per time unit is higher than the number of proteins or polypeptides encoded by the coding region of the RNA molecule harboring an UTR of SEQ ID NO:2 which are translated per RNA per time unit.

In case the translation efficiency of a given RNA molecule harboring a modified UTR sequence is similar or the same in comparison to a translation efficiency of the same given RNA but harboring an UTR of SEQ ID NO:2, the number of proteins or polypeptides encoded by the coding region of the RNA molecule harboring a modified UTR sequence which are translated per RNA per time unit is similar to or the same as the number of proteins or polypeptides encoded by the coding region of the RNA molecule harboring an UTR of SEQ ID NO:2 which are translated per RNA per time unit.

The "translation efficiency" can, e.g., be determined by methods described in the appended examples and as outlined above.

The UTR(s) comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2 as used in the present invention is/are not particularly limited to the above specific sequences and the above described substitutions but may also relate to (an) UTR sequence(s) which comprise(s) a sequence which shows (a) nucleotide(s) addition(s) in comparison to SEQ ID NO:2. The addition of nucleotide(s) can be flanking or interspersed. Thus, the additional nucleotide(s) may be added at the 3'-end or 5'-end of the UTR(s) of the present invention. Alternatively, or in addition to these flanking additional nucleotide(s), the additional nucleotide(s) may also be within the nucleotide sequence of the UTR(s) of the present invention. The additional nucleotide(s) comprise polynucleotide chains of up to 0 (no changes), 1, 2, 3, 4, 5, 6, 7, 8, 9 or 10 nucleotides, preferably of up to 20 nucleotides or even more preferably of up to 30 nucleotides. In light of the rationale that the addition of nucleotides is likely not to change the above functional properties of the UTR(s) of the invention the addition of the nucleotides may also have a length of up to 40, 50, 60, 70, 80, 90, or even 100 nucleotides or even more, up to 200, 300, 400 or 500 nucleotides as long as these sequences have a similar capability (in terms of the above-described translation efficiency) as SEQ ID NO:2, preferably higher translation efficiency as SEQ ID NO:2 as defined above.

The UTR(s) of the present invention as well as RNA molecules containing such UTR(s) may be recombinantly (e.g., in an in vivo or an in vitro system) or synthetically generated/synthesized by methods known to the person skilled in the art.

More specifically, the UTRs of the present invention and RNA molecules containing such UTR(s) may be produced either recombinantly in in vivo systems by methods known to the person skilled in the art.

Alternatively, the UTRs of the present invention and RNA molecules containing such UTR(s) may be produced in an in vitro system using, for example, an in vitro transcription system. In vitro transcription systems are commonly known and usually require a purified linear DNA template containing a DNA sequence "encoding" module (b) and/or module (c) as outlined in detail further below wherein said DNA sequence is under the control of an appropriate promoter. Moreover, an in vitro transcription system also commonly requires ribonucleoside triphosphates, a buffer system that includes DTT and magnesium ions, and an appropriate RNA polymerase which provides the enzymatic activity for the in vitro transcription of the DNA sequence "encoding" the modules (b) and/or (c) into the UTR(s) of the present invention.

Furthermore, the UTRs of the present invention and RNA molecules containing such UTR(s) may be chemically synthesized, e.g., by conventional chemical synthesis on an automated nucleotide sequence synthesizer using a solid-phase support and standard techniques or by chemical synthesis of the respective DNA-sequences and subsequent in vitro or in vivo transcription of the same.

In accordance with the above, the present invention provides RNA molecules/polyribonucleic acid molecules, preferably modified polyribonucleic acid molecules, wherein one module of said RNA molecule, i.e., "a coding region including a start codon at its 5' end" (module (a)), encodes for a polypeptide. The terms nucleic acid and polynucleotide are used interchangeably and include any compound and/or substance that comprises a polymer of nucleotides. The term nucleotide includes deoxynucleotides and ribonucleotides. The terms ribonucleic acid and polyribonucleotide are used interchangeably and, in certain embodiments, include any compound and/or substance that comprises a polymer of nucleotides wherein greater than 50% of the nucleotides are ribonucleotides. In certain embodiments, polyribonucleotides comprise a polymer of nucleotides wherein greater than 60%, 70%, 75%, 80%, 90%, greater than 95%, greater than 99% or 100% of the nucleotides are ribonucleotides. Polyribonucleotides wherein one or more nucleotides are modified nucleotides may be referred to as modified polyribonucleotides. However, the term polyribonucleotides may include modified polyribonucleotides.

The sequence of the RNA molecules/polyribonucleotides can be derived from, for example, any suitable nucleic acid that comprises the genetic information of a gene of interest. Examples of nucleic acids include genomic DNA, RNA, or cDNA from any bacterial or archaeal cell comprising the gene(s) of interest. The polynucleotides can be derived from nucleic acids carrying mutated genes and polymorphisms. An RNA molecule/polyribonucleotide of the present invention comprises a sequence which is not particularly limited and may comprise, as module A, any desired coding region which is expressed in a given cell. In a preferred embodiment, said sequence may be a coding region coding for a desired polypeptide/protein as outlined above. Preferably, in line with the above, the RNA molecule/polyribonucleotide further comprises an untranslated sequence positioned upstream (5') of the module A's start codon, an untranslated sequence positioned downstream (3') of module A's stop codon, or both an untranslated sequence positioned upstream (5') of module A's start codon and an untranslated sequence positioned downstream (3') of module A's stop codon. In a preferred embodiment, an RNA molecule/polyribonucleotide of the present invention may be a modified RNA molecule/polyribonucleotide.

In addition to the four classical ribonucleotides, namely, adenosine, guanosine, cytidine and uridine, there exist numerous analogs of each of these nucleobases. Sometimes throughout and in the literature, these analogs, or RNA molecules/polyribonucleotides that include one or more of these analogs, are referred to as modified (e.g., modified nucleotides or modified ribonucleotides). Some analogs differ from the above canonical nucleobases, but yet can exist in nature. Other analogs are non-naturally occurring. Either type of analog is contemplated.

In certain embodiments, RNA molecules/polyribonucleotides of the present invention comprise nucleotide analogs (e.g., the polyribonucleotide comprises a modified polyribonucleotide). Exemplary nucleotide analogs are provided below (e.g., analogs of U; analogs of C; analogs of A; analogs of G). In addition, in certain embodiments, an RNA molecule/polyribonucleotide or other nucleic acid of the disclosure may also comprise (in addition to or alternatively) modifications in the phosphodiester backbone or in the linkage between nucleobases. Exemplary nucleic acids that can form part or all of an RNA molecule/polyribonucleotide of the disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a beta-D-ribo configuration, alpha-LNA having an alpha-L-ribo configuration (a diastereomer of LNA), 2'-amino-LNA having a 2'-amino functionalization, and 2'-amino-alpha-LNA having a 2'-amino functionalization) or hybrids thereof.

In certain embodiments, a modification may be on one or more nucleoside(s) or the backbone of the nucleic acid/polynucleotide molecule. In certain embodiments, a modification may be on both a nucleoside and a backbone linkage. In certain embodiments, a modification may be engineered into a polynucleotide in vitro. In certain embodiments, a modified ribonucleotide/nucleotide may also be synthesized post-transcriptionally by covalent modification of the classical/natural nucleotides/ribonucleotides.

An RNA molecule/polyribonucleotide of the present invention can be a modified RNA molecule/polyribonucleotide and, in certain embodiments, can comprise analogs of purines and/or analogs of pyrimidines. In certain embodiments, a modified RNA molecule/polyribonucleotide of the present invention comprises a pyrimidine analog, such as an analog of uridine and/or an analog of cytidine. In certain embodiments, a modified RNA molecule/polyribonucleotide of the present invention comprises an analog of uridine and an analog of cytidine. In certain embodiments, the modified RNA molecule/polyribonucleotide does not comprise analogs of adenosine and/or analogs of guanosine. In certain embodiments, the RNA molecule/polyribonucleotide comprises a single type of analog of uridine and a single type of analog of cytidine (e.g., one type of analog, not a single molecule of analog—the single analog may be present at any of several percentages described herein). In other embodiments, the RNA molecule/polyribonucleotide comprises more than one type of analog of uridine and/or cytidine and, optionally and if present, one or more analogs of adenosine and/or guanosine (or none of either or both).

In some cases a modified uridine (e.g., analog of uridine) is selected from 2-thiouridine, 5'-methyluridine, pseudouridine, 5-iodouridine (I5U), 4-thiouridine (S4U), 5-bromouridine (Br5U), 2'-methyl-2'-deoxyuridine (U2'm), 2'-amino-2'-deoxyuridine (U2'NH$_2$), 2'-azido-2'-deoxyuridine (U2N$_3$), and 2'-fluoro-2'-deoxyuridine (U2'F). In some cases, a modified cytidine (e.g., analog of cytidine) is selected from 5-methylcytidine, 3-methylcytidine, 2-thiocytidine, 2'-methyl-2'-deoxycytidine (C2'm), 2'-amino-2'-deoxycytidine (C2'NH2), 2'-fluoro-2'-deoxycytidine (C2'F), 5-iodocytidine (I5C), 5-bromocytidine (Br5C) and 2'-azido-2'-deoxycytidine (C2'N3). Note that when referring to analogs, the foregoing also refers to analogs in their 5' triphosphate form. In certain embodiments, the cytidine analog is 5-iodocytidine and the uridine analog is 5-iodouridine.

In some embodiments, the RNA molecule/polyribonucleotide is a modified RNA molecule/polyribonucleotide. In some cases, the modified RNA molecule/polyribonucleotide is at least 25% more stable as compared to a non-modified (or unmodified) RNA molecule/polyribonucleotide. In some cases, the modified RNA molecule/polyribonucleotide can be at least 30% more stable, at least 35% more stable, at least 40% more stable, at least 45% more stable, at least 50% more stable, at least 55% more stable, at least 60% more stable, at least 65% more stable, at least 70% more stable, at least 75% more stable, at least 80% more stable, at least 85% more stable, at least 90% more stable, or at least 95% more stable as compared to a non-modified RNA molecule/polyribonucleotide. In certain embodiments, stability is measured in vivo. In certain embodiments, stability is measured in vitro. In certain embodiments, stability is quantified by measuring the half-life of the polyribonucleotide.

A RNA molecule/polyribonucleotide of the present invention can have nucleotides that have been modified in the same form or else a mixture of different modified nucleotides. The modified nucleotides can have modifications that are naturally or not naturally occurring in messenger RNA. A mixture of various modified nucleotides can be used. For example one or more modified nucleotides within an RNA molecule/polyribonucleotide can have natural modifications, while another part has modifications that are not naturally found in mRNA. Additionally, some modified nucleotides can have a base modification, while other modified nucleotides have a sugar modification. In the same way, it is possible that all modifications are base modifications or all modifications are sugar modifications or any suitable mixture thereof. In some cases, the stability of the modified RNA molecule/polyribonucleotide can be selectively optimized by changing the nature of modified bases within the modified polyribonucleotide.

TABLE 2

Non-limiting examples of analogs of U

| Name | Base modification (5'-position) | Sugar modification (2'-position) | Naturally in mRNA |
|---|---|---|---|
| 5-methyluridine (m5U) | CH$_3$ | — | No |
| 5-iodouridine (I5U) | I | — | No |
| 5-bromouridine (Br5U) | Br | — | No |
| 2-thiouridine (S2U) | S (in 2 position) | — | No |
| 4-thiouridine (S4U) | S (in 4 position) | — | No |
| 2'-methyl-2'-deoxyuridine (U2'm) | — | CH$_3$ | Yes |
| 2'-amino-2'-deoxyuridine (U2'NH2) | — | NH$_2$ | No |
| 2'-azido-2'-deoxyuridine (U2'N3) | — | N$_3$ | No |
| 2'-fluoro-2'-deoxyuridine (U2'F) | — | F | No |

TABLE 3

Non-limiting examples of analogs of C

| Name | Base modification (5'-position) | Sugar modification (2'-position) | Naturally in mRNA |
|---|---|---|---|
| 5-methylcytidine (m5C) | CH$_3$ | — | Yes |
| 5-iodocytidine (I5C) | I | — | No |
| 5-bromocytidine (Br5C) | Br | — | No |
| 2-thiocytidine (S2C) | S (in 2 position) | — | No |
| 2'-methyl-2'-deoxycytidine (C2'm) | — | CH$_3$ | Yes |
| 2'-amino-2'-deoxycytidine (C2'NH2) | — | NH$_2$ | No |
| 2'-azido-2'-deoxycytidine (C2'N3) | — | N$_3$ | No |
| 2'-fluoro-2'-deoxycytidine (C2'F) | — | F | No |

TABLE 4

Non-limiting examples of analogs of A

| Name | Base modification (5'-position) | Sugar modification (2'-position) | Naturally in mRNA |
|---|---|---|---|
| N6-methyladenosine (m6A) | CH$_3$ (in 6 position) | — | Yes |
| N1-methyladenosine (m1A) | CH$_3$ (in 1 position) | — | No |
| 2'-0-methyladenosine (A2'm) | — | CH$_3$ | Yes |
| 2'-amino-2'-deoxyadenosine (A2'NH2) | — | NH$_2$ | No |
| 2'-azido-2'-deoxyadenosine (A2'N3) | — | N$_3$ | No |
| 2'-fluoro-2'-deoxyadenosine (A2'F) | — | F | No |

TABLE 5

Non-limiting examples of analogs of G

| Name | Base modification (5'-position) | Sugar modification (2'-position) | Naturally in mRNA |
|---|---|---|---|
| N1-methylguanosine (m1G) | CH$_3$ (in position 1) | — | No |
| 2'-0-methylguanosine (G2'm) | — | CH$_3$ | Yes |
| 2'-amino-3'-deoxyguanosine (G2'NH2) | — | NH$_2$ | No |
| 2'-azido-2'-deoxyguanosine (G2'N3) | — | N$_3$ | No |
| 2'-fluoro-2'-deoxyguanosine (G2'F) | — | F | No |

In certain embodiments, an analog (e.g., a modified nucleotide) can be selected from the group comprising pyridin-4-one ribonucleoside, 5-iodouridine, 5-iodocytidine, 5-aza-uridine, 2'-amino-2'-deoxycytidine, 2'-fluor-2'-deoxycytidine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-I-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-d ihydropseudouridine, 2-methoxyuridine, 2-methoxy-4-thio-uridine, 4-methoxy-pseudouridine, 4-methoxy-2-thiopseudouridine, 5-aza-cytidine, pseudoisocytidine, 3-methylcytidine, N4-acetylcytidine, 5-formylcytidine, 5-methylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-I-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In certain embodiments, a modified RNA molecule/polyribonucleotide of the present invention does not include pseudouridine. In certain embodiments, a modified RNA molecule/polyribonucleotide of the present invention does not include 5-methyl cytidine. In certain embodiments, a modified RNA molecule/polyribonucleotide of the present invention does not include 5-methyl uridine. In certain embodiments, a modified RNA molecule/polyribonucleotide of the present invention comprises analogs of U and analogs of C, wherein such analogs of U may all be the same analog or may be different analogs (e.g., more than one type of analog), and wherein such analogs of C may all be the same analog or may be different analogs (e.g., more than one type of analog). In certain embodiments, a modified RNA molecule/polyribonucleotide of the present invention does not include analogs of adenosine and analogs of guanosine.

As described in detail herein, when an RNA molecule/polyribonucleotide comprises a modified polyribonucleotide, analogs may be present as a certain proportion of the nucleotides in the compound (e.g., a given percentage of a given nucleobase may be analog, as described herein).

An RNA molecule/polyribonucleotide that comprises at least one modified nucleotide is a modified RNA molecule/polyribonucleotide. In certain embodiments, at least about 5% of the modified RNA molecule/polyribonucleotide includes modified or non-naturally occurring (e.g., analogs of or modified) adenosine, cytidine, guanosine, or uridine, such as the analog nucleotides described herein. In some cases, at least about 5%, 10%, 15%, 20%, 25%, 30%, 40%, 45%, 50% of the modified RNA molecule/polyribonucleotide includes modified or non-naturally occurring (e.g., analogs of or modified) adenosine, cytidine, guanosine, or uridine. In some cases, at most about 50%, 45%, 40%, 35%, 30%, 25%, 20%, 15%, 10%, 5%, 1%, of the modified RNA molecule/polyribonucleotide includes modified or non-naturally occurring adenosine, cytidine, guanosine, or uridine.

In a preferred embodiment the RNA molecule of the present invention contains a combination of modified and unmodified nucleotides. Preferably, the RNA molecule of the present invention contains a combination of modified and unmodified nucleotides as described in WO 2011/012316. Such RNA molecules are also known and commercialized as "SNIM®-RNA". The RNA molecule described in WO 2011/012316 is reported to show an increased stability and diminished immunogenicity. In a preferred embodiment, in such a modified RNA molecule 5 to 50% of the cytidine nucleotides and 5 to 50% of the uridine nucleotides are modified. The adenosine- and guanosine-containing nucleotides can be unmodified. The adenosine and guanosine nucleotides can be unmodified or partially modified, and they are preferably present in unmodified form. Preferably 10 to 35% of the cytidine and uridine nucleotides are modified and particularly preferably the content of the modified cytidine nucleotides lies in a range from 7.5 to 25% and the content of the modified uridine nucleotides in a range from 7.5 to 25%. It has been found that in fact a relatively low content, e.g. only 10% each, of modified cytidine and uridine nucleotides can achieve the desired properties. It is particularly preferred that the modified cytidine nucleotides are 5-methylcytidine residues and the modified uridine nucleotides are 2-thiouridine residues. Most preferably, the content of modified cytidine nucleotides and the content of the modified uridine nucleotides is 25%, respectively.

In certain other embodiments, in such a modified RNA molecule/polyribonucleotide molecule, 5 to 50% of the cytidines are analogs of C and 5 to 50% of the uridines are analogs of U. In certain embodiments, in such a modified polyribonucleotide molecule 5 to 40% of the cytidines are analogs of C and 5 to 40% of the uridines are analogs of U. In certain embodiments, in such a modified RNA molecule/polyribonucleotide molecule 5 to 30% of the cytidines are analogs of C and 5 to 30% of the uridines are analogs of U. In certain embodiments, in such a modified RNA molecule/polyribonucleotide molecule 10 to 30% of the cytidines are analogs of C and 10 to 30% of the uridines are analogs of U. In certain embodiments, in such a modified polyribonucleotide molecule 5 to 20% of the cytidines are analogs of C and 5 to 20% of the uridines are analogs of U. In certain embodiments, in such a modified RNA molecule/polyribonucleotide molecule 5 to 10% of the cytidine nucleotides and 5 to 10% of the uridine nucleotides are modified. In certain embodiments, in such a modified RNA molecule/polyribonucleotide molecule 25% of the cytidine nucleotides and 25% of the uridine nucleotides are modified. In certain embodiments, the adenosine- and guanosine-containing nucleotides can be unmodified. In certain embodiments, the adenosine and guanosine nucleotides can be unmodified or partially modified, and they are preferably present in unmodified form.

As noted above, in certain embodiments, analogs of U refers to a single type of analog of U. In certain embodiments, analogs of U refers to two or more types of analogs of U. In certain embodiments, analogs of C refers to a single type of analog of C. In certain embodiments, analogs of C refers to two or more types of analogs of C.

In certain embodiments, the percentage of cytidines in an RNA molecule/polyribonucleotide that are analogs of cytidine is not the same as the percentage of uridines in the RNA molecule/polyribonucleotide that are analogs of uridine. In certain embodiments, the percentage of analogs of cytidine is lower than the percentage of analogs of uridine. As noted above, this may be in the presence or the absence of analogs of adenosine and guanosine but, in certain embodiments, is in the absence of analogs of adenosine and analogs of guanosine. In certain embodiments, polyribonucleotides of the disclosure comprises less than 15%, less than 10%, less than 5% or less than 2% analogs of adenosine, analogs of guanosine or both.

In certain embodiments, an RNA molecule/polyribonucleotide of the present inention comprises analogs of cytidine and analogs of uridine, and 5 to 20% of the cytidines are analogs of cytidine and 25 to 45% of the uridines are analogs of uridine. In other words, the RNA molecule/polyribonucleotide comprises modified and unmodified cytidines and modified and unmodified uridines, and 5 to 20% of the cytidines comprise analogs of cytidine while 25 to 45% of the uridines comprise analogs of uridine. In other embodiments, the RNA molecule/polyribonucleotide comprises 5 to 10% analogs of cytidine and 30 to 40% analogs of uridine, such as 7-9% analogs of cytidine, such as about 7, 7.5 or 8% and, such as 32-38% analogs of uridine, such as about 33, 34, 35, 36%.

In certain embodiments, any of the analogs of uridine and analogs of cytidine described herein may be used, optionally excluding pseudouridine. In certain embodiments, the analog of cytidine comprises or consists of (e.g., in the case of consists of, it is the single analog type used) 5-iodocytidine and the analog of uridine comprises or consists of (e.g., in the case of consists of, it is the single analog type used) 5-iodouridine.

In certain embodiments of any of the foregoing, the percentage of analogs of a given nucleotide refers to input percentage (e.g., the percentage of analogs in a starting reaction, such as a starting in vitro transcription reaction). In certain embodiments of any of the foregoing, the percentage of analogs of a given nucleotide refers to output (e.g., the percentage in a synthesized or transcribed compound).

The RNA molecules/polyribonucleotide molecules of the present invention may be produced recombinantly in in vivo systems by methods known to a person skilled in the art which are described in more detail furher below.

Alternatively, the modified polyribonucleotide molecules of the present invention may be produced in an in vitro system using, for example, an in vitro transcription system which is described in more detail further below. An in vitro transcription system capable of producing RNA molecules/polyribonucleotides requires an input mixture of modified and unmodified nucleoside triphosphates to produce modified RNA molecules/polyribonucleotides with the desired properties of the present invention. In certain embodiments, 5 to 50% of the cytidines are analogs of cytidine in such an input mixture and 5 to 50% of the uridines are analogs of uridine in such an input mixture. In certain embodiments, 5 to 40% of the cytidines are analogs of cytidine in such an input mixture and 5 to 40% of the uridines are analogs of uridine in such an input mixture. In certain embodiments, 5 to 30% of the cytidines are analogs of cytidine in such a mixture and 5 to 30% of the uridines are analogs of uridine in such an input mixture. In certain embodiments, 5 to 30% of the cytidines are analogs of cytidine in such mixture and 10 to 30% of the uridines are analogs of uridine in such mixture. In certain embodiments, 5 to 20% of the cytidines are analogs of cytidine in such an input mixture and 5 to 20% of the uridines are analogs of uridine in such an input mixture. In certain embodiments, 5 to 10% of the cytidines are analogs of cytidine in such an input mixture and 5 to 10% of the uridines are analogs of uridine in such an input mixture. In certain embodiments, 25% of the cytidines are analogs of cytidine in such an input mixture and 25% of the uridines are analogs of uridine in such an input mixture. In certain embodiments, the input mixture does not comprise analogs of adenosine and/or guanosine. In other embodiments, optionally, the input mixture comprises one or more analogs of adenosine and/or guanosine (or none of either or both).

In certain embodiments, the percentage of cytidines in an input mixture that are analogs of cytidine is not the same as the percentage of uridines in an input mixture that are analogs of uridine. In certain embodiments, the percentage of analogs of cytidine in an input mixture is lower than the percentage of analogs of uridine in an input mixture. As noted above, this may be in the presence or the absence of analogs of adenosine and guanosine in the input mixture but, in certain embodiments, is in the absence of analogs of adenosine and analogs of guanosine in the input mixture.

In certain embodiments, an input mixture of nucleotides for an in vitro transcription system that produces a RNA molecule/polyribonucleotide of the present invention comprises analogs of cytidine and analogs of uridine, and 5 to 20% of the cytidines of the input mixture are analogs of cytidine and and 25 to 45% of the uridines of the input mixture are analogs of uridine. In other words, the input mixture comprises modified and unmodified cytidines and modified and unmodified uridines, and 5 to 20% of the cytidines of the input mixture comprise analogs of cytidine while 25 to 45% of the uridines of the input mixture comprise analogs of uridine. In other embodiments, the input mixture comprises 5 to 10% analogs of cytidine and 30 to 40% analogs of uridine, such as 7-9% analogs of cytidine, such as 7, 7.5 or 8% and, such as 32-38% analogs of uridine, such as 33, 34, 35, 36%.

In certain embodiments, any of the analogs of uridine and analogs of cytidine described herein may be used, optionally excluding pseudouridine. In certain embodiments, the analog of cytidine comprises or consists of (e.g., it is the single C analog type used) 5-iodocytidine and the analog of uridine comprises or consists of (e.g., it is the single U analog type used) 5-iodouridine.

Exemplary analogs are described in the tables above. It should be understood that for modified polyribonucleotides encoding the desired polypeptide (module (a)), the analogs and level of modification is, unless indicated otherwise, considered across the entire polyribonucleotide encoding the desired polypeptide (module (a)), including 5' and 3' untranslated regions (e.g., the level of modification is based on input ratios of analogs in an in vitro transcription reaction such that analogs may be incorporated at positions that are transcribed).

Furthermore, the modified RNA molecules/polyribonucleotide molecules may be chemically synthesized, e.g., by conventional chemical synthesis on an automated nucleotide sequence synthesizer using a solid-phase support and standard techniques or by chemical synthesis of the respective DNA sequences and subsequent in vitro or in vivo transcription of the same.

In molecular biology and genetics, upstream and downstream both refer to a relative position in an RNA molecule. In the context of the present invention, upstream is toward the 5' end of the RNA molecule and downstream is toward the 3' end of the molecule.

Accordingly, in one embodiment, the UTR module (b) (i.e., the one or more UTR(s) comprising the sequence as shown in SEQ ID NO:1 or a sequence which has 1 to 4 substitutions in comparison to SEQ ID NO:1 and which results in an RNA molecule having the same or a higher translation efficiency as an RNA molecule comprising an UTR comprising SEQ ID NO:1 as defined hereinabove) is located upstream of the coding region of module (a). Moreover, in one embodiment, the UTR module (c) (i.e., the one or more UTR(s) comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2 as defined hereinabove) is located downstream of the coding region of module (a). Yet, preferably, the coding region coding for a polypeptide (i.e., module (a)) is located between the UTR module (b) and the UTR module (c) and, accordingly, the RNA molecule preferably has the arrangement of 5'-(b)-(a)-(c)-3'.

In case the RNA molecule only harbors one UTR module (i.e., either module (b) (i.e., the one or more UTR(s) comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1 as defined hereinabove) or module (c) (i.e., the one or more UTR(s) comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2 as defined hereinabove)) the RNA molecule preferably has the arrangement of 5'-(b)-(a)-3' or 5'-(a)-(c)-3'.

The RNA molecule may be present in the form of fused RNA sequences of modules (a), (b) and/or (c), i.e., a (fusion) RNA molecule which is formed by the expression of a hybrid gene made by combining at least two nucleotide sequences encoding said modules. Typically, as will be explained in more detail further below, this can be accomplished by cloning a cDNA into an expression vector which allows for the translation of the RNA molecule. Accordingly, the DNA molecule encoding the RNA molecule of the present invention may be a fused DNA sequence, i.e., a chimeric molecule which is formed by joining two or more polynucleotides via the phosphate group from one nucleotide bound to the 3' carbon on another nucleotide, forming a phosphodiester bond between the respective ends of one module and the end of another molecule. In this way, the above DNA molecules encoding said at least two modules, preferably all three modules are joined together in the form of a DNA molecule in terms of the present invention. Once cloned in frame, such a recombinant DNA molecule is then transcribed into its corresponding RNA nucleic acid sequence encoding said Protein, polypeptide or enzyme molecule.

Alternatively, the at least two modules, preferably all three modules may also be covalently coupled by a chemical conjugate. Thus, as will be outlined in more detail further below, the modules of the RNA molecule may be chemically synthesized individually and subsequently coupled in a covalent linkage by a phosphodiester bond as outlined above.

In the following, preferred arrangements of the UTR modules (b) and/or (c) of the present invention in relation to the coding region (a) are described wherein the UTR module (b) (corresponding to the above-defined 5' UTR fragment of the CYBA mRNA) is located upstream of the coding region (i.e., at the 5' end of the coding region) and/or the UTR module (c) (corresponding to the above-defined 3' UTR of the CYBA mRNA) is located downstream of the coding region (i.e., at the 3' end of the coding region).

Thus, in a preferred embodiment, and in accordance with the foregoing, the present invention relates to an RNA molecule comprising (a) a coding region coding for a polypeptide; and (b) one or more UTR(s) comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1, wherein said coding region coding for a polypeptide in (a) is not a coding region coding for a cytochrome b-245 alpha polypeptide (CYBA) as defined herein above and wherein said UTR(s) as defined in (b) is/are located at the 5' end of the coding region as defined in (a).

In a preferred embodiment, and in accordance with the foregoing, the present invention relates to an RNA molecule comprising (a) a coding region coding for a polypeptide; and (c) one or more UTR(s) comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2, wherein said coding region coding for a polypeptide in (a) is not a coding region coding for a cytochrome b-245 alpha polypeptide (CYBA) as defined herein above and wherein said UTR(s) as defined in (c) is/are located at the 3' end of the coding region as defined in (a).

In a preferred embodiment, and in accordance with the foregoing, the present invention relates to an RNA molecule comprising (a) a coding region coding for a polypeptide; and (b) one or more UTR(s) comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1; and (c) one or more UTR(s) comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2, wherein said coding region coding for a polypeptide in (a) is not a coding region coding for a cytochrome b-245 alpha polypeptide (CYBA) as defined herein above and wherein said UTR(s) as defined in (b) is/are located at the 5' end of the coding region as defined in (a) and wherein said UTR(s) as defined in (c) is/are located at the 3' end of the coding region as defined in (a).

In a preferred embodiment, and in accordance with the foregoing, the present invention relates to an RNA molecule comprising (a) a coding region coding for a polypeptide; and (b) one UTR comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1; and (c) two UTRs comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2; wherein said coding region coding for a polypeptide in (a) is not a coding region coding for a cytochrome b-245 alpha polypeptide (CYBA) as defined herein above and wherein said RNA molecule comprises said one UTR as defined in (b) at the 5' end of the coding region as defined in (a) and which comprises said two UTRs as defined in (c) at the 3' end of the coding region as defined in (a).

In a preferred embodiment, and in accordance with the foregoing, the present invention relates to an RNA molecule comprising (a) a coding region coding for a polypeptide; and (c) two UTRs comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2, wherein said coding region coding for a polypeptide in (a) is not a coding region coding for a cytochrome b-245 alpha polypeptide (CYBA) as defined herein above and wherein said RNA molecule comprises said two UTRs as defined in (c) at the 3' end of the coding region as defined in (a).

As mentioned above, the RNA molecule of the present invention may also harbor a poly-A tail. As used herein, a poly-A tail relates to a sequence of adenine nucleotides located at the 3' end of the RNA. A poly-A tail is commonly added to the 3' end of the RNA by a process called polyadenylation. Thus, the present invention relates to any of the above-described RNA, wherein the RNA molecule comprises a poly-A tail at the 3' end.

The length of the poly-A tail is not particularly limited. Yet, in preferred embodiments, the RNA molecule of the present invention comprises a poly-A tail at the 3' end wherein the poly-A tail has a length of at least 50, 60, 70, 80, 90, 100 or 110 nucleotides. In a more preferred embodiment, the RNA molecule of the present invention comprises a poly-A tail at the 3' end wherein the poly-A tail has a length of at least 120 nucleotides. In other preferred embodiments, the RNA molecule of the present invention comprises a poly-A tail at the 3' end wherein the poly-A tail has a length of at least 150, 200, 250, 300, 350, 400, 500, 600, 700, 800, 900 or 1000 nucleotides.

In case the RNA molecule of the present invention is produced by an in vitro transcription method as described herein further below the poly-A tail is located at the 3' end of the RNA adjacent to the UTR at the 3' end of the RNA construct while the plasmid harboring the RNA molecule of the present invention is linearized prior to the in vitro transcription downstream of the poly-A tail in order to assure that the in vitro transcribed RNA molecule contains said poly-A tail.

The construct according to the present invention may not only comprise the above three main modules (a), (b) and/or (c). Rather, it may be desirable that between the individual modules (a) linker moiety/moieties and/or (a) multiple cloning site(s) is/are placed which may, e.g., facilitate the construction of the construct. Suitable linker moieties and multiple cloning sites are known to the skilled person.

Preferably, the construct of the present invention harbors a multiple cloning site which is derived from the plasmid pVAX1 (Invitrogen). All the constructs as outlined in the Example section originate from the construct pVAX A120 which has previously been described in WO2013/182683 A1.

The position of the UTR modules (b) and/or (c) within the RNA molecule of the present invention in relation to module (a) (i.e., the coding region), is not particularly limited and, accordingly, between the individual modules of the RNA molecule of the present invention there may be a spacing or a gap filled with one or more nucleotides G, A, U and/or C which are not part of the main modules (a), (b) and/or (c).

"One or more nucleotides G, A, U and/or C" in this context means that the spacing or gap between the individual modules of the RNA molecule of the present invention is/are filled with 1, 2, 3, 4, 5, 6, 7, 8, 9 or 10 nucleotides G, A, U and/or C. In other preferred embodiments, the spacing or gap between the individual modules of the RNA molecule of the present invention are filled with 20, 30, 40, 50, 60, 70, 80, 90, 100 or 110 or more nucleotides G, A, U and/or C.

Yet, in a preferred embodiment, the UTR module (b) or (c), within the RNA molecule of the present invention in relation to module (a) (i.e., the coding region), is directly placed adjacent to the start codon of the coding region of module (a) without any spacing or gap in between, i.e., directly upstream of the start codon of the coding region of module (a).

In another preferred embodiment, the UTR module (b) or (c), within the RNA molecule of the present invention in relation to module (a) (i.e., the coding region), is directly placed adjacent to the termination codon (i.e., the stop codon) of the coding region of module (a) without any spacing or gap in between, i.e., directly downstream of the termination codon/stop codon of the coding region of module (a).

In a preferred embodiment, the UTR module (b), within the RNA molecule of the present invention in relation to module (a) (i.e., the coding region), is directly placed adjacent to the start codon of the coding region of module (a) without any spacing or gap in between, i.e., directly upstream of the start codon of the coding region of module (a) and the UTR module (c), within the RNA molecule of the present invention in relation to module (a) (i.e., the coding region), is directly placed adjacent to the termination codon (i.e., the stop codon) of the coding region of module (a) without any spacing or gap in between, i.e., directly downstream of the termination codon/stop codon of the coding region of module (a).

As mentioned above, the RNA molecule may be present in the form of fused RNA sequences of modules (a), (b) and/or (c), i.e., a (fusion) RNA molecule which is formed by the transcription of a hybrid gene made by combining at least two nucleotide sequences encoding said modules. Typically, this is accomplished by cloning a cDNA into an expression vector which allows for the transcription of the entire RNA molecule. A variety of methods are known for making fusion constructs, including nucleic acid synthesis, hybridization and/or amplification to produce a synthetic double-stranded nucleic acid molecule "encoding" the RNA molecule of the present invention. Such a double-stranded nucleic acid molecule (i.e., DNA molecule) harbors on one strand (i.e., on the coding strand) the DNA sequence corresponding to the RNA molecule of the present invention and, accordingly, "encodes" the RNA molecule of the present invention. In other words, such a double-stranded nucleic acid/DNA molecule comprises on a strand the genetic information, when transcribed, the RNA molecule of the present invention as defined herein above. The term "coding" or "encoding" in the context of the present invention is not only used in its conventional sense, i.e., to relate to a gene's DNA that codes for a protein (and, accordingly, the genetic information which may be translated into a polypeptide or a protein amino acid sequence). Rather, in terms of the present invention, in a construct wherein the individual DNA sequences encoding the modules (a), (b) and/or (c) are "fused" or linked into a single (chimeric) DNA molecule, the construct also comprises components (i.e., module (b) and/or module (c)) which are not translated into a protein. Nevertheless, the DNA sequence corresponding to module (b) and/or module (c) provide the information, i.e., the "code", for the UTRs' structure of the present invention and, accordingly, the term "encoding" in the present invention also relates to the genetic information for the UTRs which may be expressed, i.e., transcribed, if, e.g., present in a double-stranded nucleic acid molecule which harbors on one strand the RNA molecule of the present invention. Thus, the term "encoding" in the context of the present invention, although it is commonly only used to relate to the coding/expression of a protein, is to be understood in a way that the nucleic acid molecule can be transcribed into the RNA molecule of the present invention which harbours parts encoding a protein or a polypeptide (i.e., module (a)) and parts "encoding" the UTRs (i.e., modules (b) and/or (b)) wherein the latter represent the final product when expressed since UTRs are not translated into proteins or polypeptides. Such a double-stranded nucleic acid may be inserted into expression vectors for fusion protein production by standard molecular biology techniques (see, e.g. Sambrook et al., Molecular Cloning, A laboratory manual, 2nd Ed, 1989). The term "vector" such as "expression vector" or "cloning vector" in the sense of the present invention is understood as a circular, double-stranded unit of DNA that replicates within a cell independently of the chromosomal DNA and which is used as a vehicle to carry genetic material into a cell, where it can be replicated and/or expressed (i.e., transcribed into RNA and translated into a amino acid sequence). A vector containing foreign DNA is termed recombinant DNA. The vector itself is generally a DNA sequence that typically consists of an insert (i.e., module (b) and/or module (c) which are not translated into a protein and module (a) the coding region) and a larger sequence that serves as the "backbone" of the vector. Plasmids in the sense of the present invention are most often found in bacteria and are used in recombinant DNA research to transfer genes between cells and are as such a subpopulation of "vectors" as used in the sense of the present invention.

Thus, the present invention also relates to a nucleic acid molecule encoding the RNA molecule of the present invention.

The nucleic acid is, for example a DNA, encoding two of the three main modules (i.e., module (a) and module (b) or module (c)) of the RNA molecule of the present invention. Alternatively, the nucleic acid, preferably a DNA, encodes all three main modules (i.e., module (a) and module (b) and module (c)). The above nucleic acid molecule of the present invention preferably is a recombinant nucleic acid molecule but may also comprise naturally occurring nucleic acid molecules. The nucleic acid molecule of the invention may, therefore, be of natural origin, synthetic or semi-synthetic. It may comprise DNA, RNA, locked nucleic acid as well as PNA and it may be a hybrid thereof.

It is evident to the person skilled in the art that regulatory sequences may be added to the nucleic acid molecule of the invention encoding the RNA molecule. For example, promoters, transcriptional enhancers and/or sequences which allow for induced expression of the polynucleotide, i.e., the RNA molecule, of the invention may be employed. A suitable inducible system is for example tetracycline-regulated gene expression as described, e.g., by Gossen and Bujard, Proc. Natl. Acad. Sci. USA 89 (1992), 5547-5551) and Gossen, Trends Biotech. 12 (1994), 58-62, or a dexamethasone-inducible gene expression system as described, e.g. by Crook, EMBO J. 8 (1989), 513-519.

Furthermore, said nucleic acid molecule may contain, for example, thioester bonds and/or nucleotide analogues. Said modifications may be useful for the stabilization of the nucleic acid molecule against endo- and/or exonucleases in the cell. Said nucleic acid molecules may be transcribed from an appropriate vector containing a chimeric gene which allows for the transcription of said nucleic acid molecule in the cell. In the context of the present invention said nucleic acid molecules may also be labeled. Methods for the detection of nucleic acids are well known in the art, e.g., Southern and Northern blotting, PCR or primer extension.

The nucleic acid molecule(s) of the invention may be a recombinantly produced chimeric nucleic acid molecule comprising any of the aforementioned nucleic acid molecules either alone or in combination. Preferably, the nucleic acid molecule of the invention is part of a vector.

The present invention therefore also relates to a vector comprising the nucleic acid molecule of the present invention. Accordingly, the present invention relates to vectors, preferably expression vectors comprising the nucleic acids of the invention.

The vector of the present invention may be, e.g., a plasmid, cosmid, virus, bacteriophage or another vector used e.g. conventionally in genetic engineering, and may comprise further genes such as marker genes which allow for the selection of said vector in a suitable host cell and under suitable conditions.

Furthermore, the vector of the present invention may, in addition to the sequences of the nucleic acid molecule encoding the RNA molecule of the invention, comprise expression control elements, allowing proper expression of the coding regions in suitable hosts. Such control elements are known to the skilled person and may include a promoter, a splice cassette, translation start codon, translation and insertion site for introducing an insert into the vector. Preferably, the nucleic acid molecule of the invention is operatively linked to said expression control sequences allowing expression in eukaryotic or prokaryotic cells. Accordingly, the present invention relates to a vector comprising the nucleic acid molecule of the present invention, wherein the nucleic acid molecule is operably linked to control sequences that are recognized by a host cell when the eukaryotic and/or prokaryotic (host) cell is transfected with the vector.

Control elements ensuring expression in eukaryotic and prokaryotic (host) cells are well known to those skilled in the art. As mentioned herein above, they usually comprise regulatory sequences ensuring initiation of transcription and optionally poly-A signals ensuring termination of transcription and stabilization of the transcript. Yet, in accordance of the present invention, it is not crucial that the vector itself harbors a sequence for a poly-A tail. As mentioned above, in case the RNA molecule of the present invention is produced by an in vitro transcription method as described herein further below the above poly-A tail is part of the construct of the present invention (and not necessarily originally located on the cloning vector) and is located at the 3' end of the RNA adjacent to the UTR at the 3' end of the RNA construct. In case the RNA molecule of the present invention is produced by an in vitro transcription method the plasmid harboring the RNA molecule of the present invention is linearized prior to the in vitro transcription downstream of the poly-A tail in order to assure that the in vitro transcribed RNA molecule contains said poly-A tail. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous Sarcoma Virus), human elongation factor 1a-promoter, the glucocorticoid-inducible MMTV-promoter Mouse Mammary Tumor Virus), metallothionein- or tetracyclin-inducible promoters, or enhancers, like CMV enhancer or SV40-enhancer. For expression in neural cells, it is envisaged that neurofilament-, PGDF-, NSE-, PrP-, or thy-1-promoters can be employed. Said promoters are known in the art and, inter alia, described in Charron, J. Biol. Chem. 270 (1995), 25739-25745. For the expression in prokaryotic cells, a multitude of promoters including, for example, the tac-lac-promoter or the trp promoter, has been described. Besides elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-vitrogene), pSPORT1 (GIBCO BRL), pX (Pagano, Science 255 (1992), 1144-1147), yeast two-hybrid vectors, such as pEG202 and dpJG4-5 (Gyuris, Cell 75 (1995), 791-803), or prokaryotic expression vectors, such as lambda gt11 or pGEX (Amersham-Pharmacia).

Furthermore, the vector of the present invention may also be an expression vector. The nucleic acid molecules and vectors of the invention may be designed for direct introduction or for introduction via liposomes, viral vectors (e.g. adenoviral, retroviral), electroporation, ballistic (e.g. gene gun) or other delivery systems into the cell. Additionally, a baculoviral system can be used as eukaryotic expression system for the nucleic acid molecules of the invention.

The present invention also relates to a host cell comprising the vector of the present invention. Thus, the present invention relates to a host transfected or transformed with the vector of the invention or a non-human host carrying the vector of the present invention, i.e. to a host cell or host which is genetically modified with a nucleic acid molecule according to the invention or with a vector comprising such a nucleic acid molecule. The term "genetically modified" means that the host cell or host comprises in addition to its natural genome a nucleic acid molecule or vector according to the invention which was introduced into the cell or host or into one of its predecessors/parents. The nucleic acid molecule or vector may be present in the genetically modified host cell or host either as an independent molecule outside the genome, preferably as a molecule which is capable of replication, or it may be stably integrated into the genome of the host cell or host. The transformation of the host cell with a vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The host cell of the present invention may be any prokaryotic or eukaryotic cell. Suitable prokaryotic cells are those generally used for cloning like E. coli or Bacillus subtilis. Furthermore, eukaryotic cells comprise, for example, fungal or animal cells. Examples for suitable fungal cells are yeast cells, preferably those of the genus Saccharomyces and most preferably those of the species Saccharomyces cerevisiae. Suitable animal cells are, for instance, insect cells, vertebrate cells, preferably mammalian cells, such as e.g. HEK293, NSO, CHO,COS-7, MDCK, U2-OSHela, NIH3T3, MOLT-4, Jurkat, PC-12, PC-3, IMR, NT2N, Sk-n-sh, CaSki, C33A. Further suitable cell lines known in the art are obtainable from cell line depositories, like, e.g., the Deutsche Sammlung von Mikroorganismen and Zellkulturen GmbH (DSMZ) or the American Type Culture Collection (ATCC). In accordance with the present invention, it is furthermore envisaged that primary cells/cell cultures may function as host cells. Said cells are in particular derived from insects (like insects of the species Drosophila or Blatta) or mammals (like human, swine, mouse or rat). Said host cells may also comprise cells from and/or derived from cell lines like neuroblastoma cell lines. The above mentioned primary cells are well known in the art and comprise, inter alia, primary astrocytes, (mixed) spinal cultures or hippocampal cultures.

The present invention also relates to methods of producing the RNA molecule of the present invention by culturing a host cell harbouring an expression vector encoding the individual modules of the present invention or the entire RNA molecule of the invention in culture medium, and recovering the RNA molecule from the host cell or culture medium. The present invention may also relate to a method for producing an RNA molecule of the present invention comprising the cultivation of the host cell of the present invention and optionally recovering the RNA molecule from the culture. Methods of recovering and/or subsequently purifying the RNA molecule of the present invention are known to the person skilled in the art.

The present invention also relates to methods of producing in an in vitro reaction the RNA molecule of the present invention by methods known to the person skilled in the art. More specifically, the RNA molecule of the present invention may be produced in vitro using an in vitro transcription system. In vitro transcription systems are commonly known and usually require a purified linear DNA template containing a DNA sequence "encoding" module (b) and/or module (c) as outlined above wherein said DNA sequence is under the control of an appropriate promoter. Moreover, an in vitro transcription system also commonly requires ribonucleotide triphosphates, a buffer system that includes DTT and magnesium ions, and an appropriate RNA polymerase which provides the enzymatic activity for the in vitro transcription of the DNA sequence into the RNA molecule of the present invention.

Methods which are commonly used to produce RNA molecules using in vitro transcription are well-known to the person skilled in the art and are, e.g., described in Methods Mol. Biol. 703 (2011):29-41.

As mentioned above, in case the RNA molecule of the present invention is produced by an in vitro transcription method as described herein further below the above poly-A tail may be part of the construct of the present invention (and not necessarily originally located on the cloning vector) and is located at the 3' end of the RNA adjacent to the UTR at the 3' end of the RNA construct. In case the RNA molecule of the present invention is produced by an in vitro transcription method the plasmid harboring the RNA molecule of the present invention is linearized prior to the in vitro transcription downstream of the poly-A tail in order to assure that the in vitro transcribed RNA molecule contains said poly-A tail.

Alternatively, the RNA molecule of the present invention may also be chemically synthesized, e.g., by conventional chemical synthesis on an automated nucleotide sequence synthesizer using a solid-phase support and standard techniques.

The present invention also relates to methods of producing in an in vitro reaction the RNA molecule of the present invention by methods known to the person skilled in the art and as outlined above and recovering the RNA molecule from the reaction.

Methods of recovering and/or subsequently purifying the RNA molecule of the present invention are known to the person skilled in the art.

The RNA molecules as defined above are particularly useful in medical settings and in the treatment of a certain disease and, in particular, in RNA-based therapies. Thus, the present invention also relates to a pharmaceutical composition comprising the RNA molecule of the present invention, the nucleic acid molecule of the present invention, the vector of the present invention or the host cell of the present invention and optionally a pharmaceutically acceptable carrier.

The term "treatment" and the like are used herein to generally mean obtaining a desired pharmacological and/or physiological effect. Accordingly, the treatment of the present invention may relate to the treatment of (acute) states of a certain disease but may also relate to the prophylactic treatment in terms of completely or partially preventing a disease or symptom thereof. Preferably, the term "treatment" is to be understood as being therapeutic in terms of partially or completely curing a disease and/or adverse effect and/or symptoms attributed to the disease. "Acute" in this respect means that the subject shows symptoms of the disease. In other words, the subject to be treated is in actual need of a treatment and the term "acute treatment" in the context of the present invention relates to the measures taken to actually treat the disease after the onset of the disease or the breakout of the disease. The treatment may also be prophylactic or preventive treatment, i.e., measures taken for disease prevention, e.g., in order to prevent the infection and/or the onset of the disease.

The pharmaceutical composition of the present invention may be administered via a large range of classes of forms of administration known to the skilled person. Administration may be systemically, locally, orally, through aerosols including but not limited to tablets, needle injection, the use of inhalators, creams, foams, gels, lotions and ointments.

As mentioned, the present invention relates to a pharmaceutical composition, comprising an effective amount of the RNA molecule (or the nucleic acid molecule, the vector or the host cell) of the present invention in accordance with the above and at least one pharmaceutically acceptable excipient or carrier.

An excipient or carrier is an inactive substance formulated alongside the active ingredient, i.e., construct of the present invention in accordance with the above, for the purpose of bulking-up formulations that contain potent active ingredients. Excipients are often referred to as "bulking agents," "fillers," or "diluents". Bulking up allows convenient and accurate dispensation of a drug substance when producing a dosage form. They also can serve various therapeutic-enhancing purposes, such as facilitating drug absorption or solubility, or other pharmacokinetic considerations. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients also depends upon the route of administration and the dosage form, as well as the active ingredient and other factors.

Thus, in line with the above, the pharmaceutical composition comprising an effective amount of the nucleic acid of the present invention may be in solid, liquid or gaseous form and may be, inter alia, in a form of (a) powder(s), (a) tablet(s), (a) solution(s) or (an) aerosol(s). It is preferred that said pharmaceutical composition optionally comprises a pharmaceutically acceptable carrier and/or diluent.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose, i.e., in "an effective amount" which can easily be determined by the skilled person by methods known in the art. The dosage regimen will be determined by the attending physician and clinical factors. As is well known in the medical arts, dosages for any one patient depends upon many factors, including the patient's or subject's size, body surface area, age, the particular compound to be administered, sex, time and route of administration, general health, and other drugs being administered concurrently.

Thus, preferably, the construct of the present invention is included in an effective amount. The term "effective amount" refers to an amount sufficient to induce a detectable therapeutic response in the subject to which the pharmaceutical composition is to be administered. In accordance with the above, the content of the construct of the present invention in the pharmaceutical composition is not limited as far as it is useful for treatment as described above, but preferably contains 0.0000001-10% by weight per total composition. Further, the construct described herein is preferably employed in a carrier. Generally, an appropriate amount of a pharmaceutically acceptable salt is used in the carrier to render the composition isotonic. Examples of the carrier include but are not limited to saline, Ringer's solution and dextrose solution. Preferably, acceptable excipients, carriers, or stabilisers are non-toxic at the dosages and concentrations employed, including buffers such as citrate, phosphate, and other organic acids; salt-forming counter-ions, e.g. sodium and potassium; low molecular weight (>10 amino acid residues) polypeptides; proteins, e.g. serum albumin, or gelatine; hydrophilic polymers, e.g. polyvinylpyrrolidone; amino acids such as histidine, glutamine, lysine, asparagine, arginine, or glycine; carbohydrates including glucose, mannose, or dextrins; monosaccharides; disaccharides; other sugars, e.g. sucrose, mannitol, trehalose or sorbitol; chelating agents, e.g. EDTA; non-ionic surfactants, e.g. Tween, Pluronics or polyethylene glycol; antioxidants including methionine, ascorbic acid and tocopherol; and/or preservatives, e.g. octadecyldimethylbenzyl ammonium chloride; hexamethonium chloride; benzalkonium chloride, benzethonium chloride; phenol, butyl or benzyl alcohol; alkyl parabens, e.g. methyl or propyl paraben; catechol; resorcinol; cyclohexanol; 3-pentanol; and m-cresol). Suitable carriers and their formulations are described in greater detail in Remington's Pharmaceutical Sciences, 17th ed., 1985, Mack Publishing Co.

Therapeutic progress can be monitored by periodic assessment. The RNA molecule of the present invention or the pharmaceutical composition of the invention may be in sterile aqueous or non-aqueous solutions, suspensions, and emulsions as well as creams and suppositories. Examples of non-aqueous solvents are propylene glycol, polyethylene glycol, vegetable oils such as olive oil, and organic esters such as ethyl oleate. Aqueous carriers include water, alcoholic/aqueous solutions, emulsions or suspensions, including saline and buffered media. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition. Said agents may be, e.g., polyoxyethylene sorbitan monolaurate, available on the market with the commercial name Tween, propylene glycol, EDTA, Citrate, Sucrose as well as other agents being suitable for the intended use of the pharmaceutical composition that are well-known to the person skilled in the art.

In accordance with this invention, the term "pharmaceutical composition" relates to a composition for administration to a patient, preferably a human patient.

The pharmaceutical composition of the present invention may be for use in RNA-based therapies. As mentioned above, the RNA molecule of the present invention comprising a "coding region coding for a polypeptide" can be used in RNA-based therapies wherein the "coding region coding for a polypeptide" encodes a therapeutically or pharmaceutically active polypeptide or protein having a therapeutic or preventive effect. Thus, in preferred embodiments, the pharmaceutical composition of the present invention may be for use in RNA-based therapies in the treatment or prevention of a disease as recited in the above Table 2. Accordingly, RNA-based therapies in accordance with the present invention may be for use in the treatment or prevention of a disease as recited in the above Table 2.

Thus, the pharmaceutical composition of the present invention may be for use in RNA-based therapies in cases where the gene defects described in the above Table 2 lead to a disease which can then be treated or prevented by a transcript replacement therapy/enzyme replacement therapy with the RNA molecule of the present invention, wherein the RNA molecule comprises a "coding region for a polypeptide" which encodes an intact version of the protein or a functional fragment thereof compensating the disclosed defective gene. In particularly preferred embodiments, the pharmaceutical composition of the present invention may be for use in RNA-based therapies in the treatment or prevention of lysosomal diseases like Gaucher disease, Fabry disease, MPS I, MPS II (Hunter syndrome), MPS VI and Glycogen storage diseases such as for example Glycogen storage disease type I (von Gierecke's disease), type II (Pompe's disease), type III (Cori's disease, type IV (Andersen's disease, type V (McArdle's disease, type VI (Hers disease), type VII (Tauri's disease), type VII, type IX, type X, type XI (Fanconi-Bickel syndrome), type XI, or type 0. Transcript replacement therapies/enzyme replacement therapies beneficially do not affect the underlying genetic defect, but increase the concentration of the enzyme in which the patient is deficient. As an example, in Pompe's disease, the transcript replacement therapy/enzyme replacement therapy replaces the deficient Lysosomal enzyme acid alpha-glucosidase (GAA).

In other preferred embodiments, the pharmaceutical composition of the present invention may be for use in RNA-based therapies in accordance with the present invention wherein the "coding region coding for a polypeptide" encodes a therapeutically or pharmaceutically active polypeptide, protein or peptide having a therapeutic or preventive effect, wherein said polypeptide, protein or peptide is selected from the group encoded by the genes as outlined in Table 2.

In other preferred embodiments, RNA-based therapies in accordance with the present invention may be for use in treating cancer, a cardiovascular disease, a viral infection, an immune dysfunction, an autoimmune disease, a neurologic disorder, an inherited metabolic disorders or a genetic disorder or any disease where a protein or protein fragment produced in a cell may have a beneficial effect for the patent. Examples of cancer include head and neck cancer, breast cancer, renal cancer, bladder cancer, lung cancer, prostate cancer, bone cancer, brain cancer, cervical cancer, anal cancer, colon cancer, colorectal cancer, appendix cancer, eye cancer, gastric cancer, leukemia, lymphoma, liver cancer, skin cancer, ovarian cancer, penile cancer, pancreatic cancer, testicular cancer, thyroid cancer, vaginal cancer, vulvar cancer, endometrial cancer, cardiac cancer and sarcoma.

Examples of cardiovascular diseases include atherosclerosis, coronary heart disease, pulmonary heart disease and cardiomyopathy.

Examples of immune dysfunctions and autoimmune diseases include, but are not limited to, rheumatic diseases, multiple sclerosis and asthma.

Examples of viral infections include, but are not limited to, infections with human immunodeficiency virus, herpes simplex virus, human papillomavirus as well as hepatitis B and C virus.

Examples of neurologic disorders include, but are not limited to, Parkinson's disease, multiple sclerosis, and dementia.

Examples of inherited metabolic disorders include, but are not limited to, Gaucher's disease and Phenylketonuria.

The invention also relates to a method of an RNA-based therapy. Thus, the present invention relates to a method for the treatment of a disease such as cancer, a cardiovascular disease, a viral infection, an immune dysfunction, an autoimmune disease, a neurologic disorder, an inherited metabolic disorders or a genetic disorder by an RNA-based therapy. As regards the preferred embodiments of the method for treatment the same applies, mutatis mutandis, as has been set forth above in the context of the RNA molecule or the pharmaceutical composition for use in RNA-based therapy as defined above.

In the present invention, the subject is, in a preferred embodiment, a mammal such as a dog, cat, pig, cow, sheep, horse, rodent, e.g., rat, mouse, and guinea pig, or a primate, e.g., gorilla, chimpanzee, and human. In a most preferable embodiment, the subject is a human.

The present invention also relates to a kit comprising the RNA molecule of the present invention, the nucleic acid molecule of the present invention, the vector of the present invention or the host cell of the present invention. As regards the preferred embodiments, the same applies, mutatis mutandis, as has been set forth above in the context of the RNA molecule, nucleic acid molecule, vector or the host cell according to the present invention. Advantageously, the kit of the present invention further comprises, optionally (a)

buffer(s), storage solutions and/or remaining reagents or materials required for the conduct of the above and below uses and methods. Furthermore, parts of the kit of the invention can be packaged individually in vials or bottles or in combination in containers or multicontainer units. The kit of the present invention may be advantageously used, inter alia, for carrying out the methods of the invention, the preparation of the RNA molecule of the invention and could be employed in a variety of applications referred herein, e.g., in the uses as outlined above and below. Another component that can be included in the kit is instructions to a person using a kit for its use. The manufacture of the kits follows preferably standard procedures which are known to the person skilled in the art.

Finally, the present invention also relates to the use of one or more UTR(s) comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1; and/or of one or more UTR(s) comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2 for increasing the efficiency of translating a coding region of an RNA molecule into a polypeptide or a protein encoded by said coding region as being defined above. As regards the preferred embodiments of the use the same applies, mutatis mutandis, as has been set forth above in the context of the RNA molecule of the present invention.

FIG. 1: Fluorescence microscopy and flow cytometry data of A549 cells.
- (A) Schematic illustration of therapeutic mRNA, consisting of a 5' CAP, a 5' UTR, an encoding region, a 3' UTR and a poly-A tail.
- (B) Fluorescence microscopy pictures taken with 4× magnification (JULY™) at 24 h post-transfection. All constructs showed improved protein expression levels as compared to the control.
- (C) The percentage of d2EGFP positive cells as determined by FC is similar for all constructs. Propidium iodide was used to detect dead cells. The applied gates ensured exclusion of dead cells and untransfected cells.
- (D) At 48 h post transfection, sustained protein expression was higher for the stabilized constructs as compared to the control.

Figure 2:
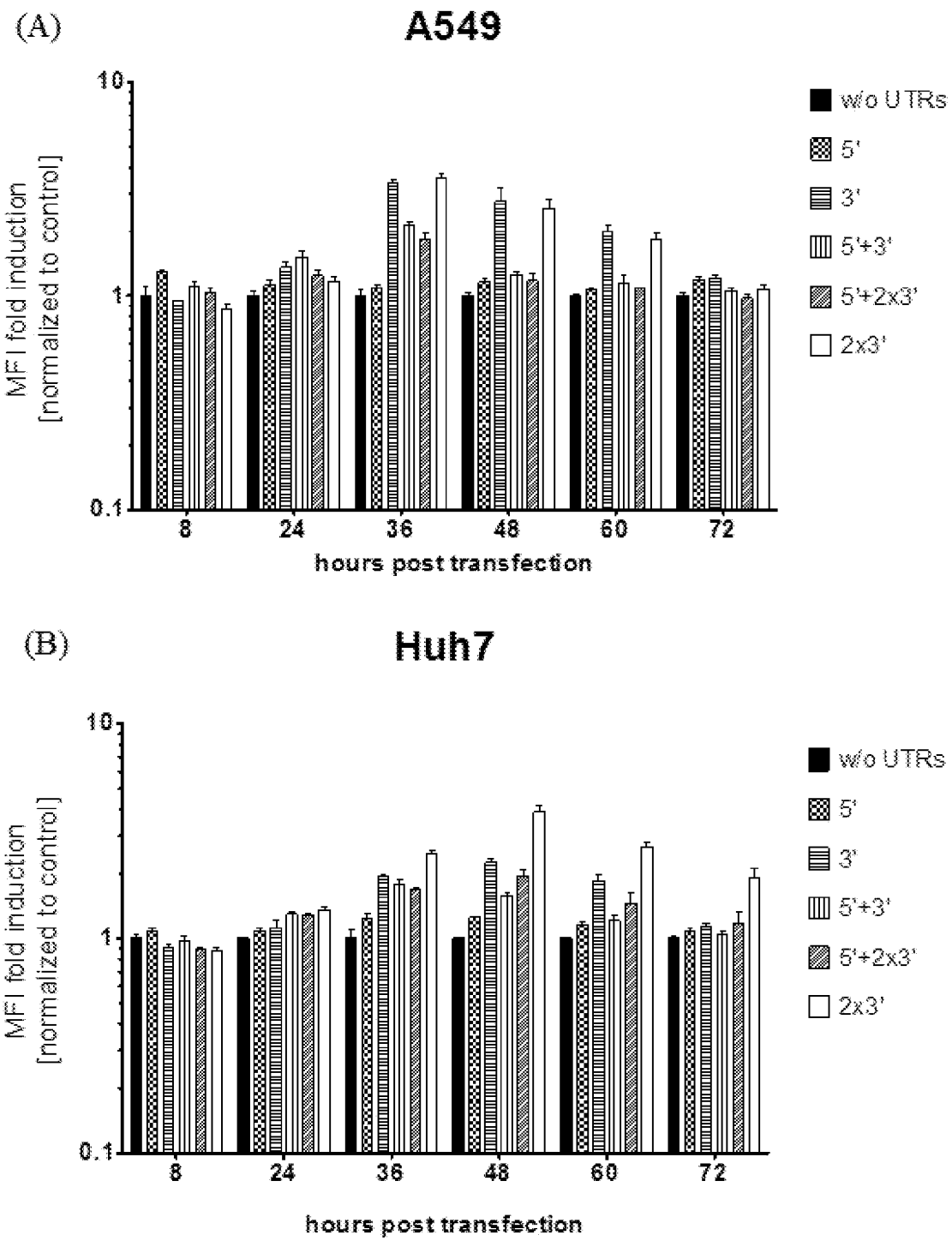

FIG. 2: Time courses of protein expression as determined by FC for A549 cells (A) and Huh7 cells (B). Mean fluorescence intensities normalized to the control are plotted versus time in a log-linear plot. With increasing time post transfection, the elevated protein expression levels of the stabilized constructs become more and more evident. The bars corresponding to the control, 5'UTR and 3'UTR constructs, respectively, as well as to the constructs 5'+3', 5'+2×3' and 2×3' are differently shaded as shown on the right hand side of the figure.

Figure 3:
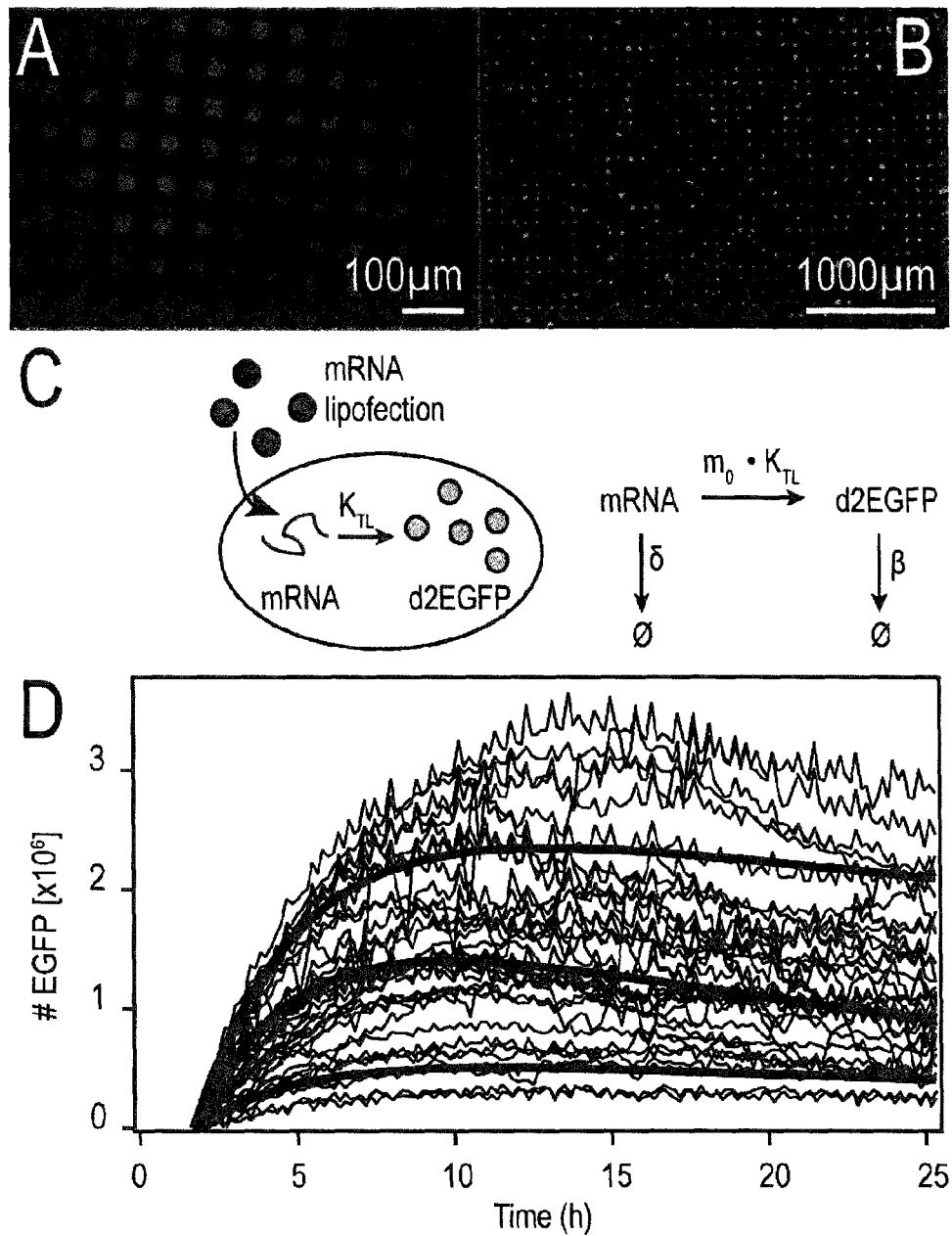

FIG. 3: Microstructured multi-channel slides for parallel single-cell assays to test differently stabilized mRNA constructs.
- (A) Cell-adhesive, microstructured protein patterns with cell-repellent PEG areas in between allow ordered cell arrangement. Fluorescently labeled fibronectin was used to visualize the micropattern.
- (B) Fluorescent A549 cells adhering to fibronectin patterns inside a microchannel (three hours after seeding).
- (C) Schematic drawing of mRNA lipofection (on the left) and reaction scheme underlying our analytical solution (on the right).
- (D) Exemplary time courses of mRNA-mediated d2EGFP expression in A549 cells. Black lines are representative fits to the theoretical translation model.

Figure 4:
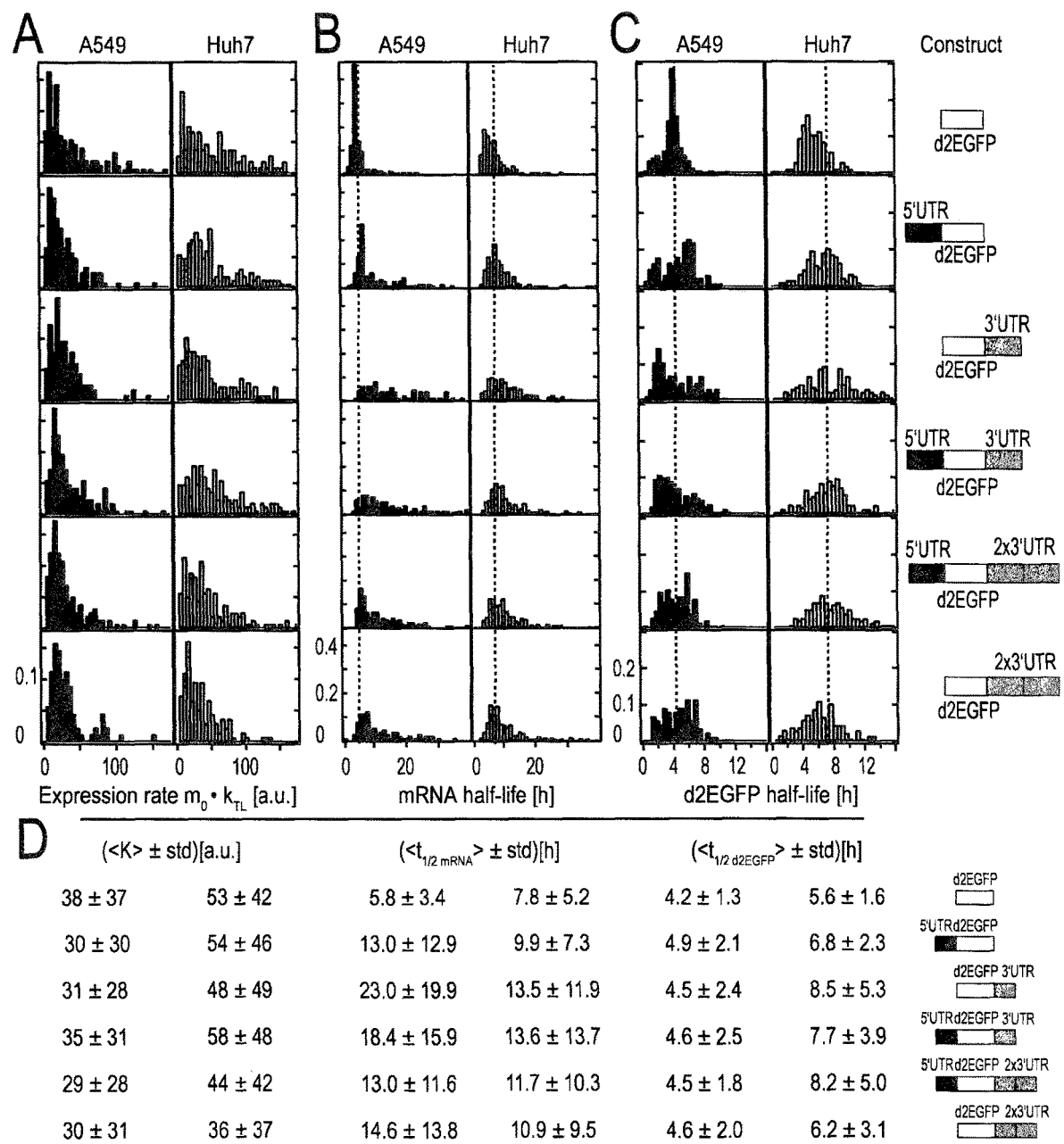

FIG. 4: Distributions of expression rates K, mRNA life times, and d2EGFP life times and corresponding mean values with schematic representations of the constructs.
- (A) Distributions of expression rate K, which is the product of the initial number of mRNA molecules and the translation rates. The fact that the distributions are similarly shaped indicates that the transfection kinetics and the translation rates are very similar.
- (B) The distributions of the mRNA half-lives show great variations in their broadness. As a guide to the eye, dotted lines indicate the mean half-life of the control.
- (C) Distributions of d2EGFP half-lives. As expected, the distributions of the different constructs are similarly shaped and show comparable mean values. As a guide to the eye, the overall mean half-life of d2EGFP based on all measured half-lives is shown as a dotted line.
- (D) Mean values and the corresponding standard deviations (std) of the fitted rates. Although the control construct yields high mean K values in both cell types, the short mRNA half-life of this construct leads to small AUC values as compared to the stabilized constructs. This can be seen in FIG. 6. Schematic representations of the constructs can be seen on the right hand side. All constructs have the same 5'cap and a poly-A tail. Data from 895 single A549 and 1355 Huh7 cells were analysed.

Figure 5:
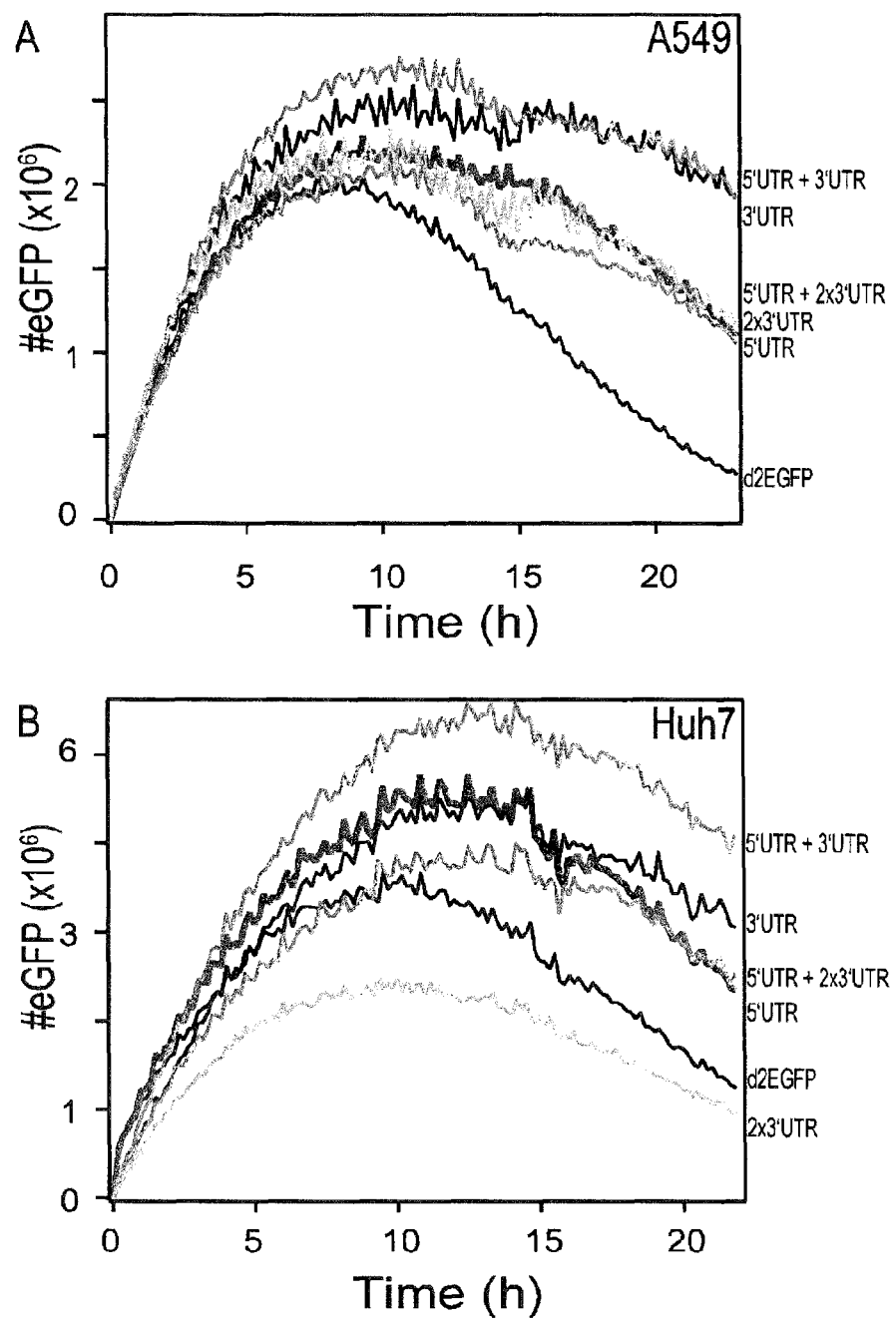

FIG. 5: Mastercurves of the different constructs. Population averages of A549 (A) and Huh7 (B) cells with the onset time shifted to zero. The dark grey, medium grey and light grey curves correspond to the control/5'UTR/3'UTR constructs, respectively. The curves correspond to the constructs as correspondingly indicated on the right hand side.

Figure 6:
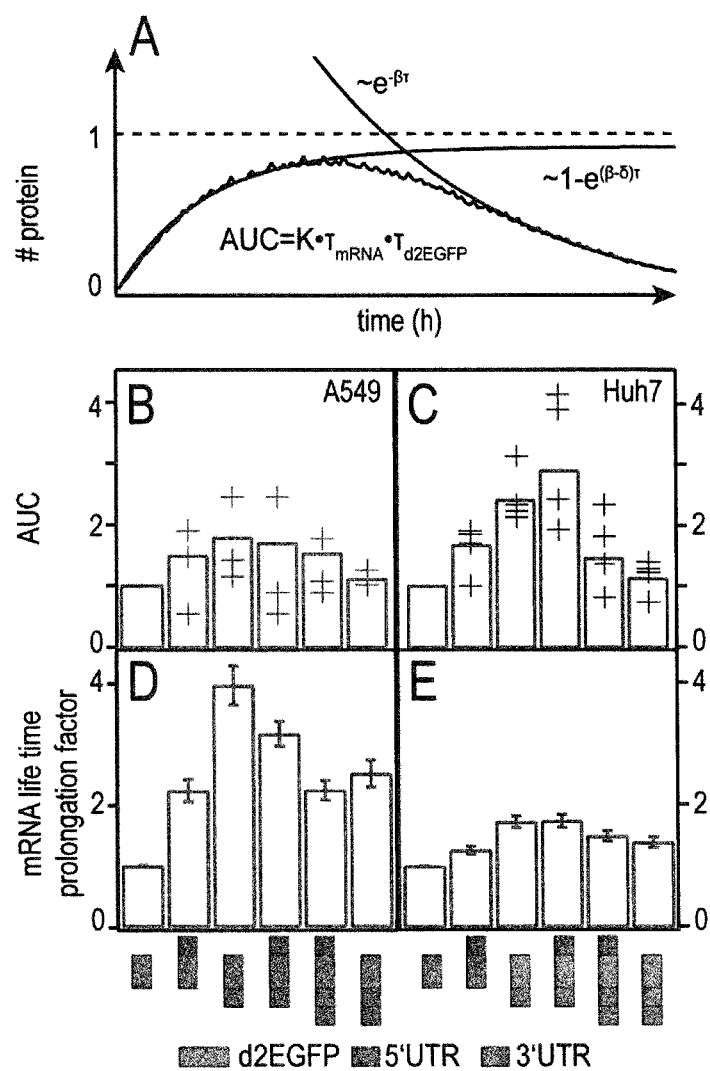

FIG. 6: AUC and mRNA life time prolongation factors of the different constructs.
- (A) Schematic representation of the AUC to illustrate the interplay between mRNA translation and degradation of mRNA and protein.
- (B) and (C) AUC of the different constructs as analysed for t→∞. Crosses show relative AUCs of different experiments, the bars correspond to the mean of all single-cell AUCs.
- (D) and (E) mRNA life time prolongation factors. All modifications result in prolonged mRNA life times as compared to the control. Similar trends are observed in A549 (D) and Huh7 (E) cells. Error bars in (D) and (E) indicate standard deviation.

Figure 7:
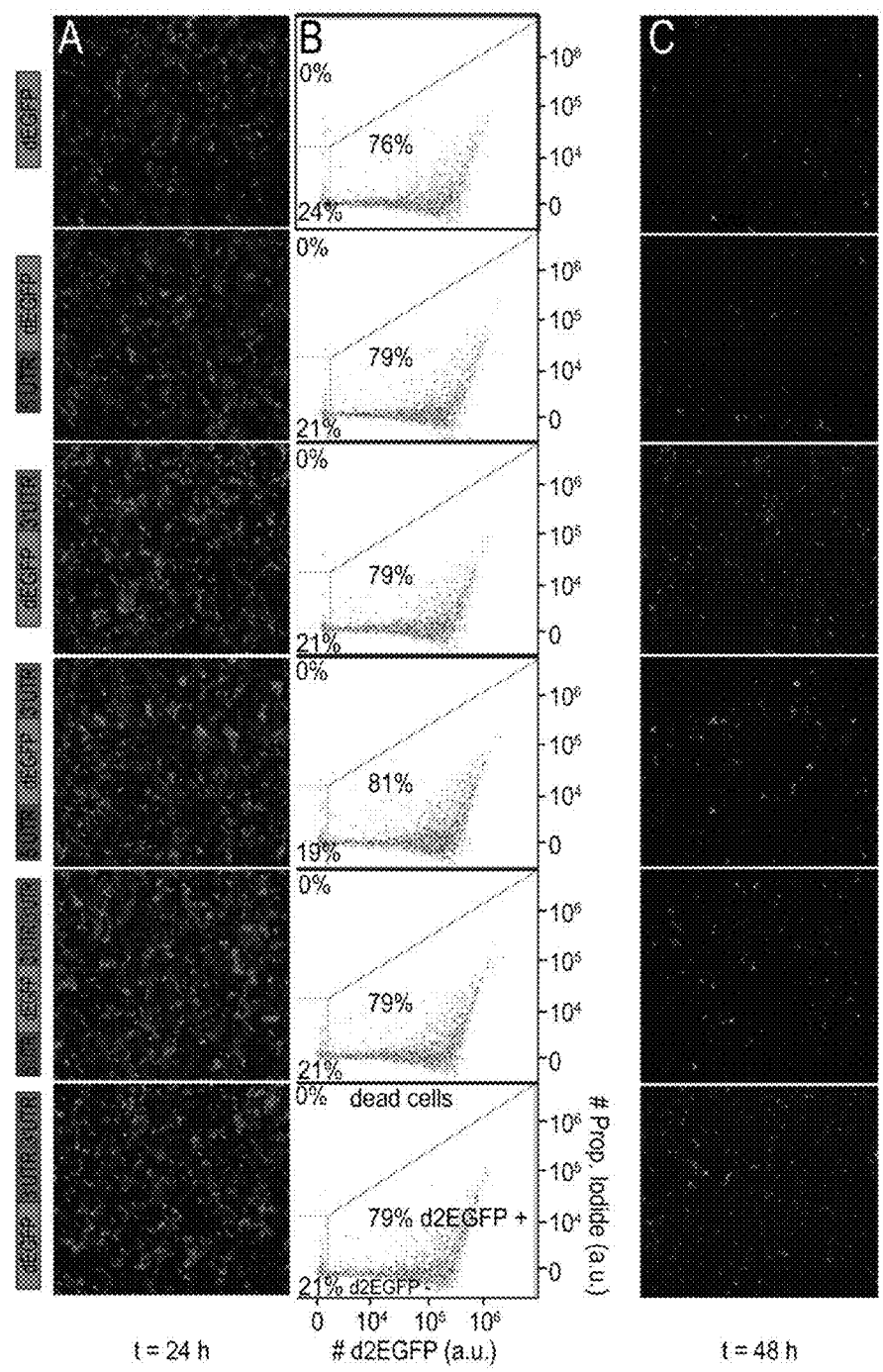

FIG. 7: Fluorescence microscopy and flow cytometry data of Huh7 cells.
- (A) Fluorescence microscopy pictures taken with 4× magnification (JULY™) at 24 h post-transfection. All constructs showed improved protein expression levels as compared to the control.
- (B) The percentage of d2EGFP positive cells as determined by FC is similar for all constructs. Propidium iodide was used to detect dead cells. The applied gates ensured exclusion of dead cells and untransfected cells.
- (C) At 48 h post transfection, sustained protein expression was higher for the stabilized constructs as compared to the control.

Figure 8:
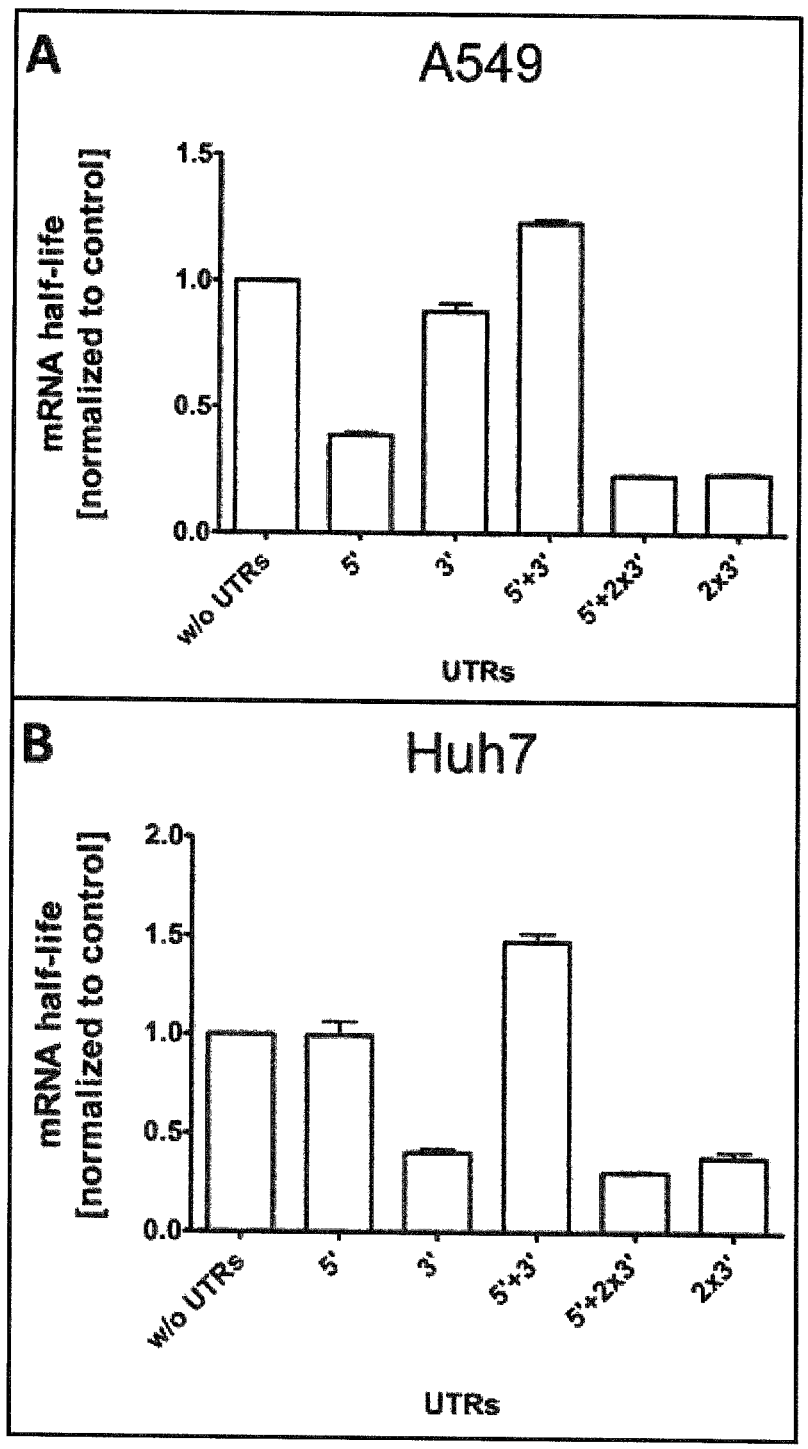

FIG. 8: Determination of mRNA half-life by qRT-PCR in A549 and Huh7 cells. The cells were transfected according to the protocol as described in Materials & Methods part. Absolute mRNA quantification at 4, 8, 24, 36, 48, 60, 72 hours for all mRNA constructs was determined in A549 (see FIG. 8 A) and in Huh7 (see FIG. 8 B). Out of this data the mRNA half-life was calculated. The physical half-life was normalized to the control.

Figure 9:
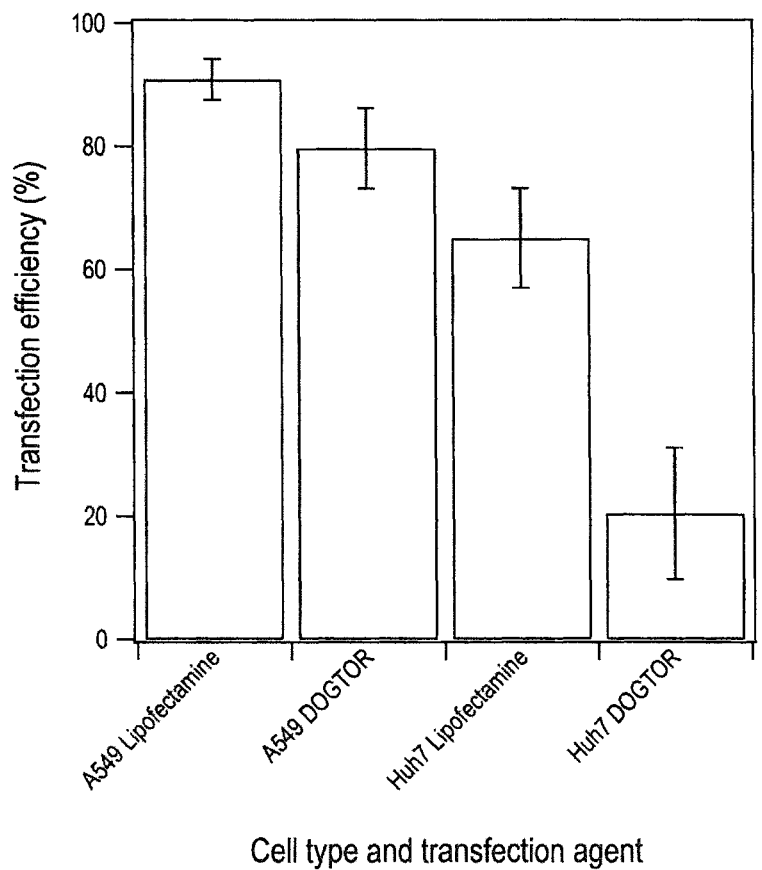

FIG. 9: Transfection efficiencies on microstructured substrates.

Percentage of transfected cells and corresponding standard deviations for A549 cells and Huh7 cells transfected with SNIM RNA with help of Lipofectamine™2000 or DOGTOR. Higher transfection efficiencies were found for cells transfected with Lipofectamine™2000.

Figure 10:
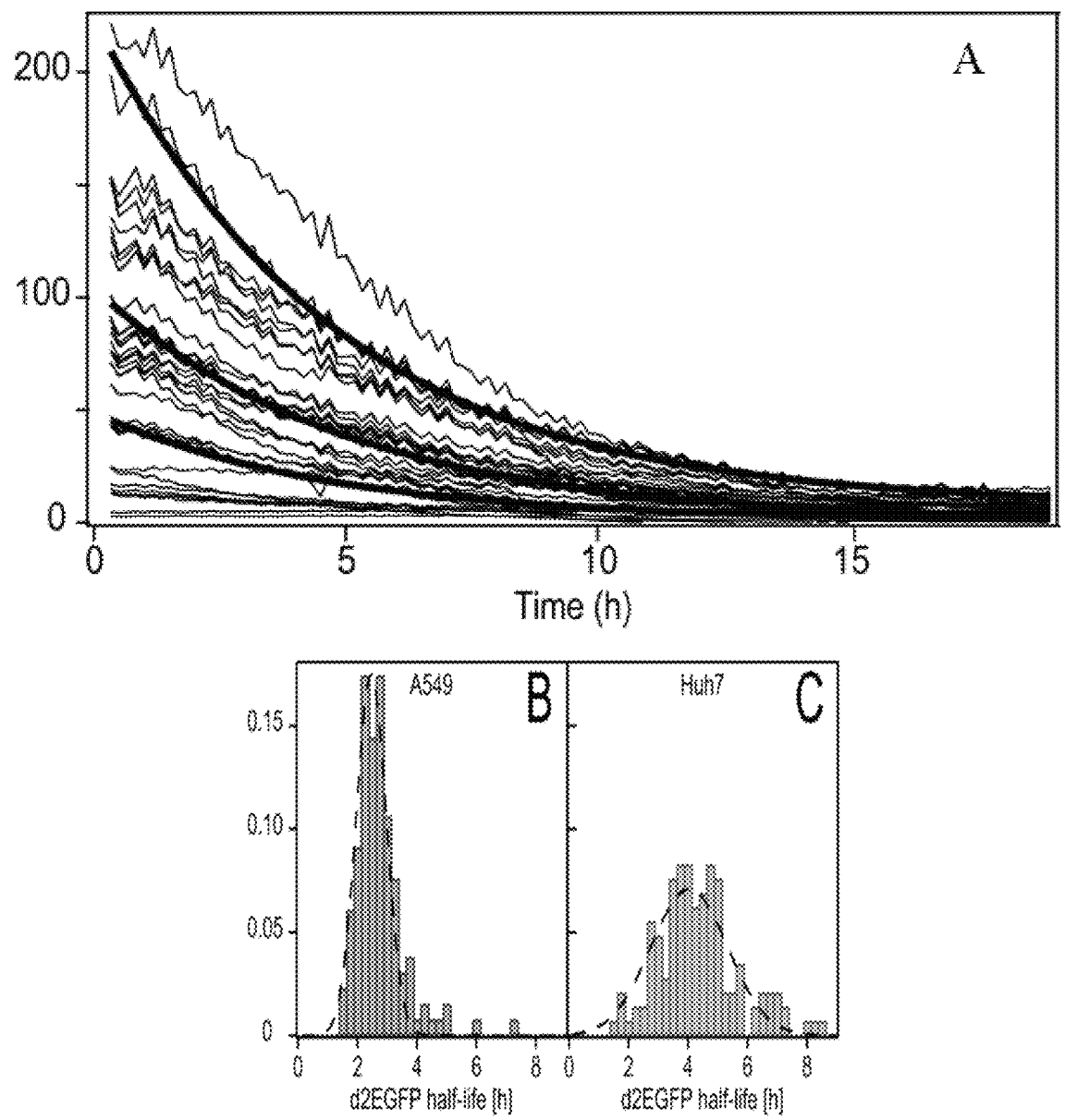

FIG. 10: Distributions of directly measured d2EGFP half-lives.

(A) Exemplary time courses of cycloheximide-induced d2EGFP degradation in Huh7 cells. Black lines are simple exponential fits for protein degradation.
(B) Distribution of d2EGFP half-lives measured in A549 cells, yielding a mean half-life of 2.46 h (std 0.71 h).
(C) Distribution of d2EGFP half-lives measured in Huh7 cells, yielding a mean half-life of 4.04 h (std 1.82 h).

Figure 11:
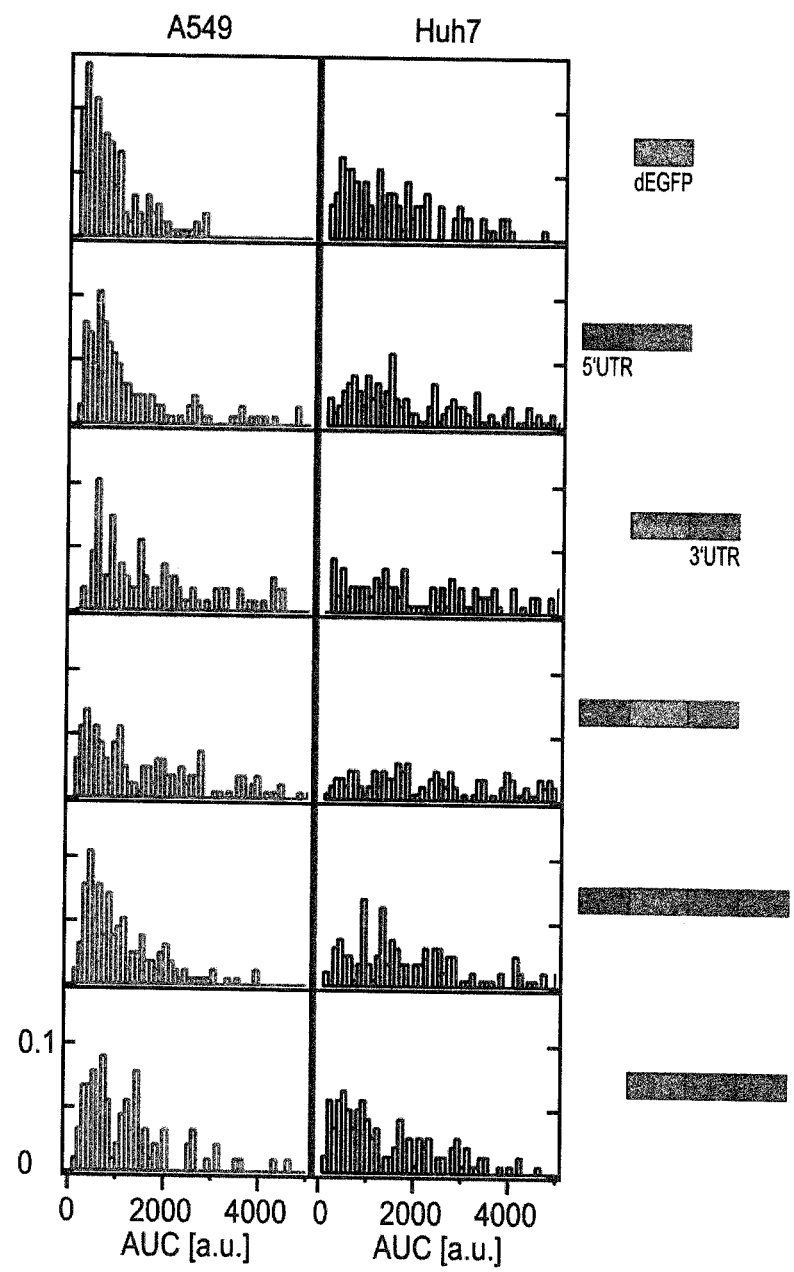

FIG. 11: Distribution of the single-cell AUCs. AUCs were calculated according to equation 3 below. A549 data are shown in the left column, Huh7 data are shown in the right column.

FIG. 12: Comparison of the constructs #2 o #5 having UTRs of different genes as indicated in Table 5 with the CYBA-UTR #1 construct.

Based on previously published data with respect to mRNA stability, preselected 5' and 3' UTR sequences of CYBA gene were synthesized by Eurofins MWG (Germany) and cloned upstream (5'UTR) and/or downstream (3'UTR or 2×3'UTR) of d2EGFP in pVAXA120-d2EGFP, thereby generating the constructs with respective UTR combinations.

mRNA Production

To generate in vitro transcribed mRNA (IVT mRNA), plasmids were linearized downstream of the poly-A tail by NotI digestion and purified by chloroform extraction and ethanol precipitation. Purified linear plasmids were used as template for in vitro transcription using RiboMax Large Scale RNA production System-T7 (Promega, Germany). Anti-Reverse Cap Analog (ARCA) was added to the reaction mix to generate 5' capped mRNA. Additionally for the production of SNIM mRNAs, chemically modified nucleotides namely methyl-CTP and thio-UTP (Jena Bioscience, Germany) were added to a final concentration of ATP:CTP: UTP:methyl-CTP:thio-UTP:GTP of 7.57 mM:5.68 mM:5.68 mM:1.89 mM:1.89 mM:1.21 mM. The complete IVT mix was incubated at 37° C. for 2 hours followed by a DNA disgestion with DNaseI for 20 minutes at 37° C. RNA was precipitated with ammonium acetate (final concentration 2.5M) and washed with 70% EtOH. The washing step was performed twice. Finally, the RNA pellet was re-suspended in RNAse-free water. All mRNAs were verified on 1% agarose gels. A schematic representation of an exemplary mRNA construct can be seen in FIG. 1A. The exact sequences of the UTRs are given in the text below the above Table 1.

TABLE 3

| | | Secondary structures (mfold) | | | |
|---|---|---|---|---|---|
| d2EGFP | ΔG | 5'end | 3' end | 5' UTR | 3'UTR |
| control | −358.9 | partial binding with cds (8/8) | loose (8/8) | none | none |
| 5' CYBA | −375 | partial binding with 5' CYBA UTR (7/8) | loose (8/8) | binds with cds (6/8) | none |
| 3' CYBA | −411.6 | partial binding with 3' CYBA UTR (8/8) | binds with 5'end (4/4) | none | forms one hairpin (7/8) |
| 5' + 3' CYBA | −405.7 | binds with 3' CYBA UTR (3/8) | binds with 5'end (4/4) | binds with 3' CYBA UTR (4/8) | forms one hairpin (7/8) |
| 5' + 2 × 3' CYBA | −437.7 | binds with 3'UTR (8/8) | loose (8/8) | binds with 3'UTR and gene (6/8) | 1st 3'UTR: hairpin; 2nd 3'UTR: hairpin (7/8) |
| 2 × 3' CYBA | −444.1 | binds with itself and forms hairpin (8/8) | loose (7/8) | none | 1st 3'UTR: hairpin; 2nd 3'UTR: two hairpins (3/8) |

Other aspects and advantages of the invention will be described in the following examples, which are given for purposes of illustration and not by way of limitation. Each publication, patent, patent application or other document cited in this application is hereby incorporated by reference in its entirety.

EXAMPLES

I. Materials and Methods

Plasmid Vectors

Destabilized Enhanced Green Fluorescent Protein (d2EGFP) was excised from pd2EGFP-N1 (Clonetech) and cloned in pVAXA120 (3) to generate pVAXA120-d2EGFP.

In Table 3, features of the mRNA constructs such as free minimum energy (ΔG) and secondary structures found at both ends and within the UTRs are listed. The folding platform mfold was used to predict mRNA secondary structures (40). For each construct, we compared the eight secondary structures that have the highest free energy. The highest free energy values are predicted for the 2×3' UTR and the 3' UTR constructs. The 5' end of each mRNA construct partially binds with the 3'UTR or the 5'UTR, except for the control construct, which binds to the coding sequence (cds). Interestingly, the 5' end of the 2×3' mRNA construct forms a stabilizing hairpin with itself. However, hairpin loops near the 5' end can also hinder protein translation (41). Another feature was found in the 3' end of the 3' UTR and 5'+3' UTR mRNA constructs: There, the 3' end binds with the 5' end, minimizing the distance from each other and thus enabling faster initiation of translation. Unlike the 5'UTRs, the 3' UTR of each mRNA construct forms at least one hairpin with itself.

Flow Cytometry (FC)

The experimental set-up looks like as follows: 20.000 cells in 150 µl medium were seeded per well in 96-well plates and transfected 24 hours post-seeding. Cells were transfected at a dose of 5 pg mRNA/cell using the commercial transfection reagent Lipofectamine™ 2000. Complexes were prepared at a ratio of 2.5 µl Lipofectamine™ 2000 per 1 µg mRNA. For the formation of lipoplexes, Lipofectamine™ 2000 and mRNA were diluted separately in OptiMEM transfection medium in a total volume of 50 µl, each. These mixtures were incubated at room temperature for 5 minutes. The mRNA solution was then mixed with the Lipofectamine™ 2000 solution, followed by another 20 minutes of incubation at room temperature. After incubation, 900 µl of OptiMEM were added to the lipoplex solution. Finally, 50 µl of the complex solution were added to the cells and incubated for 1 hour. For every mRNA construct, biological triplicates were prepared. After incubation, the lipoplex-solution was discarded and fresh 150 µl medium was added to each well. d2EGFP expression was measured after 8, 24, 36, 48, 60 and 72 hours using FC. Fluorescence microscopy images were taken at each of these time points. For FC measurements, the cell culture medium was discarded and the cells were washed with 1×DPBS (Gibco Life Technology). Subsequently, 20 µl of TrypLE Express (Gibco Life Technology) were added per well and incubated for 5 min at 37° C. The reaction was neutralized by adding 80 µl 1×PBS, supplemented with 2% FBS. Cells were mixed by pipetting and were transferred into a 96 well plate appropriate for flow cytometric measurements. Finally, 5 µl of Propidium iodide (final concentration 1 µg/ml) were added per well and measured with Attune Auto Sampler (Applied Biosystems). Fluorescence images were taken prior to FC analysis with a JULY™ microscope.

Quantitative Real-Time PCR

A qRT-PCR analysis was used to determine the d2EGFP mRNA amount at time intervals of 4, 8, 24, 36, 48, 60 and 72 hours in A549 and Huh? cells. Additionally, the mRNA expression kinetic itself was used to calculate the mRNA half-life of each UTR. Here, the cells were transfected similarly to the protocol described above (see FC). A cell density of 200.000 cells/well was found to be sufficient for RNA isolation. RNA isolation was performed according to the manufacturer's protocol using NucleoSpin RNA (Macherey Nagel). The isolated total RNA was examined in RNA concentration and quality by spectrophotometric measurements and gel analysis. Further, 0.5 µg of the total RNA of each UTR constructs and the control were used for cDNA synthesis using Oligo(dT)s from First Strand cDNA Synthesis Kit (Thermo Scientific). Equivalent amounts of cDNA (diluted 1:50) were tested with 125 nM of each d2EGFP-Primer (forward Primer: 5'-CAA CCA CTA CCT GAG CAC CC-3' (SEQ ID NO:3); reverse Primer:5'-GTC CAT GCC GAG AGT GAT CC-3' (SEQ ID NO:4)) using SsoAdvanced™ Universal SYBR® Green Supermix (BioRad). As a standard for the absolute quantification, pure d2EGFP mRNA produced by IVT was used for synthesis of cDNA. Absolute mRNA quantification was performed on a Lightcycler 96 device (Roche).

Surface Patterning and Sample Preparation

Microstructured surfaces were produced by selective oxygen plasma treatment (Femto Diener, 40 W for 3 min) on a top as substrate (ibidi GmbH) with subsequent passivation. Selectivity was achieved using a polydimethylsiloxane (PDMS) stamp (cast from a master produced by photolithography) as a mask. The parts exposed to plasma were passivated by incubation for 30 min with PLL(20k)-g(3.5)-PEG(2k) at a concentration of 1 mg/ml in aqueous buffer (10 mM HEPES pH 7.4 and 150 mM NaCl). Thereafter, the samples were rinsed with PBS and the PDMS stamps were removed. The foils were then fixed to adhesive six-channel slides (sticky p-slide VI). Each channel was filled with a solution of 50 µg/ml fibronectin in PBS for one hour to render the remaining sectors cell-adhesive. Probes were thoroughly rinsed with PBS three times. The samples were stored in cell medium at room temperature before cell seeding. For this study, square adhesion sites of 30 µm×30 µm were used because this size turned out to be reasonable for single-cell adhesion of A549 as well as Huh? cells. Cells were seeded at a density of 10,000 cells per channel so that roughly one cell could adhere on each cell-adhesive island. To obtain fluorescent micropatterns as shown in FIG. 3A, a mixture of 20 µg/ml fibronectin and 30 µg/ml fibrinogen conjugated with Alexa Fluor 488 was used.

Materials

FBS, Leibovitz's L-15 Medium (Gibco), Lipofectamine™ 2000, and OptiMEM (Gibco) were purchased from Invitrogen, Germany. Sterile PBS was prepared inhouse. Ham's F-12K, DMEM, and Trypsin-EDTA were purchased from c.c.pro GmbH, Germany. Channel slides were purchased from ibidi, Germany. Fibronectin was purchased from Yo Proteins, Sweden. PLL-g-PEG was purchased from SuSoS AG, Switzerland. Alexa Fluor 488 was purchased from Life Technologies, Germany. The plasmid pd2EGFP-N1 was purchased from BD Biosciences Clontech, Germany.

Cell Culture

A human alveolar adenocarcinoma cell line (A549, ATCC CCL-185) was grown in Ham's F12K medium supplemented with 10% FBS. A human hepatoma epithelial cell line (Huh7, JCRB0403, JCRB Cell Bank, Japan) was cultured in DMEM medium, supplemented with 10% fetal bovine serum. All cell lines were grown in a humidified atmosphere at 5% $CO_2$ level.

In Vitro Transfection

Three hours prior to transfection, 10.000 cells per channel were seeded in a 6-channel slide. Cells were transfected at a dose of 5 pg mRNA/cell using the commercial transfection reagent Lipofectamine™ 2000 at a ratio of 2.5 µl Lipofectamine™ 2000 per 1 pg mRNA. The complex formation was prepared as follows: Lipofectamine™ 2000 and mRNA were separately diluted in OptiMEM transfection medium to add up to a total volume of 45 µl, each. These mixtures were incubated at room temperature for 5 minutes. The Lipofectamine™ 2000 solution was then mixed with the mRNA solution, followed by another 20 minutes of incubation at room temperature. Please note that the microchannels were never empty during all subsequent rinsing steps: Immediately before transfection, the cells were washed with PBS. Finally, the lipoplex solutions containing different mRNAs constructs were filled into the six channels. All five different mRNA constructs plus the reference construct could thus be measured under the same experimental conditions. The cells were incubated in a total transfection volume of 90 µl at 37° C. (5% $CO_2$ level) for one hour. The transfection medium was thereafter removed and the cells were washed with PBS. Subsequently, the cells were re-incubated with Leibovitz's L-15 Medium containing 10% FBS. A drop of anti-evaporation oil (ibidi GmbH, Germany) was added on top of each medium reservoir before microscopic monitoring of d2EGFP expression.

Data Acquisition and Quantitative Image Analysis

Live-cell imaging was performed on a motorized inverted microscope (Nikon, Eclipse Ti-E) equipped with an objective lens (CFI PlanFluor DL-10×, Phase1, N.A. 0.30; Nikon) and with a temperature-controlled mounting frame for the microscope stage. We used an ibidi heating system (Ibidi GmbH, Germany) with a temperature controller to stabilize the temperature of the samples at 37° C. (±2° C.) throughout the measurements. To acquire cell images, we used a cooled CCD camera (CLARA-E, Andor). A mercury light source (C-HGFIE Intensilight, Nikon) was used for illumination and a filter cube with the filter set 41024 (Chroma Technology Corp., BP450-490, FT510, LP510-565) was used for d2EGFP detection. An illumination shutter control was used to prevent bleaching. Images were taken at 10 fold magnification with a constant exposure time of 600 ms at 10 minute-intervals for at least 25 hours post-transfection. Fluorescence images were consolidated into single-image sequence files. Quantitative analysis of characteristic parameters of single-cell expression kinetics allows the comparison of various vector performances in terms of expression efficiency and stability. Image analysis consisted of several steps and was done using in-house-developed software based on ImageJ. First, a rectangular grid was overlaid with the original time-lapse movie and adjusted to the size and orientation of the underlying cell-pattern. Next, the software automatically detected d2EGFP-expressing cells by reading out the fluorescence intensities of all squares. Unoccupied squares were used for background correction. The software calculates the cells' fluorescence over the entire sequence and connects corresponding intensities to time courses of the fluorescence per cell. Finally, single-cell fluorescence intensities per square were extracted.

Data were then analyzed as described recently by fitting each time-course with the analytical solution for mRNA-induced protein expression (see equation 1) using IgorPro software, which is the solution to the differential equations for mRNA and d2EGFP, $$\frac{d}{dt}mRNA = -\delta \cdot m \qquad \text{(Equation 4)}$$

$$\frac{d}{dt}d2EGFP = k_{TL} \cdot m - \beta \cdot d2EGFP \qquad \text{(Equation 5)}$$

A schematic representation of the underlying simplistic model assumed for mRNA-induced protein expression is depicted in FIG. 3C.

II. Example 1: Fluorescence Microscopy and Analysis Via Flow Cytometry (FC)

To evaluate the effect of different UTR combinations on transgene expression kinetics, two different cells lines were transfected using Lipofectamine™2000 with different d2EGFP mRNA constructs containing a 5' UTR alone, a 3' UTR, 5'+3' UTR, two copies of 3'UTR and 5'+2×3' UTR. A schematic representation of the building blocks of all constructs can be seen in FIG. 1A.

At different time points through three days post-transfection, d2EGFP expression was quantified using FC. An exemplary dot plot for t=24h, illustrating d2EGFP expression levels of live A549 cells, is shown in FIG. 1C (see FIG. 7B for corresponding Huh7 data). In addition, we imaged the cells using fluorescence microscopy (see FIGS. 1B and D and FIGS. 7A and C). Comparable transfection efficiencies for all mRNA constructs were confirmed 24 hours post transfection (FIG. 1B and FIG. 8A). Thereby, differential transfer efficiencies to be a causal factor for the observed differences in expression kinetics can be ruled out. Based on fluorescence microscopy images, a drastic reduction of d2EGFP expression for all constructs at 48 h post-transfection was detected (see FIGS. 1B and D, FIGS. 7A and C). However, higher EGFP expression levels with respect to the control were found for all UTR-stabilized mRNAs. More specifically, mRNA constructs containing 3' UTRs seemed to enhance expression more than constructs without 3' UTRs. This was observed for A549 and Huh7 cells (see FIG. 1 and FIG. 7, respectively). At time points later than 48h, this effect was pronounced even more (data not shown). In FIGS. 2 A and B, the time courses of the mean fluorescence intensities (MFI) as determined by FC are shown for all constructs in both cell types.

Also here, all UTR-containing mRNA constructs showed higher MFI values than the control construct in both cell lines at all points in time. Taken together, the fluorescence microscopy and FC data suggest that mRNA molecules furnished with CYBA UTRs show persistent d2EGFP expression for more than 24 hours.

III. Example 2: Quantitative Real-Time PCR qRT-PCR measurement as an additional approach was conducted to determine the "physical" mRNA half-life of the different constructs. Binding of our selected primers to d2EGFP occurred 600 nt downstream of the start codon. Hence, measurements of physical mRNA half-life compromise both intact mRNAs and those which have either been decapped but not yet degraded or both decapped and degraded up to base 599. It also includes mRNA that has been removed from the translational pool and stored in P-bodies (29-32). Though intact mRNAs contribute to d2EGFP expression, the latter group of decapped and/or partially degraded transcripts, and those in P-bodies do not lead to any expression. Determination of physical mRNA half-life did not reveal any significant life time prolongation of the UTRs compared to the control in the A549 and Huh7 cells (see FIGS. 8A and B, respectively). Interestingly, instead a decrease in mRNA physical half-life for 5', 3', 5'+2×3' and 2×3' UTR constructs was observed in both cell lines.

Determination of mRNA Half-Life by qRT-PCR in A549 and Huh7 Cells

In an additional experiment, the mRNA half-life of the different mRNA constructs with qRT-PCR was investigated which is a conventional approach (see FIGS. 8A and B). Therefore, the mRNA constructs were transfected as described in herein. At the end, the absolute mRNA amount at each specific time point was obtained and calculated the mRNA half-life for each mRNA furnished with UTRs. No significant mRNA stabilization effects for any of the selected mRNA constructs as compared to the control were observed.

IV. Example 3: Single-Cell Expression Arrays

Microstructured, cell-adhesive substrates as shown in FIGS. 3A and B were fabricated as a platform for single-cell time-lapse microscopy.

The rectangular squares are functionalized with the extracellular matrix protein fibronectin, while the surrounding dark area is passivated with cell repellent PLL-g-PEG. Cells were seeded at an appropriately dilute cell density such that after about three hours, cells adhered to the rectangular squares. This cellular self-organization process has been studied in detail before (27). The size of the squares was 30 µm for optimal filling with single cells. The distance between the squares was just big enough (60 µm) to minimize bridging effects of cells adhering to more than one square at the same time. Time-lapse fluorescence microscopy and automated image analysis of the fluorescence signal per square yields hundreds of individual time courses. A typical set of background corrected raw data is shown in FIG. 3D. The black lines represent exemplary fits to the mathematical expression for mRNA translation (see also Materials and Methods section). Data were analyzed as described recently (26) by fitting each time-course with the analytical solution for mRNA-induced protein expression, $$G_{d2EGFP}(t) = \frac{K}{\delta - \beta} \cdot (1 - e^{-(\delta-\beta)(t-t_0)}) \cdot e^{-\beta(t-t_0)} \quad \text{(Equation 1)}$$

using IgorPro software. Here, G denotes the amount of protein, K is the expression rate, $\delta$ is the mRNA degradation rate, and $\beta$ is the degradation rate of the reporter protein d2EGFP. The expression rate $K=m_0 \cdot k_{TL}$ is the product of the initial amount of mRNA molecules inside the cell (m0) and the translation rate kTL. The time-course that is described by Equation 1 will be discussed in detail in below section "mastercurves of protein expression".

V. Example 4: In Vitro Transfection on Cell Arrays

In a typical experiment, cells were allowed to adhere to the micropatterns for three hours before transfection. Each of the six microchannels was filled with a different lipoplex solution, containing one of the constructs of interest. In initial experiments, we compared two different, commercially available transfection reagents (namely Lipofectamine™ 2000 and DOGTOR). Higher transfection efficiencies were found for Lipofectamine™ 2000 than for DOGTOR (see FIG. 9). Because additionally obtained high cell viability rates of above 80% were obtained with Lipofectamine™2000 (data not shown), all further transfection experiments were conducted using Lipofectamine™2000. As mRNA-mediated protein expression starts shortly after transfection, incubation time was kept to a minimum. Accordingly, the ratio between mRNA dosage and incubation time was adjusted to achieve high transfection efficiencies (see also FIG. 9) and negligible toxic effects caused by over-expression of the reporter protein. At an mRNA dose of 5 pg/cell, an incubation time of one hour was found to be optimal.

Transfection Efficiencies on Microstructured Substrates

The percentage of successfully transfected cells was assessed to compare two different transfection agents and to ensure that transfection efficiencies were not hampered by microstructured cell growth (see FIG. 9). Here, all cells grew on microstructured protein arrays. We obtained higher transfection efficiencies for Lipofectamine™ 2000 as compared to DOGTOR. Using a commercial Live/Dead cell viability assay (Molecular Probes, Germany), we found high cell viability rates above 80% (data not shown).

VI. Example 5: Expression Rates

All results for the two cell types are based on four independent measurements under the same experimental conditions. Time-lapse data of about thousand A549 cells and thousand Huh7 cells have been analyzed. The distributions of the obtained expression rates K are shown in FIG. 4A and the corresponding mean values can be seen in FIG. 4D.

Both the mean expression rates and the shape of their distributions were found to be rather similar for the different constructs.

VII. Example 6: mRNA Half-Lives

We converted the fitted mRNA-degradation rates $\delta$ into mRNA half-lives according to $$\tau = \frac{\ln 2}{\delta}. \quad \text{(Equation 2)}$$

FIG. 4B shows the half-life distributions of differently stabilized mRNA constructs in A549 and Huh7 cells, respectively. Here, it becomes evident that for stabilized constructs, both mean half-life and broadness of the underlying distribution increase as compared to the reference construct. An overview of all determined half-lives is given in FIG. 4D. Both for A549 and for Huh7 cells, we found longer half-lives for mRNAs stabilized by UTR elements compared to the control construct (5.8 hours for A549 cells and to 7.8 hours for Huh7 cells) that does not contain any stabilizing UTR. The life time prolonging effect was more pronounced in A549 cells.

VIII. Example 7: Protein Half-Lives

The distributions of protein (d2EGFP) degradation life times are presented in FIG. 4C. As expected the half-lives of the expressed protein do not vary for the different mRNA constructs. The determined mean life times range from 4.2 to 4.9 hours for A549 cells and from 5.6 to 8.5 hours for Huh7 cells as shown in FIG. 4D. The coefficients of variation are about 0.29 (A549) and 0.45 (Huh7) and hence is significantly smaller than the coefficient of variation of up to 0.6 that we found for the distribution on mRNA life-times. As a control, the half-lives in an alternative approach were also measured, where translation was inhibited by addition of cycloheximide at a given time point, to, after transfection (see FIG. 10). In this case, protein expression is induced for a while and then stopped. The exponential decay in fluorescence after inhibition yields protein life times. These half-lives were found to be smaller by a factor of about two, compared to the above experiments without inhibition. In both experiments, however, the relative ratios of the protein life times in Huh7 cells as compared to those in A549 cells is the same.

Degradation Rate of the Reporter Protein

To check the fitted d2EGFP degradation rates, the degradation rate of d2EGFP inside A549 and Huh7 cells were independently measured in microstructured six-channel slides. Protein synthesis was blocked by the antibiotic cycloheximide, which interferes with peptidyl transferase activity (42). Single-cell fluorescence intensity time courses were monitored for approximately 20h (see FIG. 10). Control experiments ensured that the decrease in fluorescence intensity was not due to photobleaching of the chromophore. Single-cell time courses were fitted by a single exponential fit, yielding distributions of protein degradation rates. The mean degradation rates were found to be 0.28/h (std 0.08/h)

in A549 cells and 0.17/h (std 0.08/h) in Huh7 cells, corresponding to protein life times of 2.46 h and 4.04 h, respectively. Although these life times are significantly shorter than the life times as determined by single-cell time course analysis of mRNA mediated protein expression, the ratio between the mean life times of d2EGFP inside Huh7 and A549 cells is the same (4.04 h/2.46 h=1.64 as measured by translational blocking compared to 7.4 h14.5 h=1.64 as determined by fitting the analytical solution for mRNA expression).

IX. Example 8: Mastercurves of Protein Expression

The features of mRNA induced protein expression become evident in the so-called mastercurve of protein expression as depicted in FIG. 5A (A549) and B (Huh7).

The mastercurve is the population average of the onset-time corrected single cell traces, i.e. all onset-times were shifted to time point zero. Fluorescence intensities were converted into actual numbers of d2EGFP as described before in reference (26). The superior properties of the 3' and the 5'+3'-stabilized mRNA constructs are illustrated in the mastercurve plot. These constructs showed the shallowest decrease in protein expression with time and hence the longest half-lives in addition with higher protein expression values as compared to the other constructs.

X. Example 9: Area Under the Curve (AUC)

In pharmacokinetics, the total exposure of a drug is known as the "area under the curve". The analogous expression in gene therapy is the integral of the amount of artificially expressed protein over time, i.e. the area under the (expression-vs.-time) curve (AUC). The AUC is a means to simultaneously quantify the translational efficiency and the stability of an mRNA construct. It can be interpreted as the cumulative time-dose of the protein that is encoded on the mRNA and hence describes the efficacy of a chosen mRNA construct. Given the biochemical rate model (see FIG. 3A) the AUC can be explicitly calculated:

$$AUC = 0.48 \cdot m_0 \cdot k_{TL} \cdot \tau_{mRNA} \cdot \tau_{d2EGFP} \qquad \text{(Equation 3)}$$

Hence an optimal therapeutic mRNA construct should desirably have both long mRNA, τmRNA, as well as protein half-life, τd2EGFP, and high translational efficiency, kTL. In addition, the transfer efficiency which determines the initial amount of therapeutic mRNA, m0, is directly proportional to the AUC. An illustrative explanation for the theoretical time course of protein expression and calculated AUC can be seen in FIG. 6A.

If there was no protein degradation (β=0), the amount of protein inside a cell would run into a steady state level as a consequence of a balanced flux of mRNA translation and mRNA degradation. In this case the expression dynamics follows $$\frac{K}{\delta}(1-e^{-\delta t}).$$

The same would be true in an analogous manner for the case where δ was equal to zero. The superposition of this with the permanent, exponential decay of the d2EGFP protein (following $e^{-\beta_1}$) results in the characteristic shape of the AUC as shown in FIG. 6A. FIGS. 6B and C show the overall mean relative AUCs as well as the "per-experiment" relative AUCs normalized to the mean AUC of the control, the latter being the AUC of protein expression after transfection with the control construct. In both cell types, the highest relative AUCs was found for the 3'UTR- and the 5'+3'UTR-stabilized construct. This is consistent with the observed long half-lives for these constructs, because they contribute to the AUC as seen in equation 3. The detailed, single-cell AUC distributions can be found in FIG. 11.

More specifically, assuming biochemical rate equations (4) and (5) for translation and degradation according to FIG. 3C, the amount of expressed protein after mRNA transfection is given by $$G_{d2EGFP}(t) = \frac{K}{\delta-\beta} \cdot (1-e^{-(\delta-\beta)(t-t_0)}) \cdot e^{-\beta(t-t_0)}. \qquad \text{(Equation 1)}$$

The area under the curve (AUC) is calculated by integrating the expression level $G_{d2EGFP}(t)$ from $t_0$, when expression sets in to long times (t→∞):

$$AUC = \int_{t=t_0}^{t=\infty} G(t) =$$

$$\frac{K}{\delta-\beta}\int_0^\infty [e^{-\beta\tau}-e^{-\delta\tau}]d\tau = \frac{K}{\delta-\beta} \cdot \left[\frac{1}{\beta}-\frac{1}{\delta}\right] = \frac{K}{\delta \cdot \beta} \text{ with } \tau = t-t_0.$$

Using $\tau_{mRNA}=\ln 2/\delta$, $\tau_{d2EGFP}=\ln 2/\beta$, and $K=m_0 \cdot k_{TL}$ equation 3 is obtained:

$$AUC = 0.48 \cdot m_0 \cdot k_{TL} \cdot \tau_{mRNA} \cdot \tau_{d2EGFP}$$

The time course of $G_{d2EGFP}(t)$ and the AUC is schematically depicted in FIG. 6A.

The experimental single-cell AUC distributions can be seen in FIG. 11. Because the AUC depends linearly from the mRNA and protein life times, the single-cell AUC distributions are closely related to the mRNA and protein half-life distributions that are shown in FIGS. 4B and 4C of the main text.

XI. Example 10: Life Time-Prolongation Factor

The life time-prolongation factors for A549 and Huh7 cells are shown in FIGS. 6D and E, respectively. As expected, all stabilized constructs yield life time-prolongation factors higher than one, meaning that the insertion of UTRs at either end causes mRNA stabilization. However, the 3'UTR mRNA construct shows longer mRNA life times than the 2×3'UTR construct. Similarly, the 5'+3'UTR construct is more stable than the 5'+2×3' construct. These results hold true for both cell types. Interestingly, the stabilizing effects are significantly more pronounced in A549 cells than in Huh7 cells in all cases.

XI. Example 11: Comparison of Constructs Having UTRs of Different Genes Compared to the CYBA-UTR Construct The constructs #2 to #5 having UTRs of different genes as indicated in the below Table 4 have been compared to the CYBA-UTR construct #1 in order to optimize the mRNA structure in terms of stability and productivity. Five different cellular UTRs of a gene were selected based on publication data (Hoen et al., 2010) featuring long mRNA half-lives. These cellular UTRs are CYBA, DECR1, GMFG, MAPBPIP and MYL6B. The sequences of 5' and 3' untranslated regions of each cellular gene were obtained from the UTR database (http://utrdb.ba.itb.cnr.it/search) and were cloned into five different combinations, which were 5'UTR alone, 3'UTR alone, 5'+3'UTR, 5'+2×3'UTR and 2×3'UTR.

Firstly, the untranslated region sequences were cloned into the backbone pVAX1-A120. In case of the 5'UTRs, cloning occurred via HindIII restriction site on the 5'end and BamHI restriction site on the 3'end and was inserted upstream of the reporter gene coding for Metridia luciferase (MetLuc). The restriction sites for 3'UTRs were EcoRI (5'end) and PstI (3'end) and were cloned downstream of MetLuc. The plasmids containing 5' UTR alone and 5'+3'UTR for each cellular UTR were produced by Eurofins MWG Operon. These plasmids were transformed into *E. coli* bacteria (DH10B) via electroporation. The other combinations, including 3'UTR alone, 5'+2×3'UTR and 2×3' UTR were cloned in-house. Cloning of plasmids with 3'UTR was performed by simply cutting out the 5'UTR of the backbone via HindIII (blunt) and BamHI (blunt) digestion. Constructs containing 5'UTR+2×3'UTR were cloned by inserting MetLuc containing 3'UTR (BamHI/PstI blunt) into the backbone of pVAX1-A120 MetLuc comprising 5'+3'UTR, thereby replacing MetLuc and inserting a second 3'UTR in front of the respective 3'UTR of the backbone. Finally, the constructs containing 2×3'UTR were generated by removing the 5'UTR (HindIII and BamHI, both blunt) from the plasmid containing 5'+2×3'UTR. After cloning, all plasmids were amplified in *E. coli* bacteria (DH10B) after electroporation.

Secondly, chemically modified mRNA was produced by in vitro transcription. For that purpose, the plasmids were linearized with XbaI digestion and were purified with chloroform/ethanol precipitation. The in vitro transcription kit (Promega) included the required T7 polymerase enzyme mix as well as the suitable buffers. The transcription mix also contained the unmodified nucleotides adenosine-triphosphate (ATP), guanosine-triphosphate (GTP), uridine-triphosphate (UTP) and cytosine-triphosphate (CTP) as well as the chemically modified nucleotides methyl-CTP and thio-UTP (Jena Bioscience, GmbH, Jena, Germany) with a final concentration of ATP:GTP:UTP:CTP:methyl-CTP:thio-UTP of 7.13 mM:1.14 mM:5.36 mM:5.36 mM:0.536 mM:0.536 mM. Additionally, the cap structure analog ARCA (anti-reverse cap analog) was added to the mix to ensure the incorporation of the 5'-cap in the right direction. Finally, the linearized DNA was added into the reaction mix. The IVT mix was incubated at 37° C. for 2 h. Digestion of the remaining DNA was enabled by the addition of DNase I and further incubation at 37° C. for another 20 min. RNA precipitation was performed by the addition of pre-cooled ammonium-acetate to a final concentration 2.5 M. The RNA pellet was washed with 70% ethanol. The washing step was performed twice. At last, the RNA was re-suspended in RNase-free water. The RNA concentration was determined with a spectrophotometric device and purity was tested on an agarose gel.

After IVT, the different mRNAs were tested in two different cell lines, i.e., in NIH3T3 and A549. For the screening experiments a non-viral nucleic acid delivery system, like lipofection, was used. In a first transfection experiment, different transfection agents were tested to compare protein expression and cell viability (data not shown).

Next, the screening experiments including dose titration were conducted to evaluate dose dependent effects. The experimental set-up is as follows: 5000 cells (N1H3T3) in 150 μl DMEM complete medium were seeded per well in 96-well plates and transfected 24 hours post-seeding. Cells were transfected at a starting dose of 500 ng/well (100 pg mRNA/cell) using the commercial transfection reagent Dreamfect Gold (DFG). Complexes were prepared at a ratio of 4 μl Dreamfect Gold per 1 μg mRNA. For the formation of lipoplexes, mRNA (3.6 μg) was diluted separately in DMEM without supplements in a total volume of 340 μl for each mRNA. In a 96 well plate 14.4 μl DFG was mixed with 5.6 μl water in one well prepared for each mRNA dilution. Complex formation took place when the mRNA dilution was added to the DFG and mixed by up and down pipetting. The mixtures were incubated at room temperature for 20 minutes. In the meantime, the dilution series were prepared. In the remaining seven wells subjacent of the complex mix, 180 μl DMEM without supplements per well was added. After incubation time 180 μl of the complex solution was removed and added into the first well of dilution series. This procedure was conducted until the last dilution step. Finally, 50 μl of the complex solution were added to the cells and incubated for 4 hour. For every mRNA construct, biological triplicates were prepared. After 4 hours, the complete supernatant was removed from the cell culture plate for measurement and fresh 150 μl medium was added to each well. Bioluminescence was measured after 4, 24, 48, 72, 96, 120 and 144 hours using a multilabel plate reader. To this 50 μl of supernatant was mixed with 20 μl coelenterazin and the generated light was measured. Finally the protein amount over time was observed and is depicted as area under the curve (AUC).

The results are shown in FIG. 12.

TABLE 4 summary of the constructs #1 to #5.

| # | Name | 5' UTR | 3' UTR |
|---|------|--------|--------|
| 1 | CYBA | — | Insulin 3'UTR stability element (INS_SCE), Polyadenylation Signal (PAS) |
| 2 | DECR1 (2,4-dienoyl CoA reductase 1, mitochondrial) | SNP | PAS, PhastConsElements17way (conserved block) |
| 3 | GMFG (glia maturation factor, gamma) | Upstream Open Reading Frame (uORF), PhastConsElementsI 7way (2x) | PAS |

TABLE 4-continued summary of the constructs #1 to #5.

| # | Name | 5' UTR | 3' UTR |
|---|---|---|---|
| 4 | MAPBPIP (late endosomal/lysosomal adaptor, MAPK and MTOR activator 2) | — | PAS |
| 5 | MYL6B (Myosin Light Chain 6B) | — | PAS, PhastConsElements17way |

XIII. Discussion

Determination of mRNA stability and its expression are two major factors to be considered when it comes to developing new mRNA therapeutics. Here, different combinations of UTRs, a 5' UTR, 3'UTR, a 5'+3' UTR, 5'+2×3' UTR, and two copies 3' UTR were used to improve mRNA in terms of stability and its expression. The AUC of the d2EGFP time course is also evaluated, because the total protein expression is relevant for a sustained therapeutic effect. In order to get detailed time-resolved data and monitor protein expression dynamics at the single-cell level, microstructured single-cell arrays for parallel, quantitative measurements of mRNA stability and translational efficiency were used. The regular arrangement of cells guaranteed reproducible microenvironments and enabled fast and automated image-analysis, which are prerequisites for comparative, high-throughput single-cell studies. The approach allows the determination of distribution functions for (i) protein half-life, (ii) expression rates, and (iii) functional mRNA half-life.

In both A549 and Huh7 cells, mean protein half-lives of d2EGFP were narrowly distributed and independent of the UTR sequence. The calculated half-life values of 4.5 hours for A549 cells and 7.4 hours for Huh7 cells could be attributed to cell type specific differences between the compared cell lines. Such cell specific differences in d2EGFP half-life have been published previously. A study in NIH3T3 cells using a similar imaging cytometry approach, recorded a half-life of 2.8 h within a measurement window of 12 hours (33). An even shorter half-life of less than two hours has been reported for CHO cells by Li et al. (34). Here, protein degradation was measured by Western blotting and flow cytometry for three hours only.

To validate our findings from single-cell data analysis, d2EGFP life times in direct measurements using cycloheximide were additionally determined (see FIG. 10). Shorter life times as compared to the values observed from single-cell data analysis were found. This might be due to the fact that in single-cell data analysis, a constant initial number of mRNA molecules was assumed as part of the combined expression rate $K=m_0-k_{TL}$ (see Equation 1). However, regardless of the fact that cells have been washed after one hour incubation time, it is still likely that the number of mRNA molecules is not constant from the start of observation. As a consequence, mRNA molecules that are available for translation later on, leading to protein expression, might result in longer half-life values obtained from single-cell expression time course fitting. When the mean half-life determined for A549 cells with the mean half-life determined for Huh7 cells is compared, the same ratio of roughly 1.64 for both measurement methods is found. Also, even a possible systematic over-estimation of mRNA and protein half-lives does not change the qualitative order of the mRNA performance.

The expression rate depends on the initial number of mRNA molecules, m0, as well as on the translation rate KTL. It is to be noted that the number of successfully delivered mRNA molecules varies due to the intrinsic stochasticity of the delivery process. The mean number of mRNA molecules, however, is expected to be the same, since the transfection protocol has scrupulously been kept up in all experiments. In contrast, the translational activity (KTL) of the various UTR constructs might vary. Still, the fact that the distributions as well as the mean values of the expression rate K are rather similar for all constructs (see FIGS. 3A and D) indicates that the translation rate is merely influenced by the inserted UTRs.

The parameter of highest interest is the mRNA half-life. Here functional mRNA half-life was compared to physical mRNA half-life. The results with single cell transfection studies suggest that any insertion of 5' or 3' UTRs into the mRNA sequence increases its functional mRNA half-life. All modifications tested in this study led to prolonged mRNA half-lives (see FIGS. 2 and 3), thereby resulting in prolonged expression as measured by fluorescence microscopic imaging and FC (see FIG. 1). In contrast to the functional mRNA half-life, the physical mRNA half-life determined by qRT-PCR showed a decrease in mRNA stability for 5', 3', 5'4-2×3' and 2×3' UTR in both cell lines (see FIGS. 8A and B). One major difference is the translational capacity for every measured mRNA in both methods. In the case of measuring functional mRNA half-lives, the mRNA is involved in active translation, whereas the physical mRNA half-life is monitored regardless of the translational status of the detected mRNA. Similar findings have been reported by Gallie et al. (35). It is believed that the physical mRNA half-life is not an appropriate indicator of the translational capacity of the mRNA. Translational capacity for a mRNA could be judged from it's functional half life (longevity of expression) and the amount of total protein produced (Area Under the Curve). For a therapeutic mRNA, it is imperative that the molecule is functional for as long as possible and produces maximum possible protein. This leads to the conclusion that both functional mRNA half-life and total amounts of produced protein are better measures for identifying, comparing and testing mRNA therapeutics. Furthermore, the heterogenic distribution of the half-lives points out the importance of single-cell measurement techniques, because these effects are obscured in ensemble measurements (see FIGS. 2, 4, and 8A and B). Interestingly, a positive effect on protein expression was observed for 5' UTR alone, although so far, no known motif in the CYBA 5' UTR has been discovered. For the first time, it has been shown that CYBA UTRs at either end suffice to increase both peak and persistence of protein expression in both cell lines. These findings are consistent with publications claiming individual or synergistic behavior of 5' UTRs and 3' UTRs (14). In contrast to Holtkamp et al. (16), no additional increase in protein expression or mRNA stability could be observed with two sequential copies of the 3'UTR as compared to one single 3' UTR (see FIG. 4). Conversely, it even resulted in shorter life times both for 5'+3' versus 5'+2×3' UTR insertion and for 3' versus 2×3' UTR insertion. This might be due to the fact that a different type of cells (namely dendritic cells) was used in the study by Holtkamp et al. (16). Similar cell type specific effects have been reported for hepatocytes, too (39). Another contributing factor affecting both mRNA stability and its translation efficiency might be the secondary structure of the different mRNAs. Such effects of mRNA secondary structure in regulating gene expression have been reported before (36,37). Important structural characteristics together with their minimum free energy for the mRNA constructs used in the current study are summarized in Table 3.

The persistent protein expression of the 5'+3'UTR stabilized construct could be due to binding of the 5' to the 3'end, which facilitates circularization of the mRNA (19). Because no stable secondary structures within the 5' UTR could be found, it is assumed that this feature enables an early expression onset (38). In contrast, secondary structures within the 3' UTRs were identified. These might protect the mRNA from the 3'-5' degradation pathway. Two 3' UTRs showed even more secondary structures (two hairpins) with the best minimum free energy, indicating more persistent expression. Taken together, these findings could be the explanation for the inferior onset expression of the 2×3' UTR compared to the 5'UTR and the persistent expression at later time points of mRNA constructs containing 3' UTRs. In accordance with protein half-lives, longer half-life values were obtained for mRNAs stabilized with UTRs. This was observed in both cell lines with cell specific differences most likely affecting the absolute values. In A549 cells, mRNA half-lives for the constructs with UTRs ranged from 13.0 h to 23.0 h as compared to 5.8 h for the control. In Huh7 cells, half-lives from 9.9 h to 13.6 h were measured for UTR-containing constructs, as opposed to a half-life of 7.8 h for the control mRNA. The half-life of the 3'UTR-stabilized mRNA in A549 cells is in good agreement with mRNA life times of similarly stabilized mRNAs that were reported previously (16,26). The fact that stability and decay kinetics of mRNA and protein differ in different cell types is most likely due to differences in the complex networks of interactions between mRNA and proteins which are very likely to be cell-type dependent.

Taken together, our results in both A549 and Huh7 cells, independent of the analysis method (FC or single-cell analysis), suggest that sustained, high levels of protein expression can be induced by CYBA UTR stabilized mRNA. The choice of UTR combination depends on the need of the experiment of application. Where persistent protein expression with reduced mRNA decay is desired, mRNA stabilized with a 3' UTR alone might serve the purpose. However, the combination of 5'+3' UTR results in additional desirable features of early onset, high peak and cumulative protein expression.

It is demonstrated here that single-cell analysis of mRNA-induced protein expression is a means to characterize and improve pharmacokinetic properties of mRNA constructs. Using this approach, it is possible to systematically assess the intracellular bioavailability of different mRNA constructs to identify sequences yielding sustained protein expression. Prolonged persistence of protein expression was found for constructs stabilized by UTR insertions using a single-cell model and FC analysis in two cell types. This finding is desired in case of developing mRNA therapeutics. Messenger RNA constructs with persistent protein expression over a period of time (AUC) is desirable and allows proper reduced dosing into a patient with a final therapeutic outcome.

REFERENCES

1. G. Tavernier, O. Andries, J. Demeester, N. N. Sanders, S. C. De Smedt and J. Rejman, *J Control Release*, 2011, 150, 238-247.
2. A. Yamamoto, M. Kormann, J. Rosenecker and C. Rudolph, *Eur J Pharm Biopharm*, 2009, 71, 484-489.
3. M. S. D. Kormann, G. Hasenpusch, M. K. Aneja, G. Nica, A. W. Flemmer, S. Herber-Jonat, M. Huppmann, L. E. Mays, M. Illenyi, A. Schams, M. Griese, I. Bittmann, R. Handgretinger, D. Hartl, J. Rosenecker and C. Rudolph, *Nat Biotech*, 2011, 29, 154-157.
4. M. Esteller, *Nat Rev Genet*, 2011, 12, 861-874.
5. K. Kariko and D. Weissman, *Current Opinion in Drug Discovery and Development*, 2007, 10, 523.
6. G. Pesole, G. Grillo, A. Larizza and S. Liuni, *Briefings in Bioinformatics*, 2000, 1, 236-249.
7. T. V. Pestova, J. R. Lorsch and C. U. Hellen, *Cold Spring Harbor Monograph Archive*, 2007, 48, 87-128.
8. L. Barrett, S. Fletcher and S. Wilton, *Cell. Mol. Life Sci.*, 2012, 69, 3613-3634.
9. F. Mignone, G. Grillo, F. Licciulli, M. Iacono, S. Liuni, P. J. Kersey, J. Duarte, C. Saccone and G. Pesole, *Nucleic Acids Research*, 2005, 33, D141-D146.
10. M. J. Moore, *Science*, 2005, 309, 1514-1518.
11. X. Pichon, L. A. Wilson, M. Stoneley, A. Bastide, H. A. King, J. Somers and A. E. Willis, *Current Protein & Peptide Science*, 2012, 13, 294-304.
12. P. A. C. 't Hoen, M. Hirsch, E. J. d. Meijer, R. X. d. Menezes, G. J. van Ommen and J. T. d. Dunnen, *Nucleic Acids Research*, 2011, 39, 556-566.
13. G. Pesole, F. Mignone, C. Gissi, G. Grillo, F. Licciulli and S. Liuni, *Gene*, 2001, 276, 73-81.
14. F. Gebauer and M. W. Hentze, *Nat Rev Mol Cell Biol*, 2004, 5, 827-835.
15. L. Tillmar, C. Carlsson and N. Welsh, *Journal of Biological Chemistry*, 2002, 277, 1099-1106.
16. S. Holtkamp, S. Kreiter, A. Selmi, P. Simon, M. Koslowski, C. Huber, O. Tureci and U. Sahin, *Blood*, 2006, 108, 4009-4017.
17. C. H. d. Moor, H. Meijer and S. Lissenden, *Seminars in Cell & Developmental Biology*, 2005, 16, 49-58.
18. N. L. Garneau, J. Wilusz and C. J. Wilusz, *Nat Rev Mol Cell Biol*, 2007, 8, 113-126.
19. E. Szostak and F. Gebauer, *Briefings in Functional Genomics*, 2012.
20. S. Tyagi, *Nat Meth*, 2009, 6, 331-338.
21. H. Y. Park, H. Lim, Y. J. Yoon, A. Follenzi, C. Nwokafor, M. Lopez-Jones, X. Meng and R. H. Singer, *Science*, 2014, 343, 422-424.
22. C. Miller, B. Schwalb, K. Maier, D. Schulz, S. Dümcke, B. Zacher, A. Mayer, J. Sydow, L. Marcinowski, L. Milken, D. E. Martin, A. Tresch and P. Cramer, *Molecular Systems Biology*, 2011, 7.
23. T. Nolan, R. E. Hands and S. A. Bustin, *Nat. Protocols*, 2006, 1, 1559-1582.
24. M. Rabani, J. Z. Levin, L. Fan, X. Adiconis, R. Raychowdhury, M. Garber, A. Gnirke, C. Nusbaum, N. Hacohen, N. Friedman, I. Amit and A. Regev, *Nat Biotech*, 2011, 29, 436-442.

25. B. Schwanhausser, D. Busse, N. Li, G. Dittmar, J. Schuchhardt, J. Wolf, W. Chen and M. Selbach, *Nature*, 2011, 473, 337-342.
26. C. Leonhardt, G. Schwake, T. R. Stogbauer, S. Rappl, J.-T. Kuhr, T. S. Ligon and J. O. Rädler, *Nanomedicine: Nanotechnology, Biology and Medicine*, 2014, 10, 679-688.
27. P. J. F. Rottgermann, A. P. Alberola and J. O. Radler, *Soft Matter*, 2014.
28. P. Corish and C. Tyler-Smith, Protein Engineering, 1999, 12, 1035-1040.
29. J. J. Rossi, *Nat Cell Biol*, 2005, 7, 643-644.
30. U. Sheth and R. Parker, *Cell*, 2006, 125, 1095-1109.
31. A. Jakymiw, K. M. Pauley, S. Li, K. Ikeda, S. Lian, T. Eystathioy, M. Satoh, M. J. Fritzler and E. K. L. Chan, *Journal of Cell Science*, 2007, 120, 1317-1323.
32. R. Parker and U. Sheth, *Molecular Cell*, 2007, 25, 635-646.
33. M. Halter, A. Tona, K. Bhadriraju, A. L. Plant and J. T. Elliott, *Cytometry Part A*, 2007, 71A, 827-834.
34. X. Li, X. Zhao, Y. Fang, X. Jiang, T. Duong, C. Fan, C.-C. Huang and S. R. Kain, *Journal of Biological Chemistry*, 1998, 273, 34970-34975.
35. D. R. Gallie, *Genes & Development*, 1991, 5, 2108-2116.
36. J.-M. Chen, C. Férec and D. Cooper, *Hum Genet*, 2006, 120, 301-333.
37. P. Gaspar, G. Moura, M. A. Santos and J. L. Oliveira, *Nucleic acids research*, 2013, 41, e73-e73.
38. J. R. Babendure, J. L. Babendure, J.-H. Ding and R. Y. Tsien, *RNA* (New York, N.Y., 2006, 12, 851-861.
39. B. T. Kren and C. J. Steer, *FASEB J.*, 1996, 10, 559-573.
40. Zuker, M. (2003) Mfold web server for nucleic acid folding and hybridization prediction. *Nucleic acids research*, 31, 3406-3415.
41. Babendure, J. R., Babendure, J. L., Ding, J.-H. and Tsien, R. Y. (2006) Control of mammalian translation by mRNA structure near caps. *RNA* (New York, N.Y., 12, 851-861.
42. Siegel, M. R. and Sisler, H. D. (1963) Inhibition of Protein Synthesis in vitro by Cycloheximide. *Nature*, 200, 675-676.
43. Friedel C C, Dölken L, Ruzsics Z, Koszinowski U H, Zimmer R. (2009) Conserved principles of mammalian transcriptional regulation revealed by RNA half-life. *Nucleic acids research*, 37, e115.

The invention claimed is:

1. An RNA molecule comprising
   (a) a coding region coding for a polypeptide; and
   (b) upstream of said coding region one or more UTR(s) comprising the sequence as shown in SEQ ID NO:1 or a sequence which shows 1 to 4 substitutions in comparison to SEQ ID NO:1 and which results in an RNA molecule having the same or a higher translation efficiency as an RNA molecule comprising an UTR comprising SEQ ID NO:1; and/or
   (c) downstream of said coding region one or more UTR(s) comprising the sequence as shown in SEQ ID NO:2 or a sequence which shows 1 to 7 substitutions in comparison to SEQ ID NO:2 and which results in an RNA molecule having the same or a higher translation efficiency as an RNA molecule comprising an UTR comprising SEQ ID NO:2;
   wherein said polypeptide encoded by said coding region is not a cytochrome b-245 alpha polypeptide (CYBA).

2. The RNA molecule of claim 1, wherein said UTR(s) as defined in claim 1(b) is/are located at the 5' end of the coding region as defined in claim 1(a).

3. The RNA molecule of claim 1, wherein said UTR(s) as defined in claim 1(c) is/are located at the 3' end of the coding region as defined in claim 1(a).

4. The RNA molecule of claim 1, wherein said UTR(s) as defined in claim 1(b) is/are located at the 5' end of the coding region as defined in claim 1(a) and wherein said UTR(s) as defined in claim 1(c) is/are located at the 3' end of the coding region as defined in claim 1(a).

5. The RNA molecule of claim 1, which comprises one UTR as defined in claim 1(b) at the 5' end of the coding region as defined in claim 1(a) and which comprises two UTRs as defined in claim 1(c) at the 3' end of the coding region as defined in claim 1(a).

6. The RNA molecule of claim 1, which comprises two UTRs as defined in claim 1(c) at the 3' end of the coding region as defined in claim 1(a).

7. The RNA molecule of claim 1, wherein the RNA molecule comprises a poly-A tail at the 3' end.

8. The RNA molecule of claim 1, wherein the poly-A tail has a length of at least 120 nucleotides.

9. A nucleic acid molecule encoding the RNA molecule of claim 1.

10. A vector comprising the nucleic acid molecule of claim 9.

11. A host cell comprising the vector of claim 10.

12. A pharmaceutical composition comprising the RNA molecule of claim 1, the nucleic acid molecule of claim 9, the vector of claim 10 or the host cell of claim 11 and optionally a pharmaceutically acceptable carrier.

13. The pharmaceutical composition of claim 12 for use in RNA-based therapies.

14. A kit comprising the RNA molecule of claim 1, the nucleic acid molecule of claim 9, the vector of claim 10 or the host cell of claim 11.

15. A method of increasing the efficiency of translating a coding region of an RNA molecule into a polypeptide or a protein encoded by said coding region comprising using one or more UTR(s) as defined in claim 1(b) and/or one or more UTR(s) as defined in claim 1(c).

16. The RNA molecule of claim 1, wherein said UTR(s) as defined in claim 1(b) comprise the sequence as shown in SEQ ID NO:1 and is/are located at the 5' end of the coding region as defined in claim 1(a), and
   wherein said UTR(s) as defined in claim 1(c) comprise the sequence as shown in SEQ ID NO:2 and is/are located at the 3' end of the coding region as defined in claim 1(a).

* * * * *